(12) United States Patent
Bolton et al.

(10) Patent No.: US 12,134,632 B2
(45) Date of Patent: Nov. 5, 2024

(54) ON-COLUMN VIRAL INACTIVATION METHODS

(71) Applicant: BIOVERATIV THERAPEUTICS INC., Waltham, MA (US)

(72) Inventors: Glen Bolton, Boston, MA (US); Keith Selvitelli, Sutton, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 0 days.

(21) Appl. No.: 18/153,669

(22) Filed: Jan. 12, 2023

(65) Prior Publication Data

US 2023/0331774 A1   Oct. 19, 2023

Related U.S. Application Data

(63) Continuation of application No. 16/793,676, filed on Feb. 18, 2020, now Pat. No. 11,578,098, which is a
(Continued)

(51) Int. Cl.
| | |
|---|---|
| A61L 2/00 | (2006.01) |
| A61K 35/14 | (2015.01) |
| A61K 35/16 | (2015.01) |
| A61K 38/00 | (2006.01) |
| C07K 1/16 | (2006.01) |
| C07K 1/22 | (2006.01) |
| C07K 14/755 | (2006.01) |
| C07K 16/06 | (2006.01) |

(52) U.S. Cl.
CPC .............. *C07K 1/22* (2013.01); *A61L 2/0088* (2013.01); *C07K 1/165* (2013.01); *C07K 14/755* (2013.01); *C07K 16/065* (2013.01); *A61L 2202/21* (2013.01); *C07K 2319/30* (2013.01)

(58) Field of Classification Search
CPC .. B08B 9/027; B08B 3/08; A61L 2/18; A61K 35/16; C07K 1/22; C12N 9/6437
USPC ....... 422/1, 28; 514/1.4, 15.3; 530/380, 205, 530/435; 424/530
See application file for complete search history.

(56) References Cited

U.S. PATENT DOCUMENTS

| | | | |
|---|---|---|---|
| 4,683,195 | A | 7/1987 | Mullis et al. |
| 4,965,199 | A | 10/1990 | Capon et al. |
| | | (Continued) | |

FOREIGN PATENT DOCUMENTS

| | | | |
|---|---|---|---|
| EP | 0506757 | B2 | 10/2005 |
| EP | 3048899 | A2 | 12/2016 |
| | (Continued) | | |

OTHER PUBLICATIONS

"Montage Spin Columns with PROSEP/G media." 3 pages (Jul. 6, 2011).

(Continued)

*Primary Examiner* — Monzer R Chorbaji
(74) *Attorney, Agent, or Firm* — LATHROP GPM LLP; James H. Velema, Esq.

(57) ABSTRACT

The present invention is directed to a method of inactivating virus that is present during production of a polypeptide of interest. In particular, the present invention is directed to a method of on-column virus inactivation using a low pH and high salt wash solution that effectively inactivates viruses with minimum recovery loss of the polypeptide.

21 Claims, 15 Drawing Sheets

Figure 1:
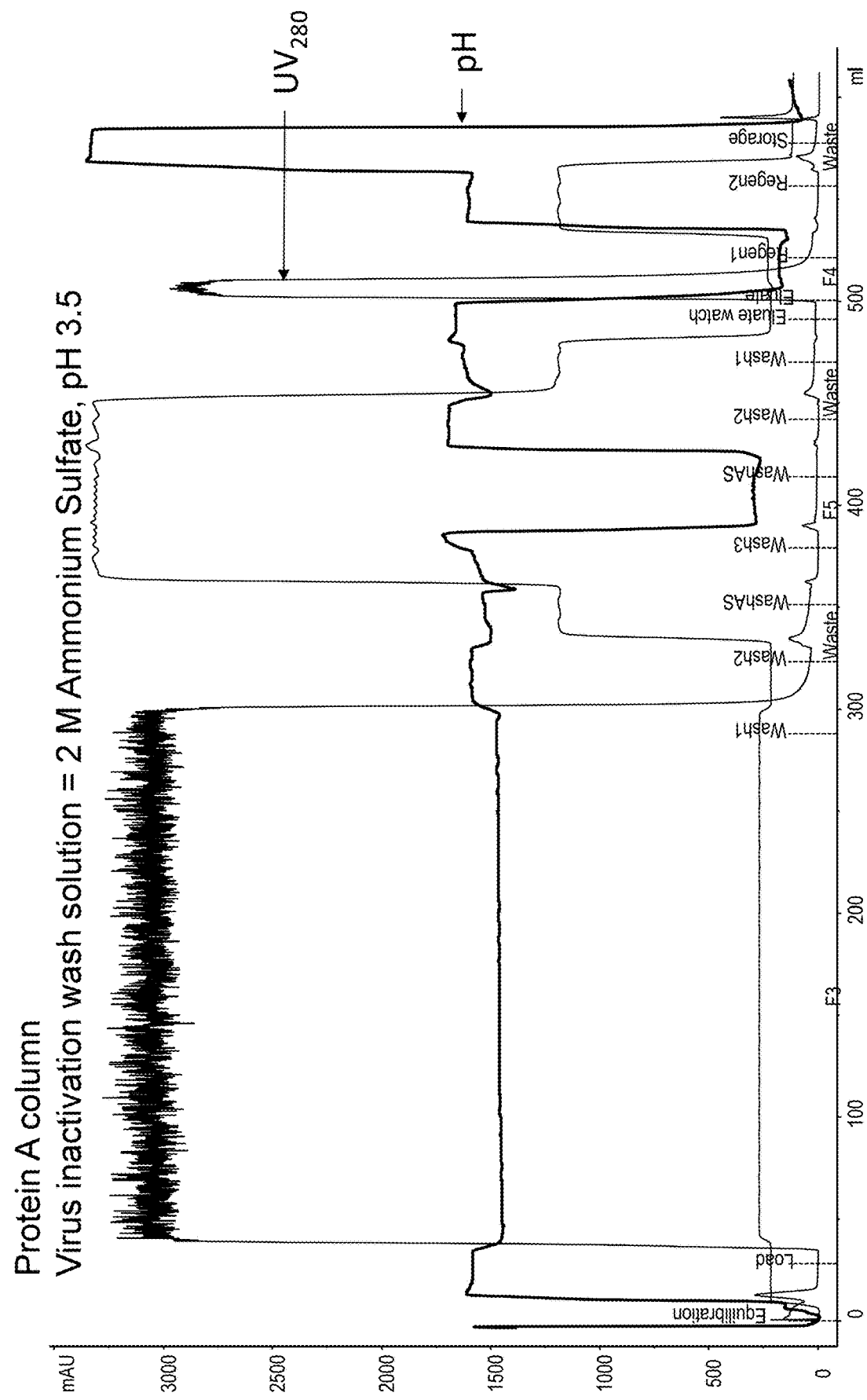

Specification includes a Sequence Listing.

Related U.S. Application Data continuation of application No. 15/024,988, filed as application No. PCT/US2014/057524 on Sep. 25, 2014, now Pat. No. 10,611,794.

(60) Provisional application No. 62/028,657, filed on Jul. 24, 2014, provisional application No. 61/882,488, filed on Sep. 25, 2013.

(56) References Cited

U.S. PATENT DOCUMENTS

| | | |
|---|---|---|
| 5,223,409 A | 6/1993 | Ladner et al. |
| 5,429,746 A | 7/1995 | Shadle et al. |
| 5,585,089 A | 12/1996 | Queen et al. |
| 5,643,575 A | 7/1997 | Martinez et al. |
| 5,648,260 A | 7/1997 | Winter et al. |
| 5,658,727 A | 8/1997 | Barbas et al. |
| 5,667,988 A | 9/1997 | Barbas et al. |
| 5,693,761 A | 12/1997 | Queen et al. |
| 5,693,762 A | 12/1997 | Queen et al. |
| 5,739,277 A | 4/1998 | Presta et al. |
| 5,834,250 A | 11/1998 | Wells et al. |
| 5,846,951 A | 12/1998 | Gregoriadis |
| 5,859,205 A | 1/1999 | Adair et al. |
| 5,869,046 A | 2/1999 | Presta et al. |
| 5,885,793 A | 3/1999 | Griffiths et al. |
| 6,030,613 A | 2/2000 | Blumberg et al. |
| 6,086,875 A | 7/2000 | Blumberg et al. |
| 6,096,871 A | 8/2000 | Presta et al. |
| 6,121,022 A | 9/2000 | Presta et al. |
| 6,194,551 B1 | 2/2001 | Idusogie et al. |
| 6,242,195 B1 | 6/2001 | Idusogie et al. |
| 6,251,632 B1 | 6/2001 | Lillicrap et al. |
| 6,277,375 B1 | 8/2001 | Ward |
| 6,407,213 B1 | 6/2002 | Carter et al. |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,696,245 B2 | 2/2004 | Winter et al. |
| 6,737,056 B1 | 5/2004 | Presta |
| 6,821,505 B2 | 11/2004 | Ward |
| 6,998,253 B1 | 2/2006 | Presta et al. |
| 7,083,784 B2 | 8/2006 | Dall'Acqua et al. |
| 7,317,091 B2 | 1/2008 | Lazar et al. |
| 7,404,956 B2 | 7/2008 | Peters et al. |
| 8,329,182 B2 | 12/2012 | Peters et al. |
| 10,611,794 B2 | 4/2020 | Bolton et al. |
| 11,578,098 B2 | 2/2023 | Bolton et al. |
| 2003/0069395 A1 | 4/2003 | Sato et al. |
| 2003/0235536 A1 | 12/2003 | Blumberg et al. |
| 2005/0079574 A1 | 4/2005 | Bond |
| 2007/0191597 A1 | 8/2007 | Sanjay et al. |
| 2007/0237765 A1 | 9/2007 | Lazar et al. |
| 2007/0237766 A1 | 9/2007 | Lazar et al. |
| 2007/0237767 A1 | 9/2007 | Lazar et al. |
| 2007/0243188 A1 | 9/2007 | Lazar et al. |
| 2007/0248603 A1 | 9/2007 | Lazar et al. |
| 2007/0231329 A1 | 10/2007 | Lazar et al. |
| 2007/0286859 A1 | 12/2007 | Lazar et al. |
| 2008/0004206 A1 | 1/2008 | Rosen et al. |
| 2008/0057056 A1 | 5/2008 | Lazar et al. |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0261877 A1 | 10/2008 | Ballance et al. |
| 2009/0247735 A1 | 10/2009 | Gagnon |
| 2010/0292130 A1 | 11/2010 | Skerra et al. |
| 2011/0046060 A1* | 2/2011 | Schellenberger .... C07K 14/001 530/381 |
| 2011/0190194 A1* | 8/2011 | Lim .................... A61P 43/00 530/380 |
| 2012/0015424 A1 | 1/2012 | Selvitelli et al. |
| 2013/0108629 A1 | 5/2013 | Dumont et al. |
| 2013/0202595 A1 | 8/2013 | Pierce et al. |
| 2016/0347788 A1 | 12/2016 | Bolton et al. |
| 2020/0283474 A1 | 9/2020 | Bolton et al. |

FOREIGN PATENT DOCUMENTS

| | | |
|---|---|---|
| EP | 3903599 A1 | 11/2021 |
| WO | WO 1988/007089 A1 | 9/1988 |
| WO | WO 1990/002809 A1 | 3/1990 |
| WO | WO 1991/017271 A1 | 11/1991 |
| WO | WO 1992/001047 A1 | 1/1992 |
| WO | WO 1992/009690 A2 | 6/1992 |
| WO | WO 1992/015679 A1 | 9/1992 |
| WO | WO 1992/018619 A1 | 10/1992 |
| WO | WO 1992/020791 A1 | 11/1992 |
| WO | WO 1993/001288 A1 | 1/1993 |
| WO | WO 1996/014339 A1 | 5/1996 |
| WO | WO 1998/005787 A1 | 2/1998 |
| WO | WO 1998/023289 A1 | 6/1998 |
| WO | WO 1999/051642 A1 | 10/1999 |
| WO | WO 1999/058572 A1 | 11/1999 |
| WO | WO 2000/009560 A2 | 2/2000 |
| WO | WO 2000/032767 A1 | 6/2000 |
| WO | WO 2000/042072 A2 | 7/2000 |
| WO | WO 2001/087922 A2 | 11/2001 |
| WO | WO 2002/044215 A2 | 6/2002 |
| WO | WO 2002/060919 A2 | 8/2002 |
| WO | WO 2003/020764 A2 | 3/2003 |
| WO | WO 2003/074569 A2 | 9/2003 |
| WO | WO 2003/077834 A2 | 9/2003 |
| WO | WO 2002/040544 A3 | 10/2003 |
| WO | WO 2004/016750 A2 | 2/2004 |
| WO | WO 2004/029207 A2 | 4/2004 |
| WO | WO 2004/035752 A2 | 4/2004 |
| WO | WO 2004/044859 A1 | 5/2004 |
| WO | WO 2004/063351 A2 | 7/2004 |
| WO | WO 2004/074455 A2 | 9/2004 |
| WO | WO 2004/099249 A2 | 11/2004 |
| WO | WO 2004/101740 A2 | 11/2004 |
| WO | WO 2005/040217 A2 | 5/2005 |
| WO | WO 2005/070963 A1 | 8/2005 |
| WO | WO 2005/077981 A2 | 8/2005 |
| WO | WO 2005/092925 A2 | 10/2005 |
| WO | WO 2005/123780 A2 | 12/2005 |
| WO | WO 2006/019447 A1 | 2/2006 |
| WO | WO 2006/047350 A2 | 5/2006 |
| WO | WO 2006/074199 A1 | 7/2006 |
| WO | WO 2006/085967 A2 | 8/2006 |
| WO | WO 2007/021494 A2 | 2/2007 |
| WO | WO 2007/149406 A2 | 12/2007 |
| WO | WO 2008/033413 A2 | 3/2008 |
| WO | WO 2008/118507 A2 | 10/2008 |
| WO | WO 2008/155134 A1 | 12/2008 |
| WO | WO 2009/051717 A2 | 4/2009 |
| WO | WO 2009/058322 A1 | 5/2009 |
| WO | WO 2009/130198 A2 | 10/2009 |
| WO | WO 2009/137254 A2 | 11/2009 |
| WO | WO 2009/140015 A2 | 11/2009 |
| WO | WO 2009/154695 A1 | 12/2009 |
| WO | WO 2011/069164 A2 | 6/2011 |
| WO | WO 2012/006623 A1 | 1/2012 |
| WO | WO 2012/006624 A2 | 1/2012 |
| WO | WO 2012/006633 A1 | 1/2012 |
| WO | WO 2012/006635 A1 | 1/2012 |
| WO | WO 2012/014183 A1 | 2/2012 |
| WO | WO 2013/106787 A1 | 7/2013 |
| WO | WO 2013/123457 A1 | 8/2013 |
| WO | WO 2015/048330 A2 | 4/2015 |
| WO | WO 2015/048330 A3 | 10/2015 |

OTHER PUBLICATIONS

Brorson et al., (May 2003) "Bracketed Generic Inactivation of Rodent Retroviruses by Low pH Treatment for Monoclonal Antibodies and Recombinant Proteins", Biotechnol Bioeng. 5;82(3) pp. 321/329. doi: 10.1002/bit. 10574.

Burmeister, et al. (Nov. 24, 1994) "Crystal Structure of The Complex of Rat Neonatal Fc Receptor With Fc," Nature, vol. 372, pp. 379-383.

Caliceti, et al. (Jul. 1999) "Biopharmaceutical properties of uricase conjugated to neutral and amphiphilic polymers." Bioconjugate chemistry, vol. 10, No. 4, pp. 638/46.

(56) References Cited

OTHER PUBLICATIONS

Cameron, et al. (Feb. 1998) "The canine factor VIII cDNA and 5' flanking sequence." Thrombosis and haemostasis, vol. 79, No. 2, pp. 317/22.
Capon, et al. (Feb. 1989) "Designing CD4 immunoadhesins for AIDS therapy." Nature, vol. 337, No. 6207, pp. 525/31.
Cutler, et al. (Mar. 2002) "The identification and classification of 41 novel mutations in the factor VIII gene (F8C)." Human mutation, vol. 19, No. 3, pp. 274/8.
Davies et al. (Jun. 1996) "Single antibody domains as small recognition units: design and in vitro antigen selection of camelized, human VH domains with improved protein stability." Protein engineering, vol. 9, No. 6 pp. 531/7.
De Vries, et al. (Feb. 21, 1992) "The fms/like tyrosine kinase, a receptor for vascular endothelial growth factor." Science (New York, N.Y.) vol. 255, No. 5047, pp. 989/91.
Dennis, et al. (Sep. 20, 2002) "Albumin binding as a general strategy for improving the pharmacokinetics of proteins." The Journal of biological chemistry, vol. 277, No. 38, pp. 35035/43.
Extended European Search Report for European Patent Application No. 21161387.2, mailed on Sep. 23, 2021.
Extended European Search Report received for European Patent Application No. 14849291.1, mailed on Jul. 4, 2017, 12 pages.
Genbank, "*Homo sapiens* Transferrin (TF), mRNA," Accession No. NM001063.3 published on May 25, 2014, accessed at http://www.ncbi.nlm.nih.gov/nuccore/NM_001063, accessed on Sep. 24, 2014, 5 pages.
Genbank, "*Homo sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.
Genbank, "*Homo sapiens* Transferrin (TF), mRNA," Accession No. XM039847 published on Jul. 16, 2001, accessed at http://www.ncbi.nim.nih.gov/nuccore/XM_039847.1?report=genbank, accessed on Sep. 24, 2014, 2 pages.
Genbank, "*Homo sapiens* Transferrin (TF), mRNA," Accession No. XM039845 published Jul. 16, 2001, accessed at https://www.ncbi.nlm.nih.gov/nuccore/XM_039845.1?report=genbank, accessed on Sep. 24, 2014, 2 pages.
Genbank, "Human Transferrin mRNA, Complete cds," Accession No. M12530.1, published on Jan. 14, 1995, accessed at http://www.ncbi.nlm.nih.gov/nuccore/M1253014, accessed on Jan. 15, 2015, 2 pages.
GenBank, "Transferrin [human, liver, mRNA, 2347 nt]," Accession No. S95936.1, published on May 7, 1993, accessed at http://www.ncbi.nlm.nih.gov/nuccore/595936, accessed on Sep. 24, 2014, 2 pages.
Genbank, "transferrin precursor [*Homo sapiens*]" Accession AAA61140.1, accessed at http://www.ncbi.nlm.nih.gov/protein/AAA61140, Mar. 29, 2016, 3 pages.
Graham, et al. (Jul. 1, 1997) "Characteristics of a human cell line transformed by DNA from human adenovirus type 5." The Journal of general virology, vol. 36, No. 1, pp. 59/74.
International Search Report and Written Opinion received for PCT Patent Application No. PCT/US2014/057524, mailed on Mar. 23, 2015, 13 pages.
Josić, et al. (Jul. 4, 1997) "Issues in the development of medical products based on human plasma." Journal of chromatography. B, Biomedical sciences and applications, vol. 694, No. 2, pp. 253/69.
Juo Pei/Show (2002), The Concise Dictionary of Biomedicine and Molecular Biology, 2nd Edition, CRC Press, United States.
König et al. (Sep. 1, 1998) "Use of an albumin/binding domain for the selective immobilisation of recombinant capture antibody fragments on ELISA plates." Journal of immunological methods, vol. 218, Nos. 1/2, pp. 73/83.
Liu et al., (Sep./Oct. 2010) "Recovery and purification process development for monoclonal antibody production", MAbs. 2(5) pp. 480-499. doi: 10.4161/mabs.2.5.12645.

Mather (Sep. 1980) "Establishment and characterization of two distinct mouse testicular epithelial cell lines." Biology of reproduction, vol. 23, No. 1, pp. 243/52.
Mather, et al. (Jun. 1982) "Culture of testicular cells in hormone/supplemented serum/free medium." Annals of the New York Academy of Sciences, vol. 383, pp. 44/68.
Milstein et al. (Oct. 1983) "Hybrid hybridomas and their use in immunohistochemistry." Nature, vol. 305, No. 5934 pp. 537/40.
Morpurgo, et al. (Jan. 1996) "Covalent modification of mushroom tyrosinase with different amphiphic polymers for pharmaceutical and biocatalysis applications." Applied biochemistry and biotechnology, vol. 56, No. 1, pp. 59/72.
Morrison (1985) "Transfectomas provide novel chimeric antibodies." Science (New York, N.Y.), vol. 229 No. 4719, pp. 1202/7.
Mustonen et al. (May 2, 1995) "Endothelial receptor tyrosine kinases involved in angiogenesis." The Journal of cell biology, vol. 129, No. 4, pp. 895/8.
Oi et al., (May/Jun. 1986). "Chimeric Antibodies," BioTechniques, vol. 4, pp. 214/221.
Persson, et al. (Jun. 1, 2001) "Substitution of valine for leucine 305 in factor Vlla increases the intrinsic enzymatic activity." The Journal of biological chemistry, vol. 276, No. 31, pp. 29195/9.
Persson, et al. (Nov. 2001) "Rational design of coagulation factor Vlla variants with substantially increased intrinsic activity." Proceedings of the National Academy of Sciences of the United States of America, vol. 98, No. 24, pp. 13583/8.
Petrovan et al. (Nov. 14, 2001) "Residue Met (156) contributes to the labile enzyme conformation of coagulation factor Vlla." The Journal of biological chemistry, vol. 276, No. 9, pp. 6616/20.
Roberts et al. (Oct. 2007) "Virus inactivation by protein denaturants used in affinity chromatography." Biologicals: journal of the International Association of Biological Standardization, vol. 35, No. 4, pp. 343/7.
Roth, et al. (1993) Expression of polysialic acid in human tumors and its significance for tumor growth. In: Roth J, Rutishauser U, Troy FA II (eds) Polysialic acid: from microbes to man. Birkhäuser, Basel Boston Berlin, pp. 335-348.
Sambrook et al. (1989) Molecular cloning. A laboratory manual. 3rd edition, Cold Spring Harbor Laboratory Press, Cold Spring Harbor, New York.
Sato, et al. (Jul. 6, 1995) "Distinct roles of the receptor tyrosine kinases Tie/1 and Tie/2 in blood vessel formation." Nature, vol. 376, No. 6535, pp. 70/4.
Schlapschy, et al. (Jun. 1, 2007) "Fusion of a recombinant antibody fragment with a homo/amino/acid polymer: effects on biophysical properties and prolonged plasma half/life." Protein engineering, design & selection: PEDS, vol. 20, No. 6, pp. 273/84.
Shibuya, et al. (Apr. 1, 1990) "Nucleotide sequence and expression of a novel human receptor/type tyrosine kinase gene (flt) closely related to the fms family." Oncogene, vol. 5, No. 4, pp. 519/24.
Smith (Jun. 14, 1985) "Filamentous fusion phage: novel expression vectors that display cloned antigens on the virion surface." Science (New York, N.Y.), vol. 228, No., 4705, pp. 1315/7.
Soejima, et al. (Dec. 13, 2002) "The 99 and 170 loop/modified factor Vlla mutants show enhanced catalytic activity without tissue factor." The Journal of biological chemistry, vol. 277, No. 50, pp. 49027/35.
Soejima, et al. (May 1, 2001) "Factor Vlla modified in the 170 loop shows enhanced catalytic activity but does not change the zymogen/like property." The Journal of biological chemistry, vol. 276, No. 20, pp. 17229/35.
Sommermeyer, et al. (1987) "Klinisch verwendete Hydroxyethylstärke: Physikalisch/chemische Charakterisierung." Krankenhauspharmazie, vol. 8, pp. 271/278.
Stadler, et al. (Dec. 1, 2006) "Characterisation of a novel high/purity, double virus inactivated von Willebrand Factor and Factor VIII concentrate (Wilate)." Biologicals: journal of the International Association of Biological Standardization, vol. 34, No. 4, pp. 281/8.
Story, et al. (Dec. 1, 1994) "A major histocompatibility complex class I/like Fc receptor cloned from human placenta: possible role in transfer of immunoglobulin G from mother to fetus." The Journal of experimental medicine, vol. 180, No. 6 pp. 2377/81.

(56) References Cited

OTHER PUBLICATIONS

Terman, et al. (Sep. 1, 1991) "Identification of a new endothelial cell growth factor receptor tyrosine kinase." *Oncogene*, vol. 6, No. 9, pp. 1677/83.
Ullrich et al. (Apr. 20, 1990) "Signal transduction by receptors with tyrosine kinase activity." *Cell* vol. 61, No. 2, pp. 203/12.
Urlaub et al. (Jul. 1980) "Isolation of Chinese hamster cell mutants deficient in dihydrofolate reductase activity." *Proceedings of the National Academy of Sciences of the United States of America*, vol. 77, No. 7, pp. 4216/20.
Vorobjev, et al. (Nov./Dec. 1999) "Oligonucleotide conjugated to linear and branched high molecular weight polyethylene glycol as substrates for RNase H." *Nucleosides & nucleotides*, vol. 18, No. 11/12 pp. 2745/50.
Weidler, et al. (May 1991) "Pharmakokinetische Merkmale als Kriterien für den klinischen Einsatz von Hydroxyethylstärke" [Pharmacokinetic parameters as criteria for clinical use of hydroxyethyl starch preparations]. *Arzneimittel/Forschung*, vol. 41, No. 5, pp. 494/8.
Yarden et al. (Jul. 1988) "Growth factor receptor tyrosine kinases." *Annual review of biochemistry*, vol. 57 pp. 443/78.
Zhang, et al. (Jan. 2014) "Quality by design approach for viral clearance by protein a chromatography." *Biotechnology and bioengineering*, vol. 111, No. 1, pp. 95/103.

\* cited by examiner

SEQUENCE LISTING

```
Sequence total quantity: 23
SEQ ID NO: 1            moltype = DNA  length = 5052
FEATURE                 Location/Qualifiers
misc_feature            1..5052
                        note = B-Domain Deleted FVIII-Fc Chain
sig_peptide             1..57
                        note = FVIII signal peptide
misc_feature            4372..5052
                        note = Fc region
source                  1..5052
                        mol_type = other DNA
                        organism = synthetic construct
SEQUENCE: 1
atgcaaatag agctctccac ctgcttcttt ctgtgccttt tgcgattctg ctttagtgcc   60
accagaagat actacctggg tgcagtggaa ctgtcatggg actatatgca agtgatctc   120
ggtgagctgc ctgtggacgc aagatttcct cctagagtgc caaaatcttt tccattcaac  180
acctcagtcg tgtacaaaaa gactctgttt gtagaattca cggatcacct tttcaacatc  240
gctaagccaa ggccaccctg gatgggtctg ctaggtccta ccatccaggc tgaggtttat  300
gatacagtgg tcattacact taagaacatg gcttcccatc ctgtcagtct tcatgctgtt  360
ggtgtatcct actggaaagc ttctgaggga gctgaatatg atgatcagac cagtcaaagg  420
gagaagaag atgataaagt cttccctggt ggaagccata catatgtctg gcaggtcctg  480
aaagagaatg gtccaatggc ctctgaccca ctgtgcctta cctactcata tctttctcat  540
gtggacctgg taaagacttt gaattcaggc ctcattggag ccctactagt atgtagaaga  600
gggagtctgg ccaaggaaaa gacacagacc ttgcacaaat ttatactact ttttgctgta  660
tttgatgaag ggaaaagttg gcactcagaa acaaagaact ccttgatgca ggatagggat  720
gctgcatctg ctcgggcctg gcctaaaatg cacacagtca atggttatgt aaacaggtct  780
ctgccaggtc tgattggatg ccacaggaaa tcagtctatt ggcatgtgat tggaatgggc  840
accactcctg aagtgcactc aatattcctc gaaggtcaca catttcttgt gaggaaccat  900
cgccaggcgt ccttggaaat ctcgccaata actttcctta ctgctcaaac actcttgatg  960
gaccttggac agtttctact gttttgtcat atctcttccc accaacatga tggcatgaa   1020
gcttatgtca agtagacag ctgtccagag aaccccaac tacgaatgaa aataataaa   1080
gaagcggaag actatgatga tgatcttact gattctgaaa tggatgtggt caggtttgat  1140
gatgacaact ctccttcctt tatccaaatt cgcagcgtgg ccaagaagca tcctaaaact  1200
tgggtacatt acattgctgc tgaagaggag gactgggact atgctccctt agtcctcgcc  1260
cccgatgaca aagttataa aagtcaatat ttgaacaatg gccctcagcg gattggtagg  1320
aagtacaaaa agtccgatt tatggcatac acagatgaaa cctttaagac tcgtgaagct  1380
attcagcatg aatcaggaat cttgggacct ttactttatg gggaagttgg agacacactg  1440
```

```
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg cactactggt cattctaagc   1980
attggagcac agactgactt ccttctgtct tcttctctg gatataccct caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc atcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt ttttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg gatgagcac acttttctgt   3420
gtgtacagca ataagtgtca gactcccctg ggaatggctc tggacacat tagagatttt   3480
cagattacag cttcaggaca atatggacag tgggcccaa agctggccag acttcattat   3540
tccggatcaa tcaatgcctg gagcaccaag gagcccttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggaa atgtggattc atctgggata   3780
aaacacaata ttttttaaccc tccaattatt gctcgataca tccgtttgca cccaactcat   3840
tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga aagtcacagg agtaactact cagggagtaa aatctctgct taccagcatg   4140
tatgtgaagg agttcctcat ctccagcagt caagatggcc atcagtggac tctcttttt   4200
cagaatggca aagtaaaggt ttttcaggga aatcaagact ccttcacacc tgtggtgaac   4260
tctctagacc caccgttact gactcgctac cttcgaattc accccagag ttgggtgcac   4320
cagattgccc tgaggatgga ggttctgggc tgcgaggcac aggacctcta cgacaaaact   4380
cacacatgcc caccgtgccc agctccgaaa ctcctgggcg gaccgtcagt cttcctcttc   4440
ccccaaaac ccaaggacac cctcatgatc tcccggaccc ctgaggtcac atgcgtggtg   4500
gtggacgtga gccacgaaga ccctgaggtc aagttcaact ggtacgtgga cggcgtggag   4560
gtgcataatg ccaagacaaa gccgcgggag gagcagtaca acagcacgta ccgtgtggtc   4620
agcgtcctca ccgtcctgca ccaggactgg ctgaatggca aggagtacaa gtgcaaggtc   4680
tccaacaaag ccctcccagc ccccatcgag aaaaccatct ccaaagccaa agggcagccc   4740
cgagaaccac aggtgtacac cctgccccca tcccgggatg agctgaccaa gaaccaggtc   4800
agcctgacct gcctggtcaa aggcttctat cccagcgaca tcgccgtgga gtgggagagc   4860
aatgggcagc cggagaacaa ctacaagacc acgcctcccg tgttggactc cgacggctcc   4920
ttcttcctct acagcaagct caccgtggac aagagcaggt ggcagcaggg gaacgtcttc   4980
tcatgctccg tgatgcatga ggctctgcac aaccactaca cgcagaagag cctctccctg   5040
tctccgggta aa                                                        5052

SEQ ID NO: 2         moltype = AA  length = 1684
FEATURE              Location/Qualifiers
REGION               1..1684
                     note = B domain deleted FVIII-Fc chain
SIGNAL               1..19
                     note = signal sequence
REGION               20..759
                     note = MISC_FEATURE - HC sequence
REGION               760..773
                     note = MISC_FEATURE - remaining B Domain sequence
REGION               1458..1684
                     note = MISC_FEATURE - Fc sequence
source               1..1684
                     mol_type = protein
                     organism = synthetic construct
SEQUENCE: 2
MQIELSTCFF LCLLRFCFSA TRRYYLGAVE LSWDYMQSDL GELPVDARFP PRVPKSFPFN   60
```

```
TSVVYKKTLF VEFTDHLFNI AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYLSH   180
VDLVKDLNSG LIGALLVCRE GSLAKEKTQT LHKFILLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPI TFLTAQTLLM DLGQFLLFCH ISSHQHDGME AYVKVDSCPE EPQLRMKNNE   360
EAEDYDDDLT DSEMDVVRFD DDNSPSFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSQNPPVLKR HQREITRTTL   780
QSDQEEIDYD DTISVEMKKE DFDIYDEDEN QSPRSFQKKT RHYFIAAVER LWDYGMSSSP   840
HVLRNRAQSG SVPQFKKVVF QEFTDGSFTQ PLYRGELNEH LGLLGPYIRA EVEDNIMVTF   900
RNQASRPYSF YSSLISYEED QRQGAEPRKN FVKPNETKTY FWKVQHHMAP TKDEFDCKAW   960
AYFSDVDLEK DVHSGLIGPL LVCHTNTLNP AHGRQVTVQE FALFFTIFDE TKSWYFTENM  1020
ERNCRAPCNI QMEDPTFKEN YRFHAINGYI MDTLPGLVMA QDQRIRWYLL SMGSNENIHS  1080
IHFSGHVFTV RKKEEYKMAL YNLYPGVFET VEMLPSKAGI WRVECLIGEH LHAGMSTLFL  1140
VYSNKCQTPL GMASGHIRDF QITASGQYGQ WAPKLARLHY SGSINAWSTK EPFSWIKVDL  1200
LAPMIIHGIK TQGARQKFSS LYISQFIIMY SLDGKKWQTY RGNSTGTLMV FFGNVDSSGI  1260
KHNIFNPPII ARYIRLHPTH YSIRSTLRME LMGCDLNSCS MPLGMESKAI SDAQITASSY  1320
FTNMFATWSP SKARLHLQGR SNAWRPQVNN PKEWLQVFDG KTMKVTGVTT QGVKSLLTSM  1380
YVKEFLISSS QDGHQWTLFF QNGKVKVFQG NQDSFTPVVN SLDPPLLTRY LRIHPQSWVH  1440
QIALRMEVLG CEAQDLYDKT HTCPPCPAPE LLGGPSVFLF PPKPKDTLMI SRTPEVTCVV  1500
VDVSHEDPEV KFNWYVDGVE VHNAKTKPRE EQYNSTYRVV SVLTVLHQDW LNGKEYKCKV  1560
SNKALPAPIE KTISKAKGQP REPQVYTLPP SRDELTKNQV SLTCLVKGFY PSDIAVEWES  1620
NGQPENNYKT TPPVLDSDGS FFLYSKLTVD KSRWQQGNVF SCSVMHEALH NHYTQKSLSL  1680
SPGK                                                              1684

SEQ ID NO: 3            moltype = DNA  length = 741
FEATURE                 Location/Qualifiers
misc_feature            1..741
                        note = Fc DNA sequence
sig_peptide             1..60
                        note = mouse Ig kappa signal peptide
source                  1..741
                        mol_type = other DNA
                        organism = synthetic construct
SEQUENCE: 3
atggagacag acacactcct gctatgggta ctgctgctct gggttccagg ttccactggt    60
gacaaaactc acacatgccc accgtgccca gcacctgaac tcctggggag accgtcagtc   120
ttcctcttcc cccaaaaacc caaggacacc ctcatgatct cccggacccc tgaggtcaca   180
tgcgtggtgg tggacgtgag ccacgaagac cctgaggtca agttcaactg gtacgtggac   240
ggcgtggagg tgcataatgc caagacaaag ccgcgggagg agcagtacaa cagcacgtac   300
cgtgtggtca gcgtcctcac cgtcctgcac caggactggc tgaatggcaa ggagtacaag   360
tgcaaggtct ccaacaaagc cctcccagcc ccatcgaga aaaccatctc aaagccaaa   420
gggcagcccc gagaaccaca ggtgtacacc ctgcccccat cccgcgatga gctgaccaag   480
aaccaggtca gcctgacctg cctggtcaaa ggcttctatc ccagcgacat cgccgtggag   540
tgggagagca atgggcagcc ggagaacaac tacaagacca cgcctcccgt gttggactcc   600
gacggctcct tcttcctcta cagcaagctc accgtggaca agagcaggtg gcagcagggg   660
aacgtcttct catgctccgt gatgcatgag gctctgcaca accactacac gcagaagagc   720
ctctccctgt ctccgggtaa a                                             741

SEQ ID NO: 4            moltype = AA  length = 247
FEATURE                 Location/Qualifiers
REGION                  1..247
                        note = B domain deleted FVIII-Fc chain
SIGNAL                  1..19
                        note = mouse Ig kappa signal peptide
source                  1..247
                        mol_type = protein
                        organism = synthetic construct
SEQUENCE: 4
METDTLLLWV LLLWVPGSTG DKTHTCPPCP APELLGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALPA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVMHE ALHNHYTQKS   240
LSLSPGK                                                             247

SEQ ID NO: 5            moltype = DNA  length = 7734
FEATURE                 Location/Qualifiers
misc_feature            1..7734
                        note = Full Length FVIII-Fc DNA Sequence
sig_peptide             1..57
                        note = FVIII signal peptide
misc_feature            7054..7734
                        note = Fc region
source                  1..7734
                        mol_type = other DNA
```

```
                 organism = synthetic construct
SEQUENCE: 5
atgcaaatag agctctccac ctgcttcttt ctgtgccttt tgcgattctg ctttagtgcc    60
accagaagat actacctggg tgcagtggaa ctgtcatggg actatatgca aagtgatctc   120
ggtgagctgc ctgtggacgc aagatttcct cctagagtgc caaaatcttt tccattcaac   180
acctcagtcg tgtacaaaaa gactctgttt gtagaattca cggatcacct tttcaacatc   240
gctaagccaa ggccaccctg gatgggtctg ctaggtccta ccatccaggc tgaggtttat   300
gatacagtgg tcattacact taagaacatg gcttcccatc ctgtcagtct tcatgctgtt   360
ggtgtatcct actggaaagc ttctgaggga gctgaatatg atgatcagac cagtcaaagg   420
gagaaagaag atgataaagt cttccctggt ggaagccata catatgtctg gcaggtcctg   480
aaagagaatg gtccaatggc ctctgaccca ctgtgcctta cctactcata tctttctcat   540
gtggacctga taaagactt gaattcaggc ctcattggag ccctactagt atgtagagaa   600
gggagtctgg ccaaggaaaa gacacagacc ttgcacaaat ttatactact ttttgctgta   660
tttgatgaag ggaaaagttg gcactcagaa acaaagaact ccttgatgca ggatagggat   720
gctgcatctg ctcgggcctg gcctaaaatg cacacagtca atggttatgt aaacaggtct   780
ctgccaggtc tgattggatg ccacaggaaa tcagtctatt ggcatgtgat tggaatgggc   840
accactcctg aagtgcactc aatattcctc gaaggtcaca catttcttgt gaggaaccat   900
cgccaggcgt ccttggaaat ctcgccaata acttccttca ctgctcaaac actcttgatg   960
gaccttggac agtttctact gttttgtcat atctcttccc accaacatga tggcatggaa  1020
gcttatgtca agtagacag ctgtccagag aaccccaac tacgaatgaa aaataatgaa  1080
gaagcggaag actatgatga tgatcttact gattctgaaa tggatgtggt caggtttgat  1140
gatgcaaact ctccttcctt tatccaaatt cgctcagttg ccaagaagca tcctaaaact  1200
tgggtacatt acattgctgc tgaagaggag gactggact atgctccctt agtcctcgcc  1260
cccgatgaca gaagttataa aagtcaatat ttgaacaatg ccctcagcg gattggtagg  1320
aagtacaaaa aagtccgatt tatggcatac acagatgaaa cctttaagac tcgtgaagct  1380
attcagcatg aatcaggaat cttgggacct ttacttttatg gggaagttgg agacacactg  1440
ttgattatat ttaagaatca agcaagcaga ccatataaca tctaccctca cggaatcact  1500
gatgtccgtc ctttgtattc aaggagatta ccaaaaggtg taaaacattt gaaggatttt  1560
ccaattctgc caggagaaat attcaaatat aaatggacag tgactgtaga agatgggcca  1620
actaaatcag atcctcggtg cctgacccgc tattactcta gtttcgttaa tatggagaga  1680
gatctagctt caggactcat tggccctctc ctcatctgct acaagaatc tgtagatcaa  1740
agaggaaacc agataatgtc agacaagagg aatgtcatcc tgttttctgt atttgatgag  1800
aaccgaagct ggtacctcac agagaatata caacgctttc tccccaatcc agctggagtg  1860
cagcttgagg atccagagtt ccaagcctcc aacatcatgc acagcatcaa tggctatgtt  1920
tttgatagtt tgcagttgtc agtttgtttg catgaggtgg catactggta cattctaagc  1980
attggagcac agactgactt cctttctgtc ttcttctctg gatataccct caaacacaaa  2040
atggtctatg aagacacact caccctattc ccattctcag gagaaactgt cttcatgtcg  2100
atggaaaacc caggtctatg gattctgggg tgccacaact cagactttcg gaacagaggc  2160
atgaccgcct tactgaaggt ttctagttgt gacaagaaca ctggtgatta ttacgaggac  2220
agttatgaag atatttcagc atacttgctg agtaaaaaca atgccattga accaagaagc  2280
ttctcccaga attcaagaca ccctagcact aggcaaaagc aatttaatgc caccacaatt  2340
ccagaaaatg acatagagaa gactgaccct tggtttgcac acagaacacc tatgcctaaa  2400
atacaaaatg tctcctctag tgatttgttg atgctcttgc gacagagtcc tactcccacat  2460
gggctatcct tatctgatct ccaagaagcc aaatatgaga ctttttctga tgatccatca  2520
cctggagcaa tagacagtaa taacagcctg tctgaaatga cacacttcag gccacagctc  2580
catcacagtg gggacatggt atttacccct gagtcaggcc tccaattaag attaaatgag  2640
aaactgggga caactgcagc aacagagttg aagaaacttg atttcaaagt ttctagtaca  2700
tcaaataatc tgatttcaac aattccatca gacaatttgg cagcaggtac tgataataca  2760
agttccttag accccaag tatgccagtt cattatgata gtcaattaga taccactcta  2820
tttggcaaaa agtcatctcc ccttactgag tctggtggac ctctgagctt gagtgaagaa  2880
aataatgatt caaagttgtt agaatcaggt ttaatgaata gccaagaaag ttcatgggga  2940
aaaaatgtat cgtcaacaga gagtggtagg ttatttaaag ggaaaagagc tcatggacct  3000
gctttgttga ctaaagataa tgccttattc aaagttagca tctctttgtt aaagacaaac  3060
aaaacttcca ataattcagc aactaataga agactcaca ttgatggccc atcattatta  3120
attgagaata gtccatcagt ctggcaaaat atattagaaa gtgacactga gtttaaaaaa  3180
gtgacaccttt tgattcatga cagaatgctt atggacaaaa atgctacagc tttgaggcta  3240
aatcatatgt caaataaaac tacttcatca aaaaacatgg aaatggtcca acagaaaaaa  3300
gagggccca ttccaccaga tgcacaaaat ccagatatgt cgttctttaa gatgctattc  3360
ttgccagaat cagcaaggtg gatacaaagg actcatgaaa agaactctct gaactctggg  3420
caaggcccca gtccaaagca attagtatcc ttaggaccag aaaaatctgt ggaaggtcag  3480
aatttcttgt ctgagaaaaa caagtggta gtaggaaagg gtgaatttac aaaggacgta  3540
ggactcaaag agatggtttt tccaagcagc agaaacctat ttcttactaa cttggataat  3600
ttacatgaaa ataatacaca caatcaagaa aaaaaaattc aggaagaaat agaaagaag  3660
gaaacattaa tccaagagaa tgtagttttg cctcagataa atacagtgac tggcactaag  3720
aatttcatga gaaccttttt cttactgagc actaggcaaa atgtagaagg ttcatatgac  3780
ggggcatatg ctccagtact tcaagatttt aggtcattaa atgattcaac aaatagaaca  3840
aagaaacaca cagctcattt ctcaaaaaaa ggggaggaag aaaacttgga aggcttggga  3900
aatcaaacca gcaaattgt agagaaatat gcatgcacca aaggatatc tcctaataca  3960
agccagcaga atttttgtcac gcaacgtagt aagagagctt tgaaacaatt cagactccca  4020
ctagaagaaa cagaacttga aaaaaggata attgtggatg acacctcaac ccagtggtcc  4080
aaaaacatga acatttgac cccgagcacc ctcacacaga tagactacaa tgagaaggag  4140
aaaggggcca ttactcagtc tcccttatca gattgcctta cgaggagtca tagcatccct  4200
caagcaaata gatctccatt acccattgca aaggtatcat catttccatc tattagacct  4260
atatatctga ccagggtcct attccaagac aactctttca agcatcttat  4320
agaaagaaag attctggggt ccaagaaagc agtcatttct tacaaggagc caaaaaaat  4380
aacctttctt tagccattct aaccttggag atgactggtg atcaaagaga ggttggctcc  4440
ctggggacaa gtgccacaaa ttcagtcaca tacaagaaag ttgagaacac tgttctcccg  4500
aaaccagact tgcccaaaac atctggcaaa gttgaattgc ttccaaaagt tcacatttat  4560
cagaaggacc tattccctac ggaaactagc aatgggtctc ctggccatct ggatctcgtg  4620
```

```
gaagggagcc ttcttcaggg aacagaggga gcgattaagt ggaatgaagc aaacagacct 4680
ggaaaagttc cctttctgag agtagcaaca gaaagctctg caaagactcc ctccaagcta 4740
ttggatcctc ttgcttggga taaccactat ggtactcaga taccaaaaga agagtggaaa 4800
tcccaagaga agtcaccaga aaaaacagct tttaagaaaa aggataccat tttgtccctg 4860
aacgcttgtg aaagcaatca tgcaatagca gcaataaatg agggacaaaa taagcccgaa 4920
atagaagtca cctgggcaaa gcaaggtagg actgaaaggc tgtgctctca aaacccacca 4980
gtcttgaaac gccatcaacg ggaaataact cgtactactc ttcagtcaga tcaagaggaa 5040
attgactatg atgataccat atcagttgaa atgaagaagg aagattttga catttatgat 5100
gaggatgaaa atcagagccc ccgcagcttt caaaagaaaa cacgacacta ttttattgat 5160
gcagtggaga ggctctggga ttatgggatg agtagctccc cacatgttct aagaaacagg 5220
gctcagagtg gcagtgtccc tcagttcaag aaagttgttt tccaggaatt tactgatggc 5280
tcctttactc agcccttata ccgtggagaa ctaaatgaac attttgggact cctgggccca 5340
tatataagag cagaagttga agataatatc atggtaactt tcagaaatca ggcctctcgt 5400
ccctattcct tctattctag ccttattcct tatgaggaag atcagaggca aggagcagaa 5460
cctagaaaaa actttgtcaa gcctaatgaa accaaaactt acttttggaa agtgcaacat 5520
catatggcac ccactaaaga tgagtttgac tgcaaagcct gggcttattt ctctgatgtt 5580
gacctggaaa agatgtgcta ctcaggcctg attggacccc ttctggtctg ccacactaac 5640
acactgaacc ctgctcatgg gagacaagta acagtacagg aatttgctct gttttcacc 5700
atctttgatg agaccaaaag ctggtacttc actgaaaata tggaaagaaa ctgcagggct 5760
ccctgcaata tccagatgga agatcccact tttaaagaga attatcgctt ccatgcaatc 5820
aatggctaca taatggatac actacctggc ttagtaatgg ctcaggatca aaggattcga 5880
tggtatctgc tcagcatggg cagcaatgaa aacatccatt ctattcattt cagtggacat 5940
gtgttcactg tacgaaaaaa agaggagtat aaaatggcac tgtacaatct ctatccaggt 6000
gttttttgaga cagtggaaat gttaccatcc aaagctggaa tttggcgggt ggaatgcctt 6060
attggcgagc atctacatgc tgggatgagc acacttttc tggtgtacag caataagtgt 6120
cagactcccc tgggaatggc ttctggacac attagaggga ttcagattac agctctcagga 6180
caatatggac agtgggcccc aaagctggcc agacttcatt attccggatc aatcaatgcc 6240
tggagcacca aggagccctt ttcttggatc aaggtggatc tgttggcacc aatgattatt 6300
cacggcatca agacccaggg tgcccgtcag aagttctcca gcctctacat ctctcagttt 6360
atcatcatgt atagtcttga tgggaagaag tggcagactt atcgaggaaa ttccactgga 6420
accttaatgg tcttctttgg caatgtggat tcatctggga taaaacacaa tatttttaac 6480
cctccaatta ttgctcgata catccgtttg cacccaactc attatagcat tcgcagcact 6540
cttcgcatgg agttgatggg ctgtgattta aatagttgca gcatgccatt gggaatggag 6600
agtaaagcaa tatcagatgc acagattact gcttcatcat actttaccaa tatgtttgcc 6660
acctggtctc cttcaaagc tcgacttcac ctccaaggga ggagtaatgc ctggagacct 6720
caggtgaata atccaaaaga gtggctgcaa gtggacttcc agaagacaat gaaagtcaca 6780
ggagtaacta ctcagggagt aaaatctctg cttaccagca tgtatgtgaa ggagttcctc 6840
atctccagca gtcaagatgg ccatcagtgg actctctttt ttcagaatgg caaagtaaag 6900
gttttttcagg gaaatcaaga ctccttcaca cctgtggtga actctctaga acctccgtta 6960
ctgactcgct accttcgaat tcaccccag agttgggtgc accagattgc cctgaggatg 7020
gaggttctgg gctgcgaggc acaggacctc tacgacaaaa ctcacacatg cccaccgtgc 7080
ccagctccag aactcctggg cggaccgtca gtcttcctct tccccccaaa acccaaggac 7140
accctcatga tctcccggac ccctgaggtc acatgcgtgg tggtggacgt gagccacgaa 7200
gaccctgagg tcaagttcaa ctggtacgtg gacggcgtgg aggtgcataa tgccaagaca 7260
aagccgcggg aggagcagta caacagcacg taccgtgtgg tcagcgtcct caccgtcctg 7320
caccaggact ggctgaatgg caaggagtac aagtgcaagg tctccaacaa agccctccca 7380
gcccccatcg agaaaaccat ctccaaagcc aaagggcagc cccgagaacc acaggtgtac 7440
accctgcccc catcccggga tgagctgacc aagaaccagg tcagcctgac ctgcctggtc 7500
aaaggcttct atcccagcga catcgccgtg gagtgggaga gcaatgggca gccggagaac 7560
aactacaaga ccacgcctcc cgtgttggac tccgacggct ccttcttcct ctacagcaag 7620
ctcaccgtgg acaagagcag gtggcagcag gggaacgtct tctcatgctc cgtgatgcat 7680
gaggctctgc acaaccacta cacgcagaag agcctctccc tgtctccggg taaa 7734

SEQ ID NO: 6          moltype = AA  length = 2578
FEATURE               Location/Qualifiers
REGION                1..2578
                      note = Full length FVIIIFc chain
SIGNAL                1..19
                      note = FVIII signal peptide
REGION                20..759
                      note = MISC_FEATURE - HC sequence
REGION                760..1667
                      note = MISC_FEATURE - B Domain sequence
REGION                2351..2578
                      note = MISC_FEATURE - Fc sequence
source                1..2578
                      mol_type = protein
                      organism = synthetic construct
SEQUENCE: 6
MQIELSTCFF LCLLRFCFSA TRRYYLGAVE LSWDYMQSDL GELPVDARFP PRVPKSFPFN   60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIGMG TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
```

```
NRSWYLTENI QRFLPNPAGV QLEDPEFQAS NIMHSINGYV FDSLQLSVCL HEVAYWYILS    660
IGAQTDFLSV FFSGYTFKHK MVYEDTLTLF PFSGETVFMS MENPGLWILG CHNSDFRNRG    720
MTALLKVSSC DKNTGDYYED SYEDISAYLL SKNNAIEPRS FSQNSRHPST RQKQFNATTI    780
PENDIEKTDP WFAHRTPMPK IQNVSSSDLL MLLRQSPTPH GLSLSDLQEA KYETFSDDPS    840
PGAIDSNNSL SEMTHFRPQL HHSGDMVFTP ESGLQLRLNE KLGTTAATEL KKLDFKVSST    900
SNNLISTIPS DNLAAGTDNT SSLGPPSMPV HYDSQLDTTL FGKKSSPLTE SGGPLSLSEE    960
NNDSKLLESG LMNSQESSWG KNVSSTESGR LFKGKRAHGP ALLTKDNALF KVSISLLKTN   1020
KTSNNSATNR KTHIDGPSLL IENSPSVWQN ILESDTEFKK VTPLIHDRML MDKNATALRL   1080
NHMSNKTTSS KNMEMVQQKK EGPIPPDAQN PDMSFFKMLF LPESARWIQR THGKNSLNSG   1140
QGPSPKQLVS LGPEKSVEGQ NFLSEKNKVV VGKGEFTKDV GLKEMVFPSS RNLFLTNLDN   1200
LHENNTHNQE KKIQEEIEKK ETLIQENVVL PQIHTVTGTK NFMKNLFLLS TRQNVEGSYD   1260
GAYAPVLQDF RSLNDSTNRT KKHTAHFSKK GEEENLEGLG NQTKQIVEKY ACTTRISPNT   1320
SQQNFVTQRS KRALKQFRLP LEETELEKRI IVDDTSTQWS KNMKHLTPST LTQIDYNEKE   1380
KGAITQSPLS DCLTRSHSIP QANRSPLPIA KVSSFPSIRP IYLTRVLFQD NSSHLPAASY   1440
RKKDSGVQES SHFLQGAKKN NLSLAILTLE MTGDQREVGS LGTSATNSVT YKKVENTVLP   1500
KPDLPKTSGK VELLPKVHIY QKDLFPTETS NGSPGHLDLV EGSLLQGTEG AIKWNEANRP   1560
GKVPFLRVAT ESSAKTPSKL LDPLAWDNHY GTQIPKEEWK SQEKSPEKTA FKKKDTILSL   1620
NACESNHAIA AINEGQNKPE IEVTWAKQGR TERLCSQNPP VLKRHQREIT RTTLQSDQEE   1680
IDYDDTISVE MKKEDFDIYD EDENQSPRSF QKKTRHYFIA AVERLWDYGM SSSPHVLRNR   1740
AQSGSVPQFK KVVFQEFTDG SFTQPLYRGE LNEHLGLLGP YIRAEVEDNI MVTFRNQASR   1800
PYSFYSSLIS YEEDQRQGAE PRKNFVKPNE TKTYFWKVQH HMAPTKDEFD CKAWAYFSDV   1860
DLEKDVHSGL IGPLLVCHTN TLNPAHGRQV TVQEFALFFT IFDETKSWYF TENMERNCRA   1920
PCNIQMEDPT FKENYRFHAI NGYIMDTLPG LVMAQDQRIR WYLLSMGSNE NIHSIHFSGH   1980
VFTVRKKEEY KMALYNLYPG VFETVEMLPS KAGIWRVECL IGEHLHAGMS TLFLVYSNKC   2040
QTPLGMASGH IRDFQITASG QYGQWAPKLA RLHYSGSINA WSTKEPFSWI KVDLLAPMII   2100
HGIKTQGARQ KFSSLYISQF IIMYSLDGKK WQTYRGNSTG TLMVFFGNVD SSGIKHNIFN   2160
PPIIARYIRL HPTHYSIRST LRMELMGCDL NSCSMPLGME SKAISDAQIT ASSYFTNMFA   2220
TWSPSKARLH LQGRSNAWRP QVNNPKEWLQ VDFQKTMKVT GVTTQGVKSL LTSMYVKEFL   2280
ISSSQDGHQW TLFFQNGKVK VFQGNQDSFT PVVNSLDPPL LTRYLRIHPQ SWVHQIALRM   2340
EVLGCEAQDL YDKTHTCPPC PAPELLGGPS VFLPPPKPKD TLMISRTPEV TCVVVDVSHE   2400
DPEVKFNWYV DGVEVHNAKT KPREEQYNST YRVVSVLTVL HQDWLNGKEY KCKVSNKALP   2460
APIEKTISKA KGQPREPQVY TLPPSRDELT KNQVSLTCLV KGFYPSDIAV EWESNGQPEN   2520
NYKTTPPVLD SDGSFFLYSK LTVDKSRWQQ GNVFSCSVMH EALHNHYTQK SLSLSPGK    2578

SEQ ID NO: 7              moltype = DNA  length = 2958
FEATURE                   Location/Qualifiers
misc_feature              1..2958
                          note = FVIII Heavy Chain (HC)-Fc DNA sequence (no linker
                           between HC and Fc)
sig_peptide               1..57
                          note = signal peptide
misc_feature              2278..2958
                          note = Fc region
source                    1..2958
                          mol_type = other DNA
                          organism = synthetic construct
SEQUENCE: 7
atgcaaatag agctctccac ctgcttcttt ctgtgccttt tgcgattctg ctttagtgcc     60
accagaagat actacctggg tgcagtggaa ctgtcatggg actatatgca aagtgatctc    120
ggtgagctgc ctgtggacgc aagatttcct cctagagtgc aaaatctttt ccattcaac    180
acctcagtcg tgtacaaaaa gactctgttt gtagaattca ctgatcacct tttcaacatc    240
gctaagccaa ggccaccctg gatgggtctg ctaggtccta ccatccaggc tgaggttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagcacat atgtctg gcaggtcctg      480
aaagagaatg gtccaatggc ctctgaccca ctgtgcctta cctactcata tctttctcat    540
gtggacctgg taaagacttt gaattcaggc tcattggagc cctactagt atgtagagaa     600
gggagtctgg ccaaggaaaa gacacagacc ttgcacaaat ttatactact ttttgctgta    660
tttgatgaag ggaaaagttg gcactcagaa acaaagaact cctgatgca ggataggat      720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttcctact gttttgtcat atctcttccc accaacatga tggcatggaa   1020
gcttatgtca agtagacag ctgtccagag gaaccccaac tacgaatgaa aataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctcccct agtcctgcc    1260
cccgatgaca gaagttataa aagtcaatat ttgaacaatg gccctcagcg gattggtagg   1320
aagtacaaaa agtccgatt tatggctac acagatgaaa cctttaagac tcgtgaagct    1380
attcagcatg aatcaggaat cttgggacct tacttatg gggaagttgg agacacactg     1440
ttgattatat taagaatca gcaagcaga ccatataaca tctaccctca cggaatcact     1500
gatgtccgtc ttttgtattc aaggagatta ccaaaggtgt aaacattt gaaggatttt     1560
ccaattctgc aggagaaat attcaaatat aaatgactgt tgctgaga agtgggcca      1620
actaaatcag atcctcggtg cctgaccgc tattactcta gtttcgttaa tatggagaga    1680
gatctagctt caggactcat tggccctctc tcatctgct acaagaatc tgtagataa     1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
```

```
tttgatagtt tgcagttgtc agtttgtttg catgaggtgg catactggta cattctaagc   1980
attggagcac agactgactt cctttctgtc ttcttctctg gatataccct caaacacaaa   2040
atggtctatg aagacacact caccctattc ccattctcag gagaaactgt cttcatgtcg   2100
atggaaaacc caggtctatg gattctgggg tgccacaact cagactttcg aacagaggc   2160
atgaccgcct tactgaaggt ttctagttgt gacaagaaca ctggtgatta ttacgaggac   2220
agttatgaag atatttcagc atacttgctg agtaaaaaca atgccattga accaagagac   2280
aaaactcaca catgcccacc gtgcccagct ccagaactcc tgggcggacc gtcagtcttc   2340
ctcttccccc caaaacccaa ggacaccctc atgatctccc ggacccctga ggtcacatgc   2400
gtggtggtgg acgtgagcca cgaagaccct gaggtcaagt tcaactggta cgtggacggc   2460
gtggaggtgc ataatgccaa gacaaagccg cgggaggagc agtacaacag cacgtaccgt   2520
gtggtcagcg tcctcaccgt cctgcaccag gactggctga atgcaaggga gtacaagtgc   2580
aaggtctcca acaaagccct cccagccccc atcgagaaaa ccatctccaa agccaaaggg   2640
cagccccgag aaccacaggt gtacaccctg cccccatccc gggatgagct gaccaagaac   2700
caggtcagcc tgacctgcct ggtcaaaggc ttctatccca gcgacatcgc cgtggagtgg   2760
gagagcaatg ggcagccgga gaacaactac aagaccacgc ctcccgtgtt ggactccgac   2820
ggctccttct tcctctacag caagctcacc gtggacaaga gcaggtggca gcaggggaac   2880
gtcttctcat gctccgtgat gcatgaggct ctgcacaacc actacacgca gaagagcctc   2940
tccctgtctc cgggtaaa                                                 2958

SEQ ID NO: 8              moltype = AA  length = 986
FEATURE                   Location/Qualifiers
REGION                    1..986
                          note = HC-Fc
SIGNAL                    1..19
                          note = signal peptide
REGION                    760..986
                          note = MISC_FEATURE - Fc sequence
source                    1..986
                          mol_type = protein
                          organism = synthetic construct
SEQUENCE: 8
MQIELSTCFF LCLLRFCFSA TRRYYLGAVE LSWDYMQSDL GELPVDARFP PRVPKSFPFN    60
TSVVYKKTLF VEFTDHLFNI AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYLSH   180
VDLVKDLNSG LIGALLVCRE GSLAKEKTQT LHKFILLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPI TFLTAQTLLM DLGQFLLFCH ISSHQHDGME AYVKVDSCPE EPQLRMKNNE   360
EAEDYDDDLT DSEMDVVRFD DDNSPSFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRD KTHTCPPCPA PELLGGPSVF   780
LFPPKPKDTL MISRTPEVTC VVVDVSHEDP EVKFNWYVDG VEVHNAKTKP REEQYNSTYR   840
VVSVLTVLHQ DWLNGKEYKC KVSNKALPAP IEKTISKAKG QPREPQVYTL PPSRDELTKN   900
QVSLTCLVKG FYPSDIAVEW ESNGQPENNY KTTPPVLDSD GSFFLYSKLT VDKSRWQQGN   960
VFSCSVMHEA LHNHYTQKSL SLSPGK                                       986

SEQ ID NO: 9              moltype = DNA  length = 2973
FEATURE                   Location/Qualifiers
misc_feature              1..2973
                          note = FVIII Heavy Chain (HC)-Fc DNA sequence (5 amino acid
                          linker between HC and Fc)
sig_peptide               1..58
                          note = signal peptide
misc_feature              2278..2292
                          note = 5 amino acid linker
misc_feature              2293..2973
                          note = Fc region
source                    1..2973
                          mol_type = other DNA
                          organism = synthetic construct
SEQUENCE: 9
atgcaaatag agctctccac ctgcttcttt ctgtgccttt tgcgattctg ctttagtgcc    60
accagaagat actacctggg tgcagtggaa ctgtcatggg actatatgca agtgatctc   120
ggtgagctgc ctgtggacgc aagatttcct cctagagtgc caaaatcttt tccattcaac   180
acctcagtcg tgtacaaaaa gactctgttt gtagaattca cggatcacct tttcaacatc   240
gctaagccaa ggccacccctg gatgggtctg ctaggtccta ccatccaagc tgaggtttat   300
gatacagtgg tcattacact taagaacatg gcttcccatc ctgtcagtct tcatgctgtt   360
ggtgtatcct actggaaagc ttctgaggga gctaatatg atgatcagac cagtcaaagg   420
gagaaagaag atgataaagt cttccctggt ggaagccata catatgtctg gcaggtcctg   480
aaagagaatg gtccaatggc ctctgaccca ctgtgcctta cctactagta tctttctcat   540
gtggacctga taaaagactt gaattcaggc ctcattggag cctactagt atgtagagaa   600
gggagtctgg ccaaggaaaa gacacagacc ttgcacaaat ttatactact ttttgctgta   660
tttgatgaag ggaaaaagttg gcactcagaa acaaagaact ccttgatgca ggataggat   720
gctgcatctg ctcgggcctg gcctaaaatg cacacagtca atggttatgt aaacaggtct   780
ctgccaggtc tgattggatg ccacaggaaa tcagtctatt ggcatgtgat tggaatgggc   840
accactcctg aagtgcactc aatattcctc gaaggtcaca catttcttgt gaggaaccat   900
```

```
cgccaggcgt ccttggaaat ctcgccaata actttcctta ctgctcaaac actcttgatg   960
gaccttggac agtttctact gttttgtcat atctcttccc accaacatga tggcatggaa  1020
gcttatgtca aagtagacag ctgtccagag aaccccaaac tacgaatgaa aaataatgaa  1080
gaagcggaag actatgatga tgatcttact gattctgaaa tggatgtggt caggtttgat  1140
gatgacaact ctccttcctt tatccaaatt cgctcagttg ccaagaagca tcctaaaact  1200
tgggtacatt acattgctgc tgaagaggag gactgggact atgctcccct agtcctcgcc  1260
cccgatgaca gaagttataa aagtcaatat ttgaacaatg gccctcagcg gattggtagg  1320
aagtacaaaa aagtccgatt tatggcatac acagatgaaa cctttaagac tcgtgaagct  1380
attcagcatg aatcaggaat cttgggacct ttacttatgg gggaagttgg agacacactg  1440
ttgattatat ttaagaatca agcaagcaga ccatataaca tctaccctca cggaatcact  1500
gatgtccgtc ctttgtattc aaggagatta ccaaaaggtg taaaacattt gaaggatttt  1560
ccaattctgc caggagaaat attcaaatat aaatggacag tgactgtaga agatgggcca  1620
actaaatcag atcctcggtg cctgacccgc tattactcta gtttcgttaa tatggagaga  1680
gatctagcct caggactcat tggccctctc ctcatctgct acaaagaatc tgtagatcaa  1740
agaggaaacc agataatgtc agacaagagg aatgtcatcc tgttttctgt atttgatgag  1800
aaccgaagct ggtacctcac agagaatata caacgctttc tccccaatcc agctggagtg  1860
cagcttgagg atccagagtt ccaagcctcc aacatcatgc acagcatcaa tggctatgtt  1920
tttgatagtt tgcagttgtc agtttgtttg catgaggtgg catactggta cattctaagc  1980
attggagcac agactgactt cctttctgtc ttcttctctg gatatacctt caaacacaaa  2040
atggtctatg aagacacact caccctattc ccattctcag gagaaactgt cttcatgtcg  2100
atggaaaacc caggtctatg gattctgggg tgccacaact cagactttcg gaacagaggc  2160
atgaccgcct tactgaaggt ttctagttgt gacaagaaca ctggtgatta ttacgaggac  2220
agttatgaag atatttcagc atacttgctg agtaaaaaca atgccattga accaagaagc  2280
ttctcccaga tgacaaaaac tcacacatgc ccaccgtgcc cagctccaga actcctgggc  2340
ggaccgtcag tcttcctctt ccccccaaaa cccaaggaca cctcatgat ctcccggacc  2400
cctgaggtca catgcgtggt ggtggacgtg agccacgaag accctgaggt caagttcaac  2460
tggtacgtgg acggcgtgga ggtgcataat gccaagacaa agccgcggga ggagcagtac  2520
aacagcacgt accgtgtggt cagcgtcctc accgtcctgc accaggactg gctgaatggc  2580
aaggagtaca agtgcaaggt ctccaacaaa gccctcccag cccccatcga gaaaaccatc  2640
tccaaagcca aagggcagcc ccgagaacca caggtgtaca ccctgccccc atcccgggat  2700
gagctgacca agaaccaggt cagcctgacc tgcctggtca aaggcttcta tcccagcgac  2760
atcgccgtgg agtgggagag caatgggcag ccggagaaca actacaagac cacgcctccc  2820
gtgttggact ccgacggctc cttcttcctc tacagcaagc tcaccgtgga caagagcagg  2880
tggcagcagg ggaacgtctt ctcatgctcc gtgatgcatg aggctctgca caaccactac  2940
acgcagaaga gcctctccct gtctccgggt aaa                                2973

SEQ ID NO: 10           moltype = AA  length = 991
FEATURE                 Location/Qualifiers
REGION                  1..991
                        note = HC+5-Fc
SIGNAL                  1..19
                        note = signal sequence
REGION                  760..764
                        note = MISC_FEATURE - 5 amino acid linker sequence from
                         the B domain of FVIII
REGION                  765..991
                        note = MISC_FEATURE - Fc sequence
source                  1..991
                        mol_type = protein
                        organism = synthetic construct
SEQUENCE: 10
MQIELSTCFF LCLLRFCFSA TRRYYLGAVE LSWDYMQSDL GELPVDARFP PRVPKSFPFN    60
TSVVYKKTLF VEFTDHLFNI AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYLSH   180
VDLVKDLNSG LIGALLVCRE GSLAKEKTQT LHKFILLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPI TFLTAQTLLM DLGQFLLFCH ISSHQHDGME AYVKVDSCPE EPQLRMKNNE   360
EAEDYDDDLT DSEMDVVRFD DDNSPSFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSQNDKTHTC PPCPAPELLG   780
GPSVFLFPPK PKDTLMISRT PEVTCVVVDV SHEDPEVKFN WYVDGVEVHN AKTKPREEQY   840
NSTYRVVSVL TVLHQDWLNG KEYKCKVSNK ALPAPIEKTI SKAKGQPREP QVYTLPPSRD   900
ELTKNQVSLT CLVKGFYPSD IAVEWESNGQ PENNYKTTPP VLDSDGSFFL YSKLTVDKSR   960
WQQGNVFSCS VMHEALHNHY TQKSLSLSPG K                                  991

SEQ ID NO: 11           moltype = DNA  length = 2793
FEATURE                 Location/Qualifiers
misc_feature            1..2793
                        note = FVIII Light Chain (LC)-Fc DNA sequence
sig_peptide             1..60
                        note = signal peptide
misc_feature            2113..2793
                        note = Fc region
source                  1..2793
                        mol_type = other DNA
```

```
                        organism = synthetic construct
SEQUENCE: 11
atggagacag acacactcct gctatgggta ctgctgctct ggttccagg ttccactggt    60
gaaataactc gtactactct tcagtcagat caagaggaaa ttgactatga tgataccata   120
tcagttgaaa tgaagaagga agattttgac atttatgatg aggatgaaaa tcagagcccc   180
cgcagctttc aaaagaaaac acgacactat tttattgctg cagtggagag gctctgggat   240
tatgggatga gtagctcccc acatgttcta agaaacaggg ctcagagtgg cagtgtccct   300
cagttcaaga aagttgtttt ccaggaattt actgatggct cctttactca gcccttatac   360
cgtggagaac taaatgaaca tttgggactc ctggggccat atataagagc agaagttgaa   420
gataatatca tggtaacttt cagaaatcag gcctctcgtc cctattcctt ctattctagc   480
cttatttctt atgaggaaga tcagaggcaa ggagcagaac ctagaaaaaa ctttgtcaag   540
cctaatgaaa ccaaaactta cttttggaaa gtgcaacatc atatggcacc cactaaagat   600
gagtttgact gcaaagcctg gcttatttct tctgatgttg acctggaaaa agatgtgcac   660
tcaggcctga ttggaccect tctggtctgc cacactaaca ctgaaccc tgctcatggg   720
agacaagtga cagtacagga atttgctctg ttttcacca tctttgatga gaccaaaagc   780
tggtacttca ctgaaaatat ggaagaaac tgcagggctc cctgcaatat ccagatggaa   840
gatcccactt taaagagaa ttatcgcttc atgcaatca atggctacat aatggataca   900
ctacctggct tagtaatggc tcaggatcaa aggattcgag ggtatctgct cagcatgggc   960
agcaatgaaa acatccattc tattcatttc agtggacatg tgttcactgt acgaaaaaaa  1020
gaggagtata aatggcact gtacaatctc tatccaggtg tttttgagac agtgaaatg   1080
ttaccatcca agctggaat tggcggggtg aatgccttaa ttggcgagca tctacatgct   1140
gggatgagca cacttttct ggtgtacagc aataagtgc agactccct gggaatggct   1200
tctggacaca ttagagattt tcagattaca gcttcaggac aatatggaca gtgggcccca   1260
aagctggcca gacttcatta ttccggatca atcaatgcct ggagcaccaa ggagcccttt   1320
tcttggatca aggtggatct gttggcacca atgattattc acggcatcaa gacccagggt   1380
gcccgtcaga agttctccag cctctacatc tcatcagttta tcatcatgta tagtcttgat  1440
gggaagaagt ggcagactta tcgaggaaat tccactggaa ccttaatggt cttctttggc   1500
aatgtggatt catctgggat aaaacacaat atttttaacc ctccaattat tgctcgatac   1560
atccgtttgc acccaactca ttatagcatt cgcagcactc ttcgcatgga gttgatgggc   1620
tgtgatttaa atagttgcag catgccattg ggaatgagca gtaaagcaat atcagatgca   1680
cagattactg cttcatccta ctttaccaat atgtttgcca cctggtctcc ttcaaaagct   1740
cgacttcacc tccaagggag gagtaatgcc tggagacctc aggtgaataa tccaaaagag   1800
tggctgcaag tggacttcca gaagacatg aaagtcacag gagtaactac tcagggagta   1860
aaatctctgc ttaccagcat gtatgtgaag gagttcctca gcagtcaagatggc   1920
catcagtgga ctctcttttt tcagaatggc aaagtaaagg ttttttcaggg aaatcaagac   1980
tccttcacac ctgtggtgaa ctctctagac caccgttac tgactcgcta ccttcgaatt   2040
cacccccaga gttgggtgca ccagattgcc ctgaggatgg aggttctggg ctgcgaggca   2100
caggacctct acgacaaaac tcacacatgc ccaccgtgcc cagctccaga actcctgggc   2160
ggaccgtcag tcttcctctt cccccccaaa cccaaggaca cctcatgat ctcccggacc   2220
cctgaggtca catgcgtggt ggtggacgtg agccacaag accctgaggt caagttcaac   2280
tggtacgtgg acggcgtgga ggtgcataat gccaagacaa agccgcggga ggagcagtac   2340
aacagcacgt accgtgtggt cagcgtcctc accgtcctgc accaggactg gctgaatggc   2400
aaggagtaca agtgcaaggt ctccaacaaa gccctcccag cccccatcga gaaaaccatc   2460
tccaaagcca aagggcagcc ccgagaacca caggtgtaca ccctgccccc atcccgggat   2520
gagctgacca agaaccaggt cagcctgacc tgcctggtca aaggcttcta tcccagcgac   2580
atcgccgtgg agtgggagag caatgggcag ccggagaaca actacaagac cacgcctccc   2640
gtgttggact ccgacggctc cttcttcctc tacagcaagc tcaccgtgga caagagcagg   2700
tggcagcagg ggaacgtctt ctcatgctcc gtgatgcatg aggctctgca caaccactac   2760
acgcagaaga gcctctccct gtctccgggt aaa                                2793

SEQ ID NO: 12      moltype = AA  length = 931
FEATURE            Location/Qualifiers
REGION             1..931
                   note = LC-Fc6His
SIGNAL             1..20
                   note = signal peptide
REGION             705..931
                   note = MISC_FEATURE - Fc sequence
source             1..931
                   mol_type = protein
                   organism = synthetic construct
SEQUENCE: 12
METDTLLLWV LLLWVPGSTG EITRTTLQSD QEEIDYDDTI SVEMKKEDFD IYDEDENQSP    60
RSFQKKTRHY FIAAVERLWD YGMSSSPHVL RNRAQSGSVP QFKKVVFQEF TDGSFTQPLY   120
RGELNEHLGL LGPYIRAEVE DNIMVTFRNQ ASRPYSFYSS LISYEEDQRQ GAEPRKNFVK   180
PNETKTYFWK VQHHMAPTKD EFDCKAWAYF SDVDLEKDVH SGLIGPLLVC HTNTLNPAHG   240
RQVTVQEFAL FFTIFDETKS WYFTENMERN CRAPCNIQME DPTFKENYRF HAINGYIMDT   300
LPGLVMAQDQ RIRWYLLSMG SNENIHSIHF SGHVFTVRKK EEYKMALYNL YPGVFETVEM   360
LPSKAGIWRV ECLIGEHLHA GMSTLFLVYS NKCQTPLGMA SGHIRDFQIT ASGQYGQWAP   420
KLARLHYSGS INAWSTKEPF SWIKVDLLAP MIIHGIKTQG ARQFSSLYI SQFIIMYSLD   480
GKKWQTYRGN STGTLMVFFG NVDSSGIKHN IFNPPIIARY IRLHPTHYSI RSTLRMELMG   540
CDLNSCSMPL GMESKAISDA QITASSYFTN MFATWSPSKA RLHLQGRSNA WRPQVNNPKE   600
WLQVDFQKTM KVTGVTTQGV KSLLTSMYVK EFLISSSQDQ HQWTLFFQNG KVKVFQGNVD   660
SFTPVVNSLD PPLLTRYLRI HPQSWVHQIA LRMEVLGCEA QDLYDKTHTC PPCPAPELLG   720
GPSVFLFPPK PKDTLMISRT PEVTCVVVDV SHEDPEVKFN WYVDGVEVHN AKTKPREEQY   780
NSTYRVVSVL TVLHQDWLNG KEYKCKVSNK ALPAPIEKTI SKAKGQPREP QVYTLPPSRD   840
ELTKNQVSLT CLVKGFYPSD IAVEWESNGQ PENNYKTTPP VLDSDGSFFL YSKLTVDKSR   900
WQQGNVFSCS VMHEALHNHY TQKSLSLSPG K                                  931
```

```
SEQ ID NO: 13              moltype = DNA   length = 7583
FEATURE                    Location/Qualifiers
misc_feature               1..7583
                           note = FIX-Fc Chain DNA sequence
sig_peptide                690..777
                           note = FIX signal peptide
misc_feature               778..1076
                           note = Intron - FIX mini intron
misc_feature               1077..2371
                           note = FIX sequence
misc_feature               2372..3050
                           note = Fc region
source                     1..7583
                           mol_type = other DNA
                           organism = synthetic construct
SEQUENCE: 13
gcgcgcgttg acattgatta ttgactagtt attaatagta atcaattacg gggtcattag    60
ttcatagccc atatatggag ttccgcgtta cataacttac ggtaaatggc ccgcctggct   120
gaccgcccaa cgacccccgc ccattgacgt caataatgac gtatgttccc atagtaacgc   180
caatagggac tttccattga cgtcaatggg tggagtattt acggtaaact gcccacttgg   240
cagtacatca agtgtatcat atgccaagta cgccccctat tgacgtcaat gacggtaaat   300
ggcccgcctg gcattatgcc cagtacatga ccttatggga ctttcctact tggcagtaca   360
tctacgtatt agtcatcgct attaccatgg tgatgcggtt ttggcagtac atcaatgggc   420
gtggatagcg gtttgactca cggggatttc caagtctcca ccccattgac gtcaatggga   480
gtttgttttg gcaccaaaat caacgggact ttccaaaatg tcgtaacaac tccgccccat   540
tgacgcaaat gggcggtagg cgtgtacggt gggaggtcta taagcagc gctctctggc    600
taactagaga acccactgct tactggctta tcgaaattaa tacgactcac tatagggaga   660
cccaagcttc gcgacgtacg gccgccacca tgcagcgcgt gaacatgatc atggcagaat   720
caccaggcct catcaccatc tgccttttag gatatctact cagtgctgaa tgtacaggtt   780
tgttttccttt tttaaaatac attgagtatg cttgccttta agatataagaa atatctgatg   840
ctgtcttctt cactaaattt tgattacatg atttgacagc aatattgaag agtctaacag   900
ccagcacgca ggttggtaag tactgtggga acatcacaga ttttggctcc atgccctaaa   960
gagaaattgg ctttcagatt atttggatta aaaacaaaga ctttcttaag agatgtaaaa  1020
ttttcatgat gttttctttt ttgctaaaac taaagaatta ttcttttaca tttcagtttt  1080
tcttgatcat gaaaacgcca acaaaattct gaatcggcca aagaggtata attcaggtaa  1140
attggaagag tttgttcaag ggaatctaga gagaatgt atggaagaaa agtgtagttt    1200
tgaagaagca cgagaagttt ttgaaaacac tgaaagaaca actgaatttt ggaagcagta  1260
tgttgatgga gatcagtgtg agtccaatcc atgtttaaat ggcggcagtt gcaaggatga  1320
cattaattcc tatgaatgtt ggtgtccctt tggatttgaa ggaaagaact gtgaattaga  1380
tgtaacatgt aacattaaga atggcagatg cgagcagttt tgtaaaaata gtgctgataa  1440
caaggtggtt tgctcctgta ctgagggata tcgacttgca gaaaaccaga gtcctgtga  1500
accagcagtg ccatttccat gtggaagagt ttctgtttca caaacttcta agctcacccg  1560
tgctgagact gttttttcctg atgtggacta tgtaaattct actgaagctg aaaccatttt  1620
ggataacatc actcaaagca cccaatcatt taatgacttc actcgggttg ttggtggaga  1680
agatgccaaa ccaggtcaat tcccttggca ggttgttttg aatggtaaag ttgatgcatt  1740
ctgtggaggc tctatcgtta tgaaaaatg gattgtaact gctgcccact gtgttgaaac  1800
tggttgttaaa attacagttg tcgcaggtga acataatatt gaggagaca aacatacaga  1860
gcaaaagcga aatgtgattc gaattattcc tcaccacaac tacaatgcag ctattaataa  1920
gtacaaccat gacattgccc ttctggaact ggacgaaccc ttagtgctaa acagctacgt  1980
tacacctatt tgcattgctg acaaggaata cacgaacatc ttcctcaaat ttggatctgg  2040
ctatgtaagt ggctgggaa gagtcttcca caagggaga tcagctttag ttcttcagta    2100
ccttagagtt ccacttgttg accgagccaa atgtcttcga tctacaaagt tcaccatcta  2160
taacaacatg ttctgtgctg gcttccatga aggagg ga gattcatgtc aaggagatg   2220
tgggggaccc catgttactg aagtggaagg accagtttc ttaactggaa ttattagctg   2280
gggtgaagag tgtgcaatga aaggcaaata tggaatatat accaaggtgt cccggtatgt  2340
caactggatt aaggaaaaaa caaagctcac tgacaaaact cacacatgcc caccgtgccc  2400
agctccggaa ctcctgggcg gaccgtcagt cttcctcttc cccccaaaac ccaaggacac  2460
cctcatgatc tcccggaccc ctgaggtcac atgcgtggtg gtggacgtga gccacgaaga  2520
ccctgaggtc aagttcaact ggtacgtgga cggcgtggag gtgcataatg ccaagacaaa  2580
gccgcgggag gagcagtaca acagcacgta ccgtgtggtc agcgtcctca ccgtcctgca  2640
ccaggactgg ctgaatggca aggagtacaa gtgcaaggtc tccaacaaag ccctcccagc  2700
ccccatcgag aaaaccatct ccaaagccaa gggcagcccc cgagaaccac aggtgtacac  2760
cctgccccca tcccgggatg agctgaccaa gaaccaggtc agcctgacct gcctggtcaa  2820
aggcttctat cccagcgaca tcgccgtgga gtgggagagc aatgggcagc cggagaacaa  2880
ctacaagacc acgcctcccg tgttggactc cgacggctcc ttcttcctct acagcaagct  2940
caccgtggac aagagcaggt ggcagcaggg gaacgtcttc tcatgctccg tgatgcatga  3000
ggctctgcac aaccactaca cgcagaagag cctctccctg tctccgggta atgagaatt   3060
cagacatgat aagatacatt gatgagtttg gacaaaccac aactagaatg cagtgaaaaa  3120
aatgctttat ttgtgaaatt tgtgatgcta ttgctttatt tgtaaccatt ataagctgca  3180
ataaacaagt tgggggtggg caagaactcc agcatgagat cccgcgctg gaggatcatc   3240
cagccggcgt cccggaaaac gattccgaag cccaaccttt catagaaggc ggcggtggaa  3300
tcgaaatctc gtagcacgtg tcagtcctgc tcctcggcca cgaagtgcac gcagttgccg  3360
gccgggtcgc gcagggcgaa ctcccgcccc cacggctgct cgccgatctc ggtcatggcc  3420
ggcccggagg cgtcccggaa gttcgtggac acgacctccg accactcggc gtacagctcg  3480
tccaggccgc gcacccacac ccaggccagg tgttgtccg gccaccctg tcctggacc    3540
gcgctgatga caggtcac gtcgtcccgg accacaccgg cgaagtcgtc ctccacgaag   3600
tcccgggaga acccgagccg gtcggtccag aactcgaccg ctccggcgac gtcgcgcgcg  3660
gtgagcaccg gaacggcact ggtcaacttg gccatgtttt agttcctcac cttgtcgtat  3720
tatactatgc cgatatacta tgccgatgat taattgtcaa cacgtgctga tcagatccga  3780
```

```
aaatggatat acaagctccc gggagctttt tgcaaaagcc taggcctcca aaaaagcctc 3840
ctcactactt ctggaatagc tcagaggcag aggcggcctc ggcctctgca taataaaaa  3900
aaattagtca gccatggggc ggagaatggg cggaactggg cggagttagg ggcgggatgg 3960
gcggagttag gggcgggact atggttgctg actaattgag atgcatgctt tgcatacttc 4020
tgcctgctgg ggagcctggg gactttccac acctggttgc tgactaattg agatgcatgc 4080
tttgcatact tctgcctgct ggggagcctg gggactttcc acaccctcgt cgagctagct 4140
tcgtgaggct ccggtgcccg tcagtgggca gagcgcacat cgcccacagt ccccgagaag 4200
ttgggggggag gggtcggcaa ttgaaccggt gcctagagaa ggtggcgcgg ggtaaactgg 4260
gaaagtgatg tcgtgtactg gctccgcctt tttcccgagg gtgggggaga accgtatata 4320
agtgcagtag tcgccgtgaa cgttcttttt cgcaacggtt ttgccgccag aacacaggta 4380
agtgccgtgt gtggttcccg cgggcctggc ctctttacgg gttatggccc ttgcgtgcct 4440
tgaattactt ccacctggct ccagtacgtg attcttgatc ccgagctgga gccaggggcg 4500
ggccttgcgc tttaggagcc ccttcgcctc gtgcttgagt tgaggcctgg cctgggcgct 4560
ggggccgccg cgtcgcgaatc tggtggcacc ttcgcgcctg tctcgctgct ttcgataagt 4620
ctctagccat ttaaaatttt tgatgacctg ctgcgacgct tttttttctgg caagatagtc 4680
ttgtaaatgc gggccaggat ctgcacactg gtatttcggt ttttgggggcc gcgggcggcg 4740
acggggcccg tgcgtcccag cgcacatgtt cggcgaggcg gggcctgcga gcgcggccac 4800
cgagaatcgg acggggggtag tctcaagctg gccggcctgc ttcggtgcct ggcctgcgcg 4860
cgccgtgtat cgcccccgccc tgggcggcaa ggctggcccg gtcggcacca gttgcgtgag 4920
cggaaagatg gccgcttccc ggccctgctc caggggggctc aaaatggagg acgcggcgct 4980
cgggagagcg ggcgggtgag tcacccacac aaaggaaagg ggcctttccg tcctcagccg 5040
tcgcttcatg tgactccacg gagtaccggg cgccgtccag tagttctgga 5100
gcttttggag tacgtcgtct ttaggttggg gggagggggtt ttatgcgatg gagtttcccc 5160
acactgagtg ggtggagact gaagttaggc cagcttggca cttgatgtaa ttctccttgg 5220
aatttgccct ttttgagttt ggatcttggt tcattctcaa gcctcagaca gtggttcaaa 5280
gttttttttct tccatttcag gtgtcgtgaa cacgtggtcg ggccgcgcc gccaccatgg 5340
agacagacac actcctgcta tgggtactgc tgctctgggt tccaggttcc actggtgaca 5400
aaactcacac atgcccaccg tgcccagcac ctgaactcct gggaggaccg tcagtcttcc 5460
tcttcccccc aaaacccaag gacacccctca tgatctcccg gacccctgag gtcacatgcg 5520
tggtggtgga cgtgagccac gaagaccctg aggtcaagtt caactggtac gtggacggcg 5580
tggaggtgca taatgccaag acaaagccgc gggaggagca gtacaacagc acgtaccgtg 5640
tggtcagcgt cctcaccgtc ctgcaccagg actggctgaa tggcaaggag tacaagtgca 5700
aggtctccaa caaagccctc ccagccccca tcgagaaaac catctccaaa gccaagggc 5760
agccccgaga accacaggtg tacaccctgc cccatcccg cgatgagctg accaagaacc 5820
aggtcagcct gacctgcctg gtcaaaggct tctatcccag cgacatcgcc gtggagtgga 5880
agagcaatgg gcagccggag aacaactaca agaccacgcc tcccgtgttg gactccgacg 5940
gctccttctt cctctacagc aagctcaccg tggacaagag caggtggcag caggggaacg 6000
tcttctcatg ctccgtgatg catgaggctc tgcacaacca ctacacgcag aagagcctct 6060
ccctgtctcc gggtaaatga ctcgagagat ctggccgact gggccgtttc gaaggtaag 6120
cctatcccta accctctcct cggtctcgat tctacgcgta ccggtcatca tcaccatcac 6180
cattgagttt aaacccgctg atcagcctcg actgtgcctt ctagttgcca gccatctgtt 6240
gtttgccct ccccgtgcc ttccttgacc ctggaaggtg ccactcccac tgtccttcc 6300
taataaaatg aggaaattgc atcgcattgt ctgagtaggt gtcattctat tctggggggt 6360
ggggtgggc aggacagcaa gggggaggat tgggaagaca atagcaggca tgctgggat 6420
gcggtgggct ctatggcttc tgaggcggaa agaaccagtg gcggtaatac ggttatccac 6480
agaatcaggg gataacgcag gaaagaacat gtgagcaaaa ggccagcaaa aggccaggaa 6540
ccgtaaaaag gccgcgttgc tggcgttttt ccataggctc cgcccccctg acgagcatca 6600
caaaaatcga cgctcaagtc agaggtggcg aaacccgaca ggactataaa gataccaggc 6660
gtttccccct agaagctccc tcgtgcgctc tcctgttccg accctgccgc ttaccggata 6720
cctgtccgcc tttctccctt cgggaagcgt ggcgctttct catagctcac gctgtaggta 6780
tctcagttcg gtgtaggtcg ttcgctccaa gctgggctgt gtgcacgaac cccccgttca 6840
gcccgaccgc tgcgccttat ccggtaacta tcgtcttgag tccaacccgg taagacacga 6900
cttatcgcca ctggcagcag ccactggtaa caggattagc agagcgaggt atgtaggcgg 6960
tgctacagag ttcttgaagt ggtggcctaa ctacggctac actagaagaa cagtatttgg 7020
tatctgcgct ctgctgaagc cagttacctt cggaaaaaga gttggtagct cttgatccgg 7080
caaacaaacc accgctggta gcggtggttt ttttgtttgc aagcagcaga ttacgcgcag 7140
aaaaaaagga tctcaagaag atcctttgat cttttctacg gggtctgacg ctcagtggaa 7200
cgaaaactca cgttaaggga ttttggtcat gacattaacc tataaaaata ggcgtatcac 7260
gaggcccttt cgtctcgcgc gtttcggtga tgacggtgaa aacctctgac acatgcagct 7320
cccggagacg gtcacagctt gtctgtaagc ggatgccggg agcagacaag cccgtcaggg 7380
cgcgtcagcg ggtgttggcg ggtgtcgggg ctggcttaac tatgcggcat cagagcagat 7440
tgtactgaga gtgcaccata tatgcggtgt gaaataccgc acagatgcgt aaggagaaaa 7500
taccgcatca ggcgccattc gccattcagg ctgcgcaact gttgggaagg gcgatcggtg 7560
cgggcctctt cgctattacg cca                                         7583

SEQ ID NO: 14         moltype = AA  length = 688
FEATURE               Location/Qualifiers
REGION                1..688
                      note = FIX-Fc chain
SIGNAL                1..46
                      note = amino acid signal sequence
REGION                462..688
                      note = MISC_FEATURE - Fc part of FIX-Fc
source                1..688
                      mol_type = protein
                      organism = synthetic construct
SEQUENCE: 14
MQRVNMIMAE SPSLITICLL GYLLSAECTV FLDHENANKI LNRPKRYNSG KLEEFVQGNL  60
ERECMEEKCS FEEAREVFEN TERTTEFWKQ YVDGDQCESN PCLNGGSCKD DINSYECWCP 120
```

```
FGFEGKNCEL DVTCNIKNGR CEQFCKNSAD NKVVCSCTEG YRLAENQKSC EPAVPFPCGR   180
VSVSQTSKLT RAETVFPDVD YVNSTEAETI LDNITQSTQS FNDFTRVVGG EDAKPGQFPW   240
QVVLNGKVDA FCGGSIVNEK WIVTAAHCVE TGVKITVVAG EHNIEETEHT EQKRNVIRII   300
PHHNYNAAIN KYNHDIALLE LDEPLVLNSY VTPICIADKE YTNIFLKFGS GYVSGWGRVF   360
HKGRSALVLQ YLRVPLVDRA TCLRSTKFTI YNNMFCAGFH EGGRDSCQGD SGGPHVTEVE   420
GTSFLTGIIS WGEECAMKGK YGIYTKVSRY VNWIKEKTKL TDKTHTCPPC PAPELLGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALP APIEKTISKA KGQPREPQVY TLPPSRDELT   600
KNQVSLTCLV KGFYPSDIAV EWESNGQPEN NYKTTPPVLD SDGSFFLYSK LTVDKSRWQQ   660
GNVFSCSVMH EALHNHYTQK SLSLSPGK                                     688

SEQ ID NO: 15           moltype = DNA  length = 2082
FEATURE                 Location/Qualifiers
misc_feature            1..2082
                        note = Full Length FVII-Fc DNA Sequence
sig_peptide             1..180
                        note = FVIII signal peptide
sig_peptide             1..180
                        note = FVII signal peptide
misc_feature            1402..2082
                        note = Fc region
source                  1..2082
                        mol_type = other DNA
                        organism = synthetic construct
SEQUENCE: 15
atggtctccc aggccctcag gctcctctgc cttctgcttg ggcttcaggg ctgcctggct    60
gcaggcgggg tcgctaaggc ctcaggagga gaaacacggg acatgccgtg gaagccgggg   120
cctcacagag tcttcgtaac ccaggaggaa gcccacggcg tcctgcaccg cgcgcggcgc   180
gccaacgcgt tcctggagga gctgcggccg ggctccctgg agagggagtg caaggaggag   240
cagtgctcct tcgaggaggc ccgggagatc ttcaaggacg cggagaggac gaagctgttc   300
tggatttctt acagtgatgg ggaccagtgt gcctcaagtc catgccagaa tgggggctcc   360
tgcaaggacc agctccagtc ctatatctgc ttctgcctcc ctgccttcga gggcggaaac   420
tgtgagacgc acaaggatga ccagctgatc tgtgtgaacg agaacggcgg ctgtgagcag   480
tactgcagtg accacacggg caccaagcgc tcctgtcggt gccacgaggg gtactctctg   540
ctggcagacg gggtgtcctg cacacccgta gttgaatatc catgtggaaa aatacctatt   600
ctagaaaaaa gaaatgccag caaacccaa ggccgaattg tggggggcaa ggtgtgcccc   660
aaaggggagt gtccatggca ggtcctgttg ttggtgaatg gagctcagtt gtgtgggggg   720
accctgatca acaccatctg ggtggtctcc gcggccact gtttcgacaa aatcaagaac   780
tggagggaacc tgatccggtt gctggaggag cacgacctca gcgagcacga cggggatgag   840
cagagccggc gggtggcgca ggtcatcatc cccagcacgt acgtcccggg caccaccaac   900
cacgacatcg cgctgctccg cctgcaccag cccgtggtcc tcactgacca tgtggtgccc   960
ctctgcctgc ccgaacggac gttctctgag aggacgctgg ccttcgtgcg cttctcattg  1020
gtcagcggct ggggccagct gctggaccgt ggcgccaccg ccctggagct catggtcctc  1080
aacgtgcccc ggctgatgac ccaggactgc ctgcagcagt cacggaaggt gggagactcc  1140
ccaaatatca cggagtacat gttctgtgcc ggctactcgg atggcagcaa ggactcctgc  1200
aaggggggaca gtggaggccc catgccacc cactaccggg gcagtggta cctgacgggc  1260
atcgtcagtt ggggccaggg ctgcgcaacc gtgggccact ttgggggtgta caccagggtc  1320
tcccagtaca tcgagtggct gcaaaagctc atgcgctcag agccacgcc aggagtcctc  1380
ctgcgagccc catttcccta ggacaaaact cacacatgcc caccgtgccc agctccagaa  1440
ctcctggggcg gaccgtcagt cttcctcttc ccccaaaac ccaaggacac cctcatgatc  1500
tcccggaccc ctgaggtcac atgcgtggtg gtggacgtga gccacgaaga ccctgaggtc  1560
aagttcaact ggtacgtgga cggcgtggag gtgcataatg ccaagacaaa gccgcgggag  1620
gagcagtaca acagcacgta ccgtgtggtc agcgtcctca ccgtcctgca ccaggactgg  1680
ctgaatggca aggagtacaa gtgcaaggtc tccaacaaag ccctcccagc ccccatcgag  1740
aaaaccatct ccaaagccaa agggcagccc cgagaaccac aggtgtacac cctgcccca  1800
tcccgggatg agctgaccaa gaaccaggtc agcctgacct gcctggtcaa aggcttctat  1860
cccagcgaca tcgccgtgga gtgggagagc aatgggcagc cggagaacaa ctacaagacc  1920
acgcctcccg tgttggactc cgacggctcc ttcttcctct acagcaagct caccgtggac  1980
aagagcaggt ggcagcaggg gaacgtcttc tcatgctccg tgatgcatga ggctctgcac  2040
aaccactaca cgcagaagag cctctccctg tctccgggta aa                    2082

SEQ ID NO: 16           moltype = AA  length = 693
FEATURE                 Location/Qualifiers
REGION                  1..693
                        note = FVII-Fc chain
SIGNAL                  1..60
                        note = signal sequence
REGION                  467..693
                        note = MISC_FEATURE - Fc region
source                  1..693
                        mol_type = protein
                        organism = synthetic construct
SEQUENCE: 16
MVSQALRLLC LLLGLQGCLA AGGVAKASGG ETRDMPWKPG PHRVFVTQEE AHGVLHRRRR    60
ANAFLEELRP GSLERECKEE QCSFEEAREI FKDAERTKLF WISYSDGDQC ASSPCQNGGS   120
CKDQLQSYIC FCLPAFEGRN CETHKDDQLI CVNENGCEQ YCSDHTGTKR SCRCHEGYSL   180
LADGVSCTPT VEYPCGKIPI LEKRNASKPQ GRIVGGKVCP KGECPWQVLL LVNGAQLCGG   240
TLINTIWVVS AAHCFDKIKN WRNLIAVLGE HDLSEHDGDE QSRRVAQVII PSTYVPGTTN   300
HDIALLRLHQ PVVLTDHVVP LCLPERTFSE RTLAFVRFSL VSGWGQLLDR GATALELMVL   360
```

```
NVPRLMTQDC LQQSRKVGDS PNITEYMFCA GYSDGSKDSC KGDSGGPHAT HYRGTWYLTG    420
IVSWGQGCAT VGHFGVYTRV SQYIEWLQKL MRSEPRPGVL LRAPFPDKTH TCPPCPAPEL    480
LGGPSVFLFP PKPKDTLMIS RTPEVTCVVV DVSHEDPEVK FNWYVDGVEV HNAKTKPREE    540
QYNSTYRVVS VLTVLHQDWL NGKEYKCKVS NKALPAPIEK TISKAKGQPR EPQVYTLPPS    600
RDELTKNQVS LTCLVKGFYP SDIAVEWESN GQPENNYKTT PPVLDSDGSF FLYSKLTVDK    660
SRWQQGNVFS CSVMHEALHN HYTQKSLSLS PGK                                693

SEQ ID NO: 17           moltype = AA   length = 20
FEATURE                 Location/Qualifiers
REGION                  1..20
                        note = PAS sequence
source                  1..20
                        mol_type = protein
                        organism = synthetic construct
SEQUENCE: 17
ASPAAPAPAS PAAPAPSAPA                                                20

SEQ ID NO: 18           moltype = AA   length = 20
FEATURE                 Location/Qualifiers
REGION                  1..20
                        note = PAS sequence
source                  1..20
                        mol_type = protein
                        organism = synthetic construct
SEQUENCE: 18
AAPASPAPAA PSAPAPAAPS                                                20

SEQ ID NO: 19           moltype = AA   length = 20
FEATURE                 Location/Qualifiers
REGION                  1..20
                        note = PAS sequence
source                  1..20
                        mol_type = protein
                        organism = synthetic construct
SEQUENCE: 19
APSSPSPSAP SSPSPASPSS                                                20

SEQ ID NO: 20           moltype = AA   length = 19
FEATURE                 Location/Qualifiers
REGION                  1..19
                        note = PAS sequence
source                  1..19
                        mol_type = protein
                        organism = synthetic construct
SEQUENCE: 20
APSSPSPSAP SSPSPASPS                                                 19

SEQ ID NO: 21           moltype = AA   length = 20
FEATURE                 Location/Qualifiers
REGION                  1..20
                        note = PAS sequence
source                  1..20
                        mol_type = protein
                        organism = synthetic construct
SEQUENCE: 21
SSPSAPSPSS PASPSPSSPA                                                20

SEQ ID NO: 22           moltype = AA   length = 24
FEATURE                 Location/Qualifiers
REGION                  1..24
                        note = PAS sequence
source                  1..24
                        mol_type = protein
                        organism = synthetic construct
SEQUENCE: 22
AASPAAPSAP PAAASPAAPS APPA                                           24

SEQ ID NO: 23           moltype = AA   length = 20
FEATURE                 Location/Qualifiers
REGION                  1..20
                        note = PAS sequence
source                  1..20
                        mol_type = protein
                        organism = synthetic construct
SEQUENCE: 23
ASAAAPAAAS AAASAPSAAA                                                20
```

ON-COLUMN VIRAL INACTIVATION METHODS

RELATED APPLICATIONS

This application is a continuation of U.S. patent application Ser. No. 16/793,676, filed Feb. 18, 2020, which is a continuation of U.S. patent application Ser. No. 15/024,988, filed Mar. 25, 2016, now U.S. Pat. No. 10,611,794, which is a 35 U.S.C. § 371 filing of International Patent Application No. PCT/US2014/057524, filed Sep. 25, 2014, which claims priority to U.S. Provisional Patent Application Ser. No. 62/028,657, filed Jul. 24, 2014; and 61/882,488, filed Sep. 25, 2013, the entire disclosures of which are hereby incorporated herein by reference.

SEQUENCE LISTING

The instant application contains a Sequence Listing which has been submitted electronically in XML format and is hereby incorporated by reference in its entirety. Said XML file, created on Jan. 10, 2023, is named 738547_SA9-446USCON2_ST26.xml, and is 85,522 bytes in size.

BACKGROUND OF THE INVENTION

Field of the Invention

The present invention is directed to a method of inactivating virus that is present during production of a polypeptide of interest. In particular, the present invention is directed to a method of on-column virus inactivation using a low pH and high salt wash solution that effectively inactivates viruses with minimum recovery loss of the polypeptide.

Background Art

With the advent of recombinant protein technology, a protein of interest can be produced using cultured cell lines engineered to express the protein. The use of the desired recombinant protein for pharmaceutical applications is however generally contingent on the ability to reliably recover adequate levels of the protein from impurities such as host cell proteins, cell culture additives, and viruses. Various chromatography methods have been employed to remove the impurities and to recover the protein.

A number of methods for inactivating viruses based on different mechanisms are known in the art. Each method however has its own disadvantages, and may not be suitable or optimal for some protein products. For example, when low pH is used to inactivate viruses, it has the potential to precipitate proteins, cause aggregation of the product, and/or alter the conformation of certain proteins which can lead to product loss. In addition, during the protein purification process, the low pH virus inactivation step is typically performed after the protein of interest has been eluted from the chromatography column and held in a tank or vessel, especially if significant product loss may be caused by low pH wash. Adding an extra step in a tank or vessel to inactivate virus is a cause for inconvenience.

Therefore, there are needs to develop on-column viral inactivation steps that can effectively inactivate viruses and at the same time can improve the product yield in a convenient manner.

BRIEF SUMMARY OF THE INVENTION

The present invention pertains to a method of inactivating virus that is present during production of a polypeptide of interest, comprising: (a) binding the polypeptide to a chromatography matrix, and (b) performing a virus inactivation step by washing the polypeptide-bound chromatography matrix with a wash solution at a pH of lower than about 4.0, wherein the wash solution comprises a sufficient concentration of salt to substantially reduce elution of the polypeptide during the virus inactivation step.

In certain embodiments, the chromatography matrix is an affinity chromatography matrix. In certain embodiments, the affinity chromatography matrix is a Protein A column. In certain embodiments, the Protein A column is selected from the group consisting of MABSELECT™, MABSELECT™ SuRe, MABSELECT™ SuRe LX, ESHMUNO® A, AMSPHERE™ JWT203, TOYOPEARL® AF-rProtein A-650F, PROSEP®-vA Ultra, PROSEP® Ultra Plus, and PROSEP®-vA High Capacity, and any combination thereof. In some embodiments, the Protein A ligand is immobilized on a matrix selected from the group consisting of dextran based matrix, agarose based matrix, polystyrene based matrix, hydrophilic polyvinyl ethyl based matrix, rigid polymethacrylate based matrix, porous polymer based matrix, controlled pore glass based matrix, and any combination thereof.

In certain embodiments, the chromatography matrix is a mixed-mode chromatography matrix. In certain embodiments, the chromatography matrix is a mixed-mode anion-exchange chromatography matrix. In certain embodiments, the mixed-mode chromatography matrix is selected from the group consisting of CAPTO™ Adhere, CAPTO™ MMC, ESHMUNO® HCX, CAPTO™ MMC ImpRes, CAPTO™ Blue, NUVIA™ cPrime, BLUE SEPHAROSE® Fast Flow, CAPTO™ Adhere ImpRes, CHT™ Ceramic Hydroxyapatite, CFT™ Ceramic Fluoroapatite, and any combinations thereof. In some embodiments, the mixed-mode chromatography matrix is selected from the group consisting of dextran based matrix, agarose based matrix, polystyrene based matrix, polyvinyl ethyl hydrophilic polymer based matrix, macroporous highly crosslinked polymer based matrix, hydroxyapatite ((Ca5(PO4)3OH)2) based matrix, fluoroapatite ((Ca5(PO4)3F)2) based matrix, and any combinations thereof.

In certain embodiments, the polypeptide of interest is a CH2/CH3-containing polypeptide. In certain embodiments, the CH2/CH3-containing polypeptide is an antibody or an antibody fragment. In one embodiment, the antibody is a monoclonal antibody.

In certain embodiments, the polypeptide of interest comprises a clotting factor. In certain embodiments, the polypeptide of interest is FIX-Fc, FVIII-Fc, or FVII-Fc. In certain embodiments, the polypeptide is a monomer-dimer hybrid. In certain embodiments, the polypeptide further comprises a heterologous moiety. In one embodiment, the heterologous moiety is selected from the group consisting of albumin, albumin-binding polypeptide, Fc, PAS, the C-terminal peptide (CTP) of the β subunit of human chorionic gonadotropin, polyethylene glycol (PEG), hydroxyethyl starch (HES), albumin-binding small molecules, and any combinations thereof.

In certain embodiments, the polypeptide of interest is recombinantly produced in a cell culture. In certain embodiments, the cell culture is a human cell culture. In one embodiment, the human cell culture is Human Embryonic Kidney (HEK) 293 cell.

In certain embodiments, the polypeptide of interest is harvested after recombinant production in the cell culture. In certain embodiments, the polypeptide is bound to the chromatography matrix at a pH from about 6.0 to about 8.0.

In certain embodiments, the elution of the polypeptide during the virus inactivation step is reduced to less than 30%. In certain embodiments, the elution of the polypeptide during the virus inactivation step is reduced to less than 25%, less than 20%, less than 15%, less than 10%, or less than 5%.

In certain embodiments, the pH of the wash solution is about 2.5 to about 4.0. In other embodiments, the pH of the wash solution is about 2.5 to about 3.0, about 3.0 to about 3.5, or about 3.5 to about 4.0. In certain embodiments, the pH of the wash solution is about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0.

In certain embodiments, the concentration of the salt in the wash solution is greater than about 0.5 M. In certain embodiments, the concentration of the salt is about 0.5 M to about 1.0 M, about 1.0 M to about 1.5 M, about 1.5 M to about 2.0 M, about 2.0 M to about 2.5 M, about 2.5 M to about 3.0 M, about 3.0 M to about 3.5 M, or about 3.5 M to about 4 M.

In certain embodiments, the salt in the wash solution is a sodium salt, a potassium salt, or an ammonium salt.

In certain embodiments, the wash solution further comprises one or more components selected from the group consisting of a polymer, an organic solvent, a detergent, and arginine or an arginine derivative.

In certain embodiments, the method comprises more than one virus-inactivation step, wherein identical or different wash solutions can be used. In certain embodiments, at least one of the wash solutions comprises arginine, an arginine derivative, or a mixture thereof. In certain embodiments, at least one of the wash solutions comprises a detergent.

In certain embodiments, the method further comprises eluting the polypeptide from the chromatography matrix with an elution solution. In certain embodiments, at least about 70% of the polypeptide is recovered in the elution solution. In certain embodiments, at least about 75%, at least about 80%, at least about 85%, at least about 90%, or at least about 95% of the polypeptide is recovered in the elution solution.

BRIEF DESCRIPTION OF THE DRAWINGS/FIGURES

FIG. 1. The chromatogram showing the separation of proteins in a Protein A chromatography column using a wash solution containing 2 M ammonium sulfate at pH 3.5. $UV_{280}$ indicates protein concentration in the collected fractions.

Figure 2:
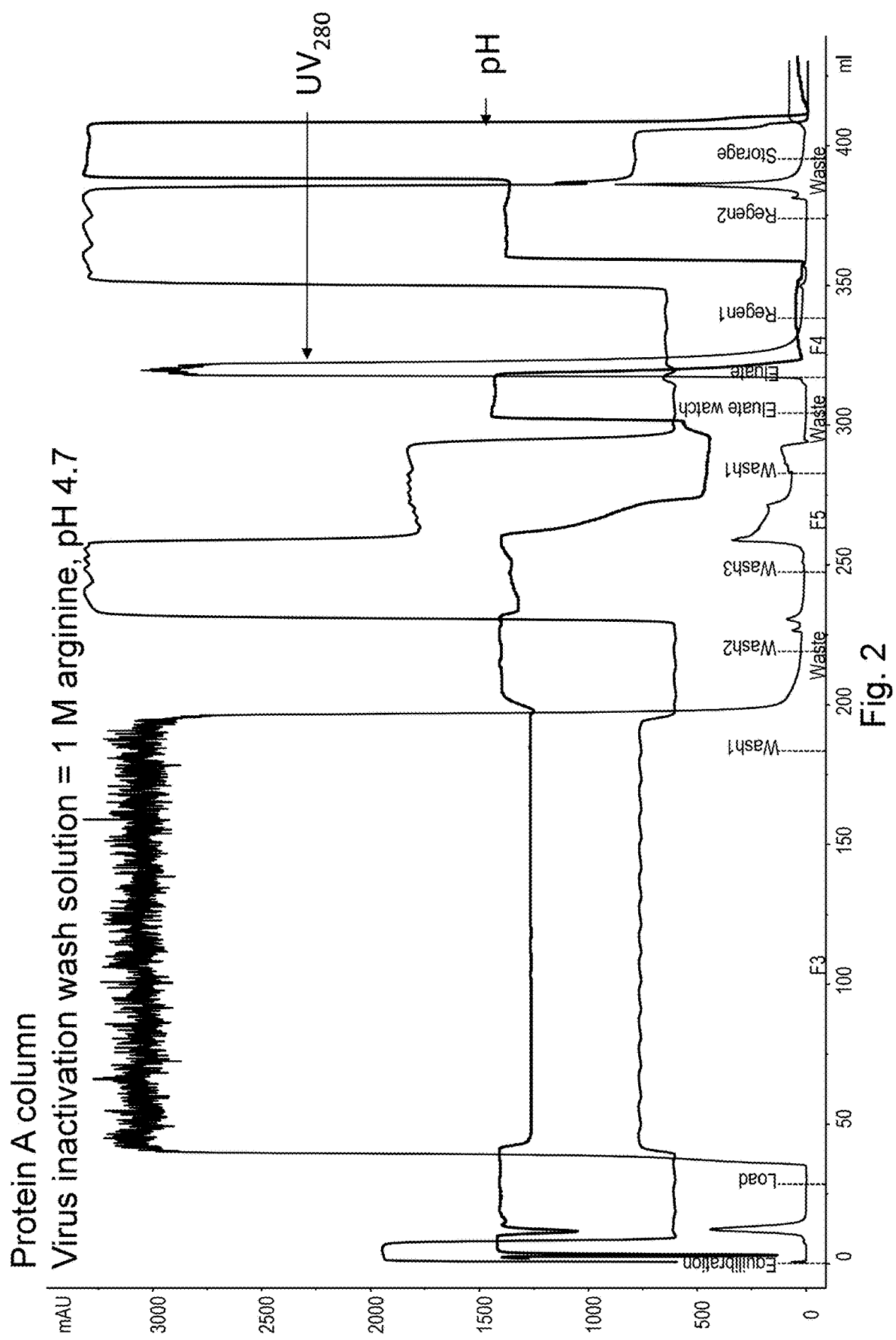

FIG. 2. The chromatogram showing the separation of proteins in a Protein A chromatography column using a wash solution containing 1 M arginine at pH 4.7. $UV_{280}$ indicates protein concentration in the collected fractions.

Figure 3:
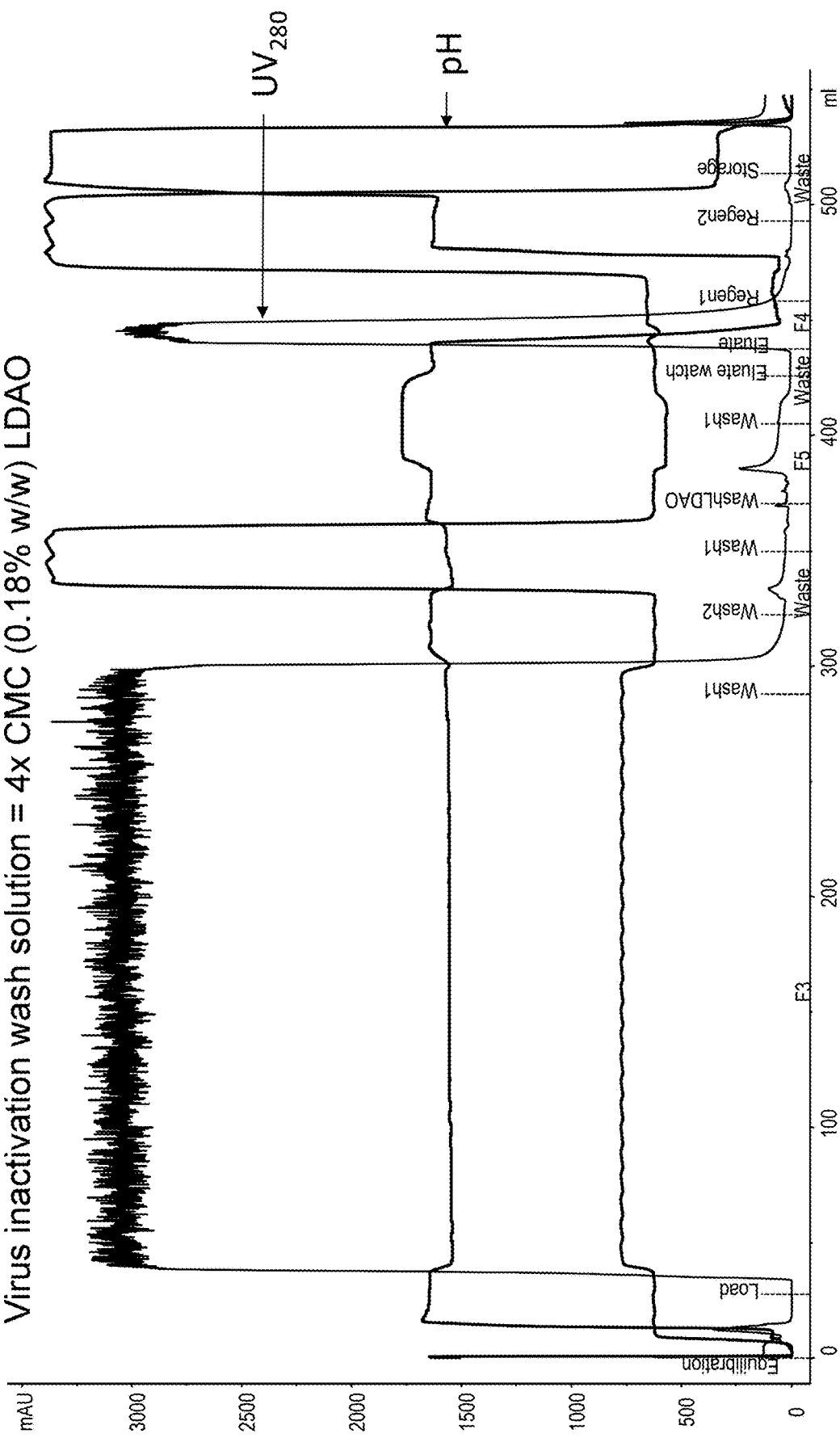

FIG. 3. The chromatogram showing the separation of proteins in a Protein A chromatography column using a wash solution containing 4×CMC (or 0.18% w/w) LDAO. $UV_{280}$ indicates protein concentration in the collected fractions.

Figure 4:
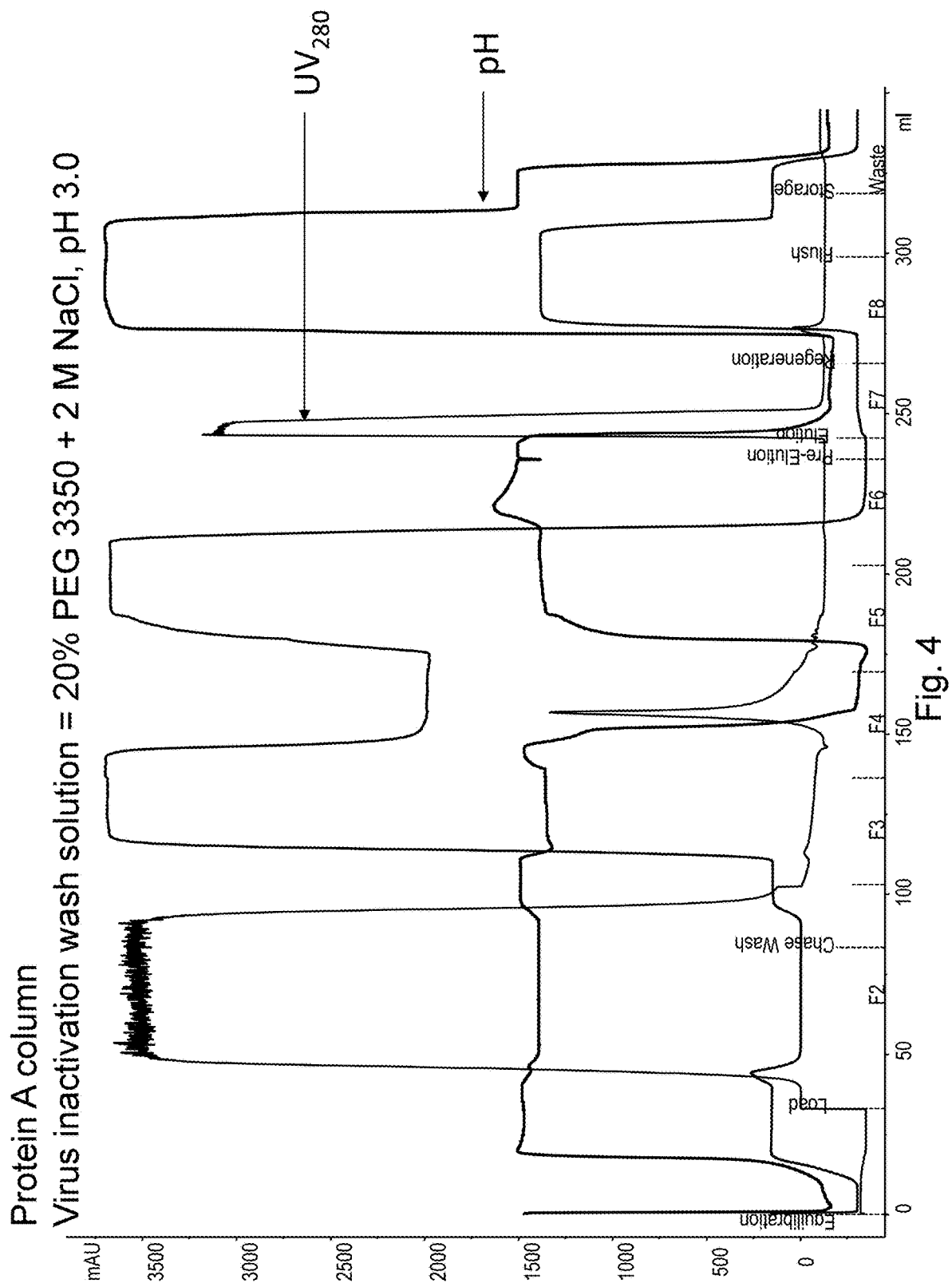

FIG. 4. The chromatogram showing the separation of proteins in a Protein A chromatography column using a wash solution containing 2 M NaCl and 20% PEG at pH 3.0. $UV_{280}$ indicates protein concentration in the collected fractions.

Figure 5:
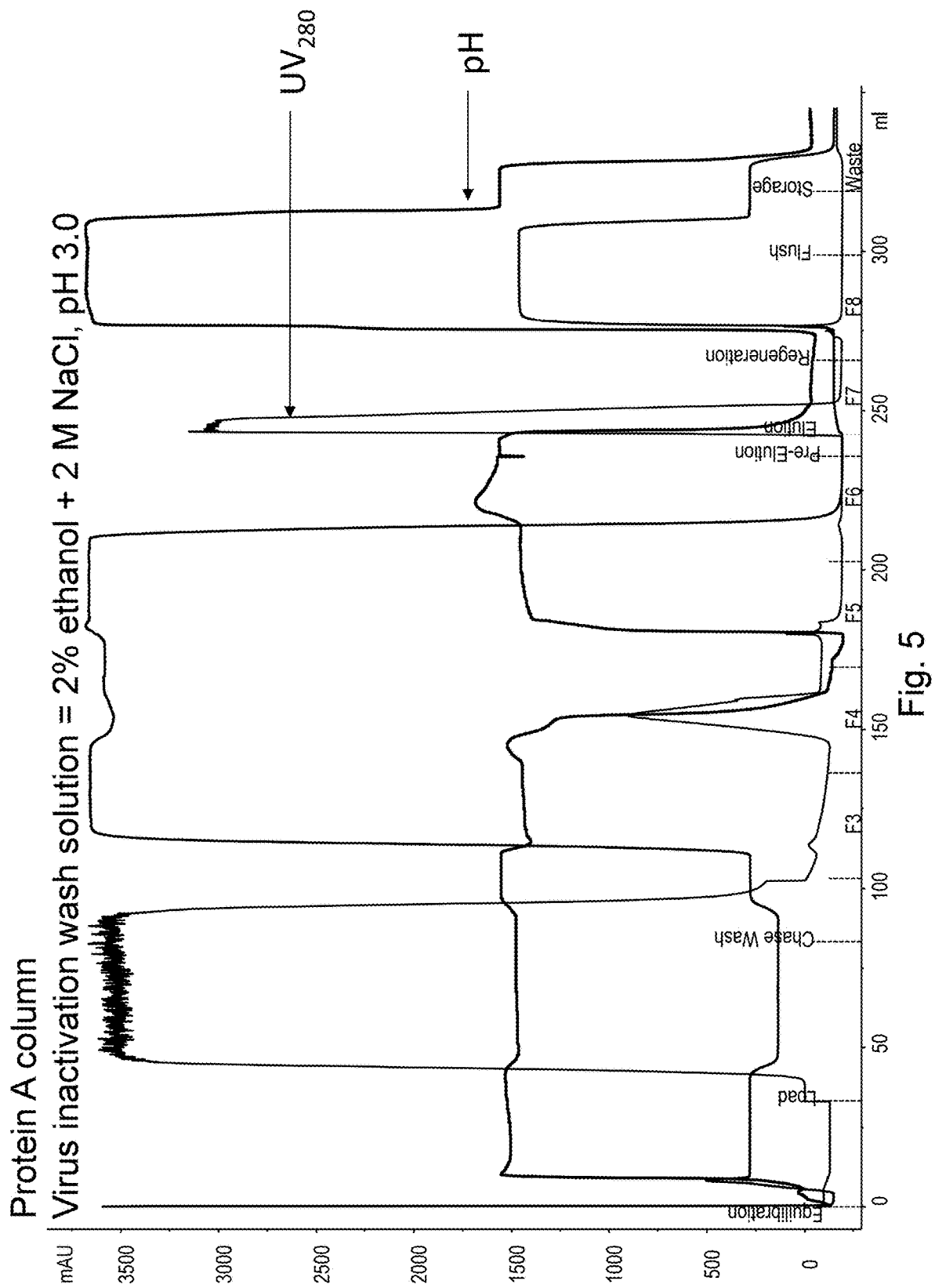

FIG. 5. The chromatogram showing the separation of proteins in a Protein A chromatography column using a wash solution containing 2 M NaCl and 2% ethanol at pH 3.0. $UV_{280}$ indicates protein concentration in the collected fractions.

Figure 6:
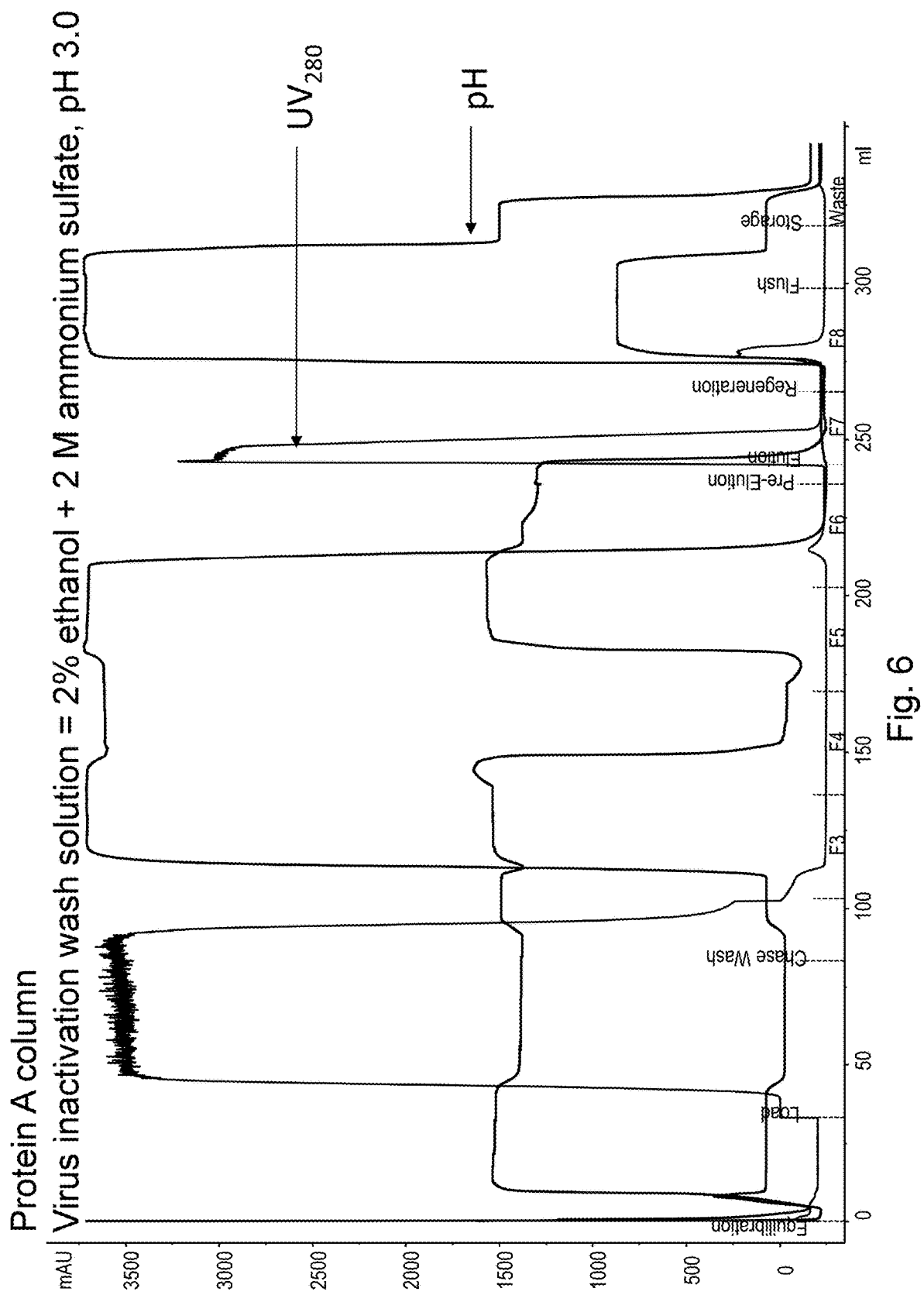

FIG. 6. The chromatogram showing the separation of proteins in a Protein A chromatography column using a wash solution containing 2 M ammonium sulfate and 2% ethanol at pH 3.0. $UV_{280}$ indicates protein concentration in the collected fractions.

Figure 7:
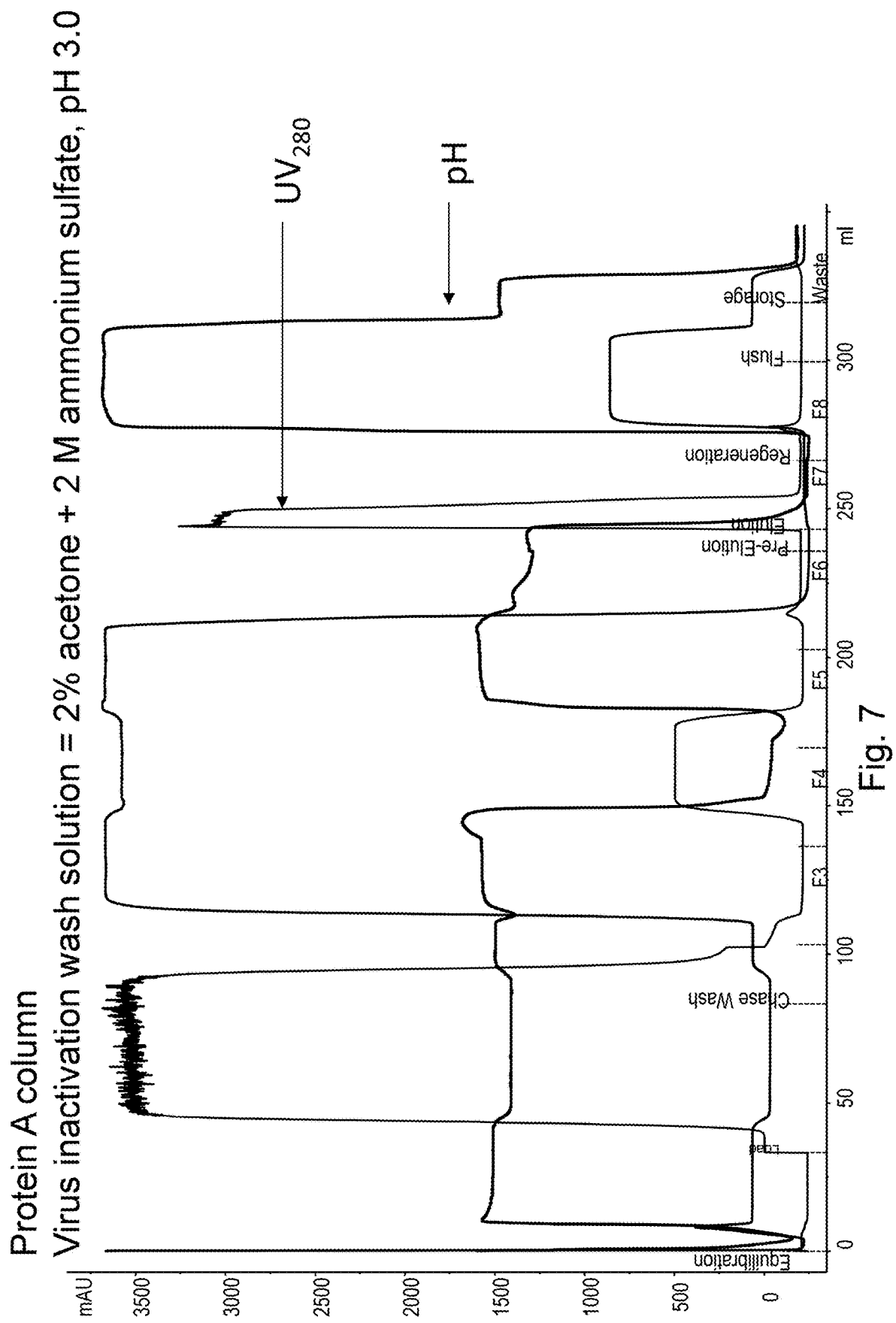

FIG. 7. The chromatogram showing the separation of proteins in a Protein A chromatography column using a wash solution containing 2 M ammonium sulfate and 2% acetone at pH 3.0. $UV_{280}$ indicates protein concentration in the collected fractions.

Figure 8:
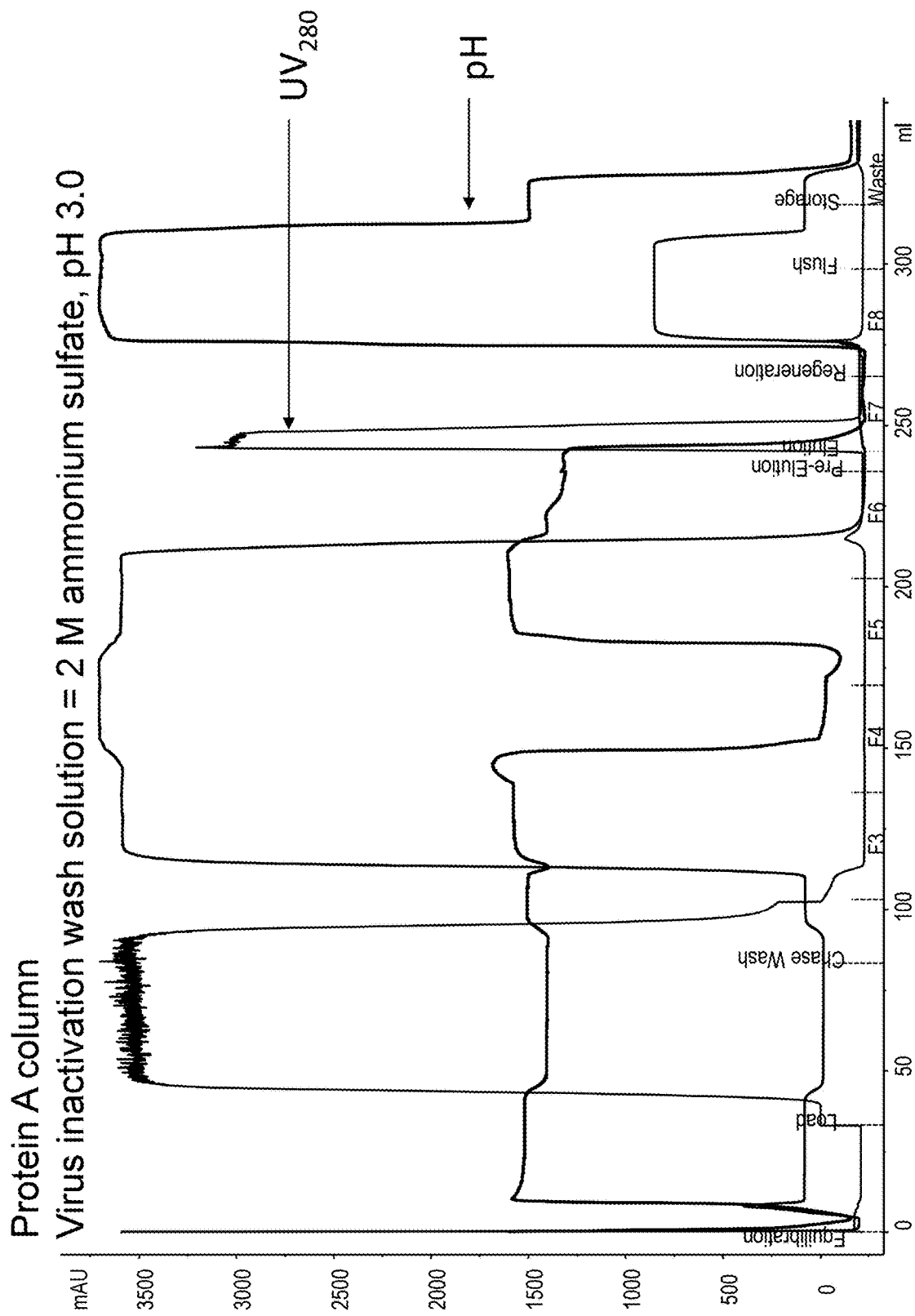

FIG. 8. The chromatogram showing the separation of proteins in a Protein A chromatography column using a wash solution containing 2 M ammonium sulfate at pH 3.0. $UV_{280}$ indicates protein concentration in the collected fractions.

Figure 9:
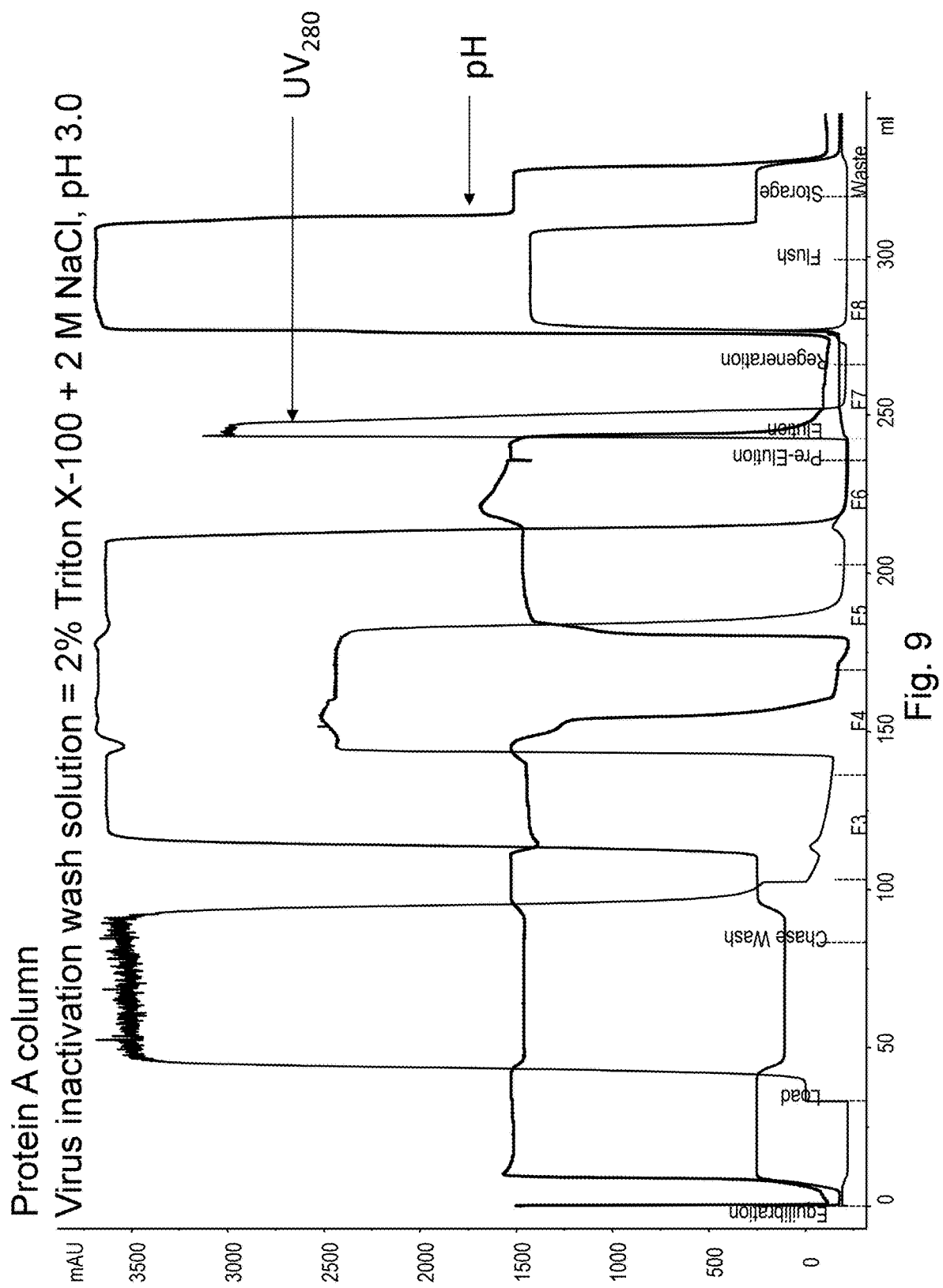

FIG. 9. The chromatogram showing the separation of proteins in a Protein A chromatography column using a wash solution containing 2 M ammonium sulfate and 2% TRITON™ X-100 at pH 3.0. $UV_{280}$ indicates protein concentration in the collected fractions.

Figure 10:
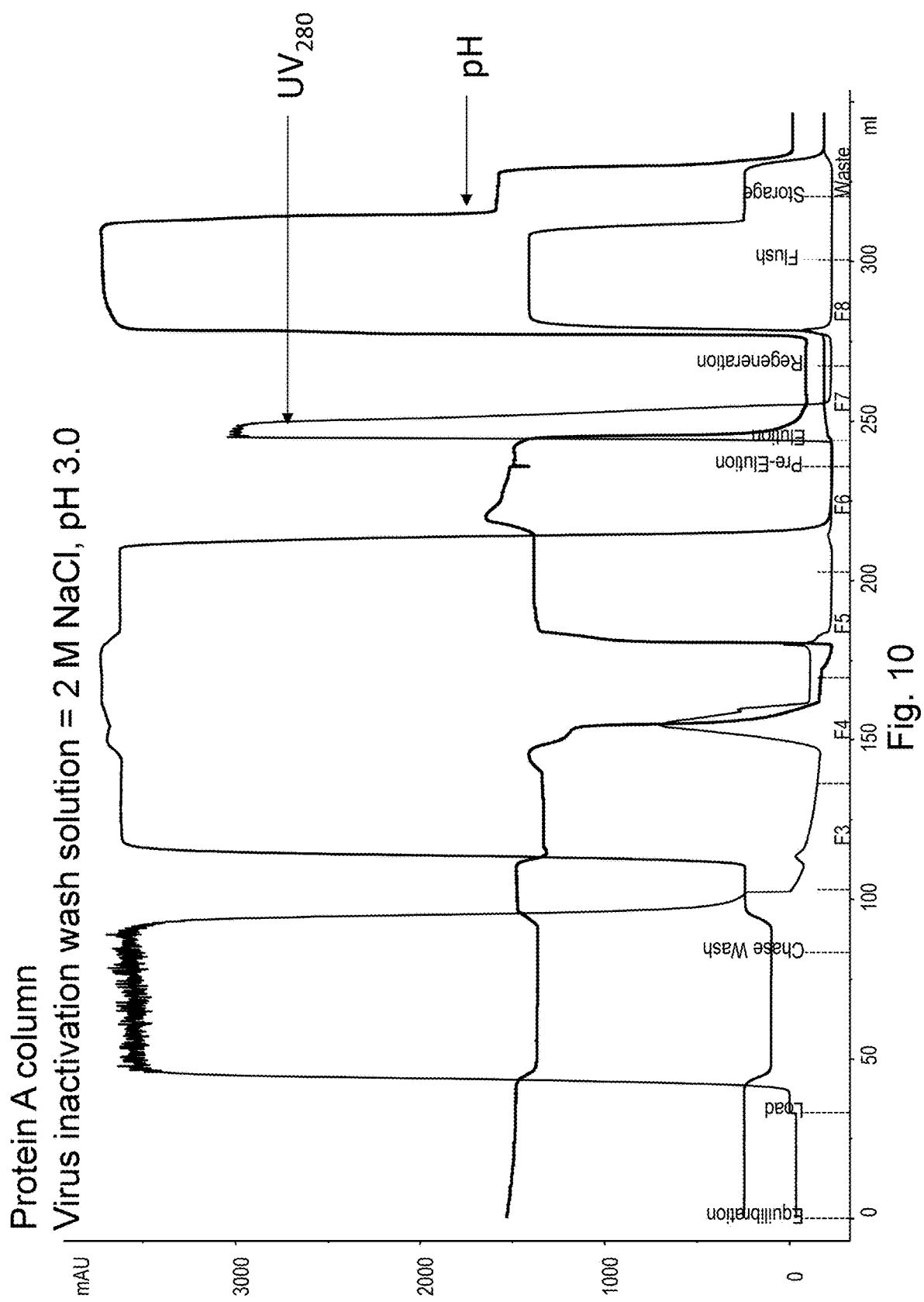

FIG. 10. The chromatogram showing the separation of proteins in a Protein A chromatography column using a wash solution containing 2 M NaCl at pH 3.0. $UV_{280}$ indicates protein concentration in the collected fractions.

Figure 11:
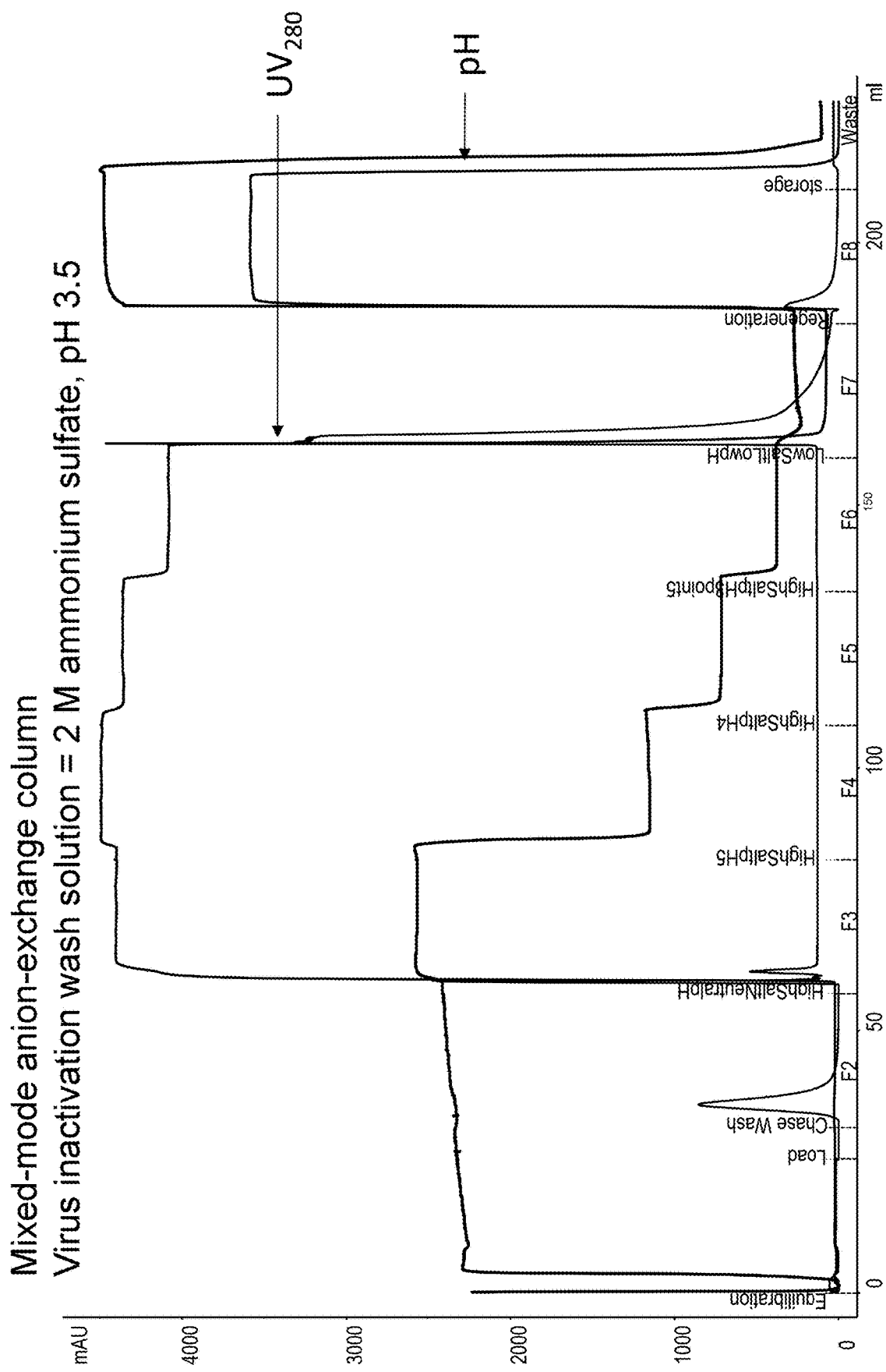

FIG. 11. The chromatogram showing the separation of proteins in a mixed-mode anion-exchange chromatography column using a wash solution containing 2 M ammonium sulfate at pH 3.5 and 4.0. $UV_{280}$ indicates protein concentration in the collected fractions.

Figure 12:
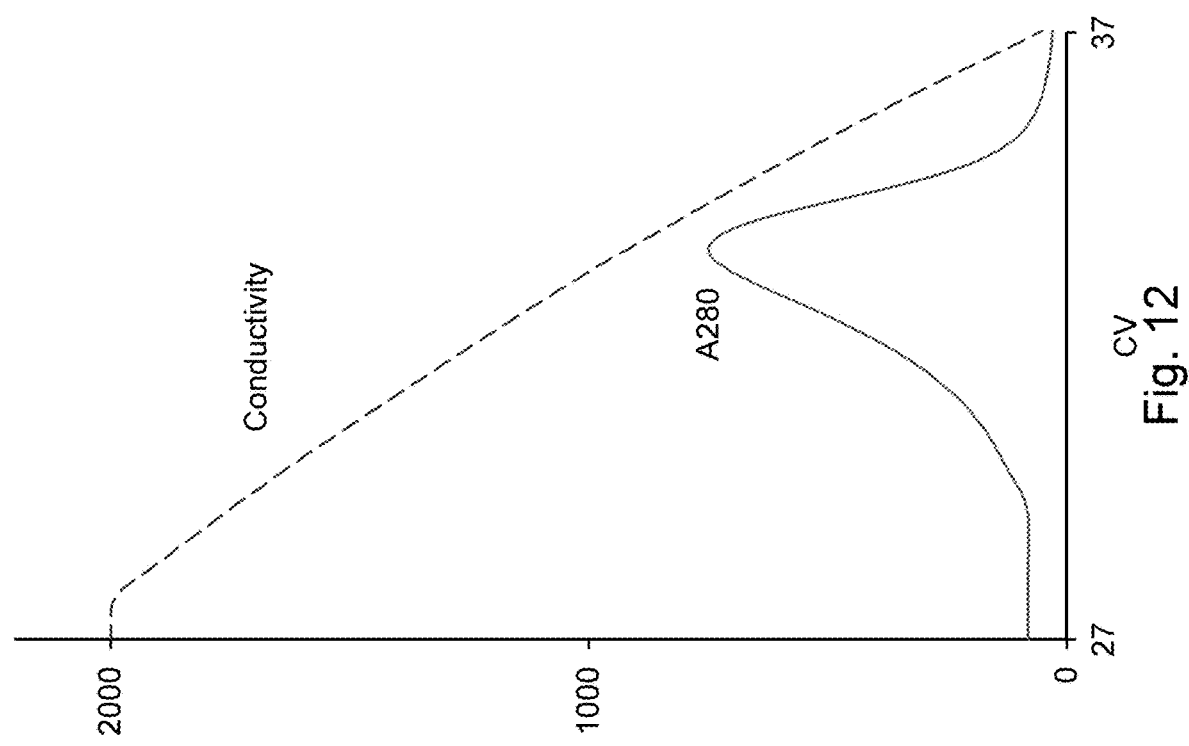

FIG. 12. The concentration of ammonium sulfate was reduced from 2 M to zero over a 9 CV gradient at pH 3.0 to determine the minimum concentration of ammonium sulfate required to keep the antibody bound to the protein A resin at low pH values. At least 1700 mM ammonium sulfate is required to keep the antibody bound to the resin at low pH.

Figure 13:
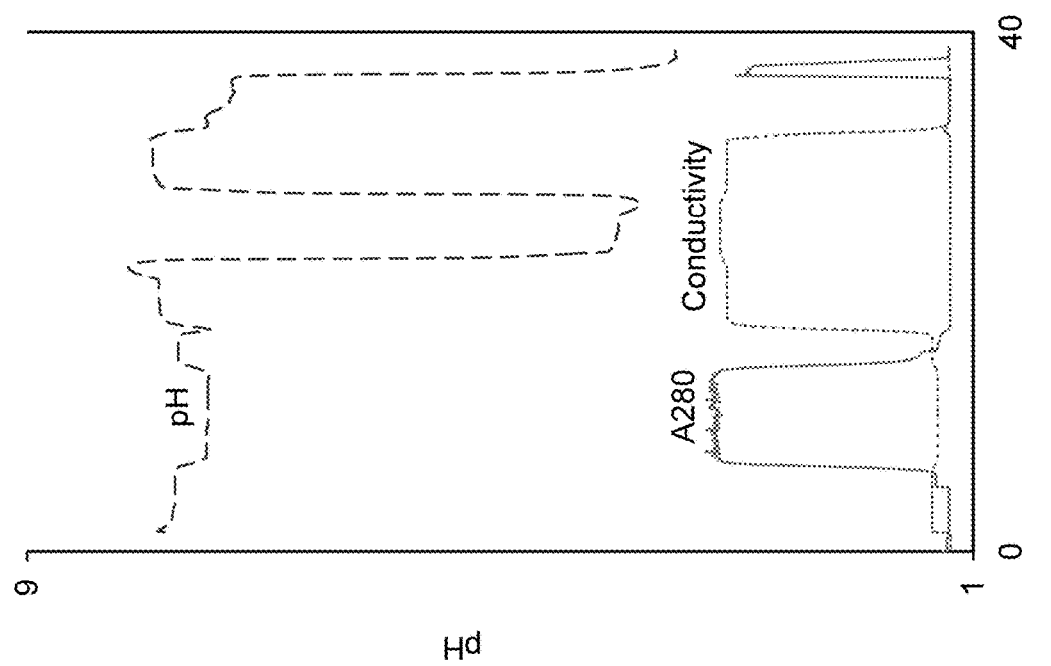

FIG. 13. Protein concentration, conductivity and pH versus column volumes using a pH 3.0, 2 M ammonium sulfate, 100 mM glycine wash. The high level of ammonium sulfate prevented the low pH elution of the antibody, potentially enabling on-column viral inactivation.

Figure 14:
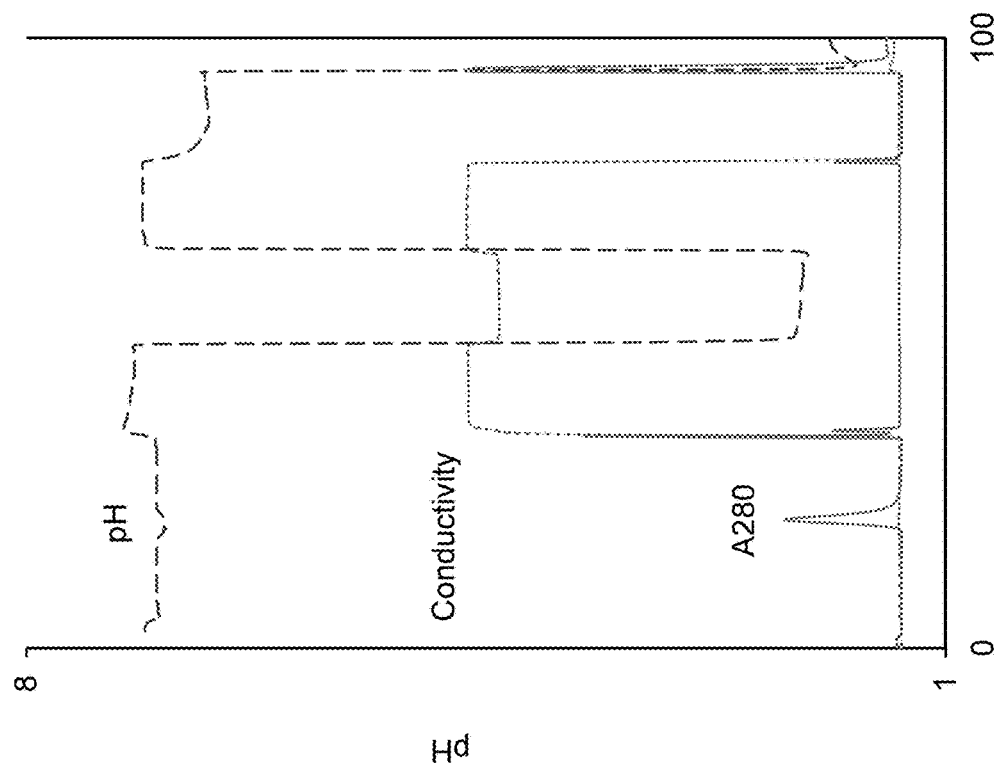

FIG. 14. Protein concentration, conductivity and pH versus column volumes using a pH 3.5, 2 M ammonium sulfate, 100 mM citrate wash to keep the antibody bound to the mixed mode anion exchange resin (Capto Adhere) resin at low pH.

Figure 15:
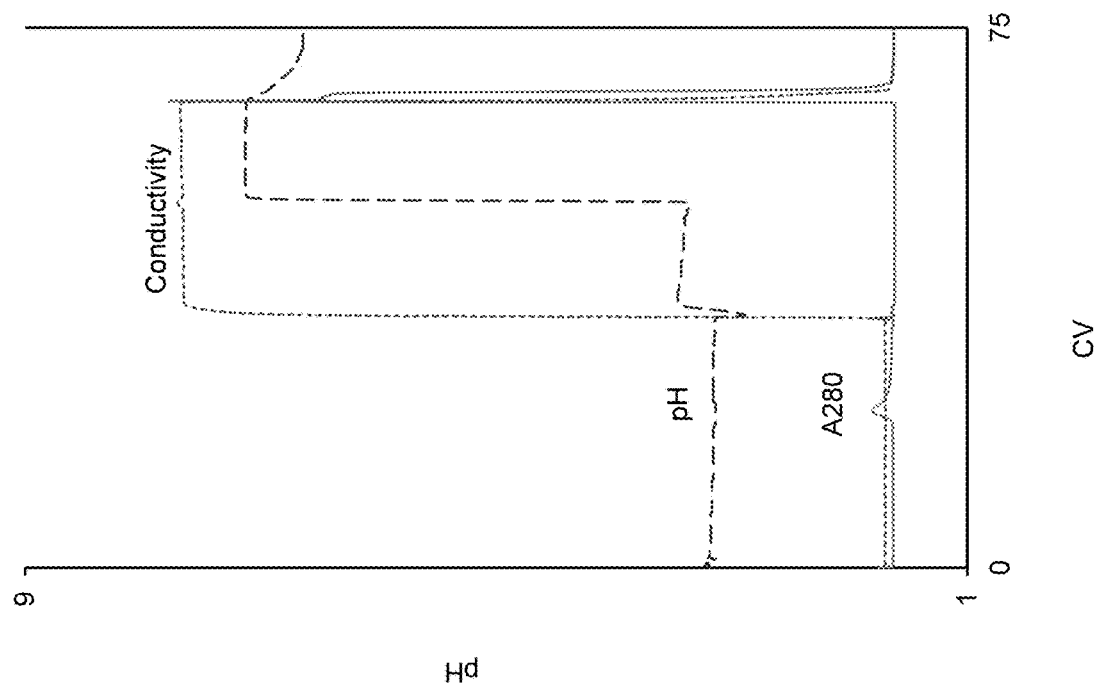

FIG. 15. Protein concentration, conductivity and pH versus column volumes using a pH 8.0, 2 M ammonium sulfate, 50 mM phosphate wash to keep the antibody bound to the mixed mode cation exchange resin (Capto MMC) resin at high pH.

DETAILED DESCRIPTION OF THE INVENTION

I. Definitions

Throughout this disclosure, the term "a" or "an" entity refers to one or more of that entity; for example, "a polypeptide," is understood to represent one or more polypeptides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the term "about" allows for the degree of variation inherent in the methods and in the instrumentation used for measurement or quantitation. For example, depending on the level of precision of the instrumentation used, standard error based on the number of samples measured, and rounding error, the term "about" includes, without limitation, ±10%.

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit, the terms "polypeptide" and "protein" as used herein are used interchangeably. If discrete functional unit is comprised of more than one polypeptide that physically associate with one another, the term "protein" as used herein refers to the multiple polypeptides that are physically coupled and function together as the discrete unit. Thus, as used herein, a "peptide," a "peptide fragment," a "protein," an "amino acid chain," an "amino acid sequence," or any other term used to refer to a chain or chains of two or more amino acids, are generically included in the definition of a "polypeptide," even though each of these terms can have a more specific meaning. The term "polypeptide" can be used instead of, or interchangeably with any of these terms. The term further includes polypeptides which have undergone post-translational or post-synthesis modifications, for example, glycosylation, acetylation, phosphorylation, amidation, derivatization by known protecting/blocking groups, proteolytic cleavage, or modification by non-naturally occurring amino acids.

"Recombinantly expressed polypeptide" and "recombinant polypeptide" as used herein refer to a polypeptide expressed from a host cell that has been genetically engineered to express that polypeptide. The recombinantly expressed polypeptide can be identical or similar to polypeptides that are normally expressed in the host cell. The recombinantly expressed polypeptide can also be foreign to the host cell, i.e., heterologous to peptides normally expressed in the host cell. Alternatively, the recombinantly expressed polypeptide can be chimeric in that portions of the polypeptide contain amino acid sequences that are identical or similar to polypeptides normally expressed in the host cell, while other portions are foreign to the host cell. Host cells include, but are not limited to, prokaryotic cells, eukaryotic cells, plant cells, yeast cells, animal cells, insect cells, avian cells, and mammalian cells. As used herein, the terms "recombinantly expressed polypeptide" and "recombinant polypeptide" also encompasses an antibody produced by a hybridoma.

The term "expression" or "expresses" are used herein to refer to transcription and translation occurring within a host cell. The level of expression of a product gene in a host cell can be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook et al., Molecular Cloning: A Laboratory Manual, pp. 7.3-7.57 (Cold Spring Harbor Laboratory Press, 1989). Protein encoded by a product gene can be quantitated either by assaying for the biological activity of the protein or by employing assays that are independent of such activity, such as western blotting, ELISA, HPLC, forteBIO, Bradford assay, absorbance at 280 nm, or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

The term "solution" refers to a mixture of one or more liquids (solvents) with one or more solids (solutes), such as a salt, a polymer, or a polypeptide. As used herein, a solution includes a buffer solution.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). Many buffers are known in the art for use in buffer solutions and include, but are not limited to, histidine, citrate, phosphate, succinate, tris(hydroxymethyl)aminomethane (Tris), acetate, glycine, aconitate, maleate, phthalate, cacodylate, barbitol, 2-(N-morpholino)ethanesulfonic acid (MES), bis (2-hydroxyethyl)imino-tris-(hydroxymethyl)methane (Bistris), N-(2-Acetamido)iminodiacetic acid (ADA), piperazine-N,N"-bis(2-ethanesulfonic acid) (PIPES), 1,3-bis[tris (hydroxymethyl)-methyl amino]propane (Bistrispropane), N-(Acetamido)-2-aminoethanesulfonic acid (ACES), 3-(N-morpholino)propanesulfonic acid (MOPS), N,N'-bis(2-hydroxyethyl)-2-amino-ethanesulfonic acid (BES), N-tris(hydroxymethyl)methyl-2-amino-ethanesulfonic acid (TES), N-2-hydroxyethylpiperazine-N'-ethanesulfonic acid (HEPES), N-2-hydroxyethylpiperazine-N'-propanesulfonic acid (HEPPS), N-tris(hydroxymethyl)methylglycine (Tricine), N,N-bis(2-hydroxyethyl)glycine (Bicine), glycylglycine, N-tris(hydroxymethyl)methyl-3-amino-propanesulfonic acid (TAPS), 1,3-bis[tris(hydroxymethyl)-methylamino] propane (Bistrispropane), as well as combinations of these.

The term "loading buffer" refers to the buffer, in which the polypeptide being purified is applied to a purification device, e.g., a chromatography column or a filter cartridge. Typically, the loading buffer is selected so that separation of the polypeptide of interest from unwanted impurities can be accomplished.

The terms "wash solution" and "wash buffer" are used interchangeably herein and refer to the buffer used to remove contaminant(s), such as process-related impurities, from the polypeptide-bound purification device (e.g., a chromatography matrix) without removing significant amounts of the polypeptide of interest. The wash solution can comprise a salt, a detergent, a solvent, a polymer, or any combinations thereof.

The terms "elution solution" and "elution buffer" are used interchangeably herein and refer to the buffer, which is typically used to remove (elute) the polypeptide of interest from the purification device (e.g., a chromatographic column or filter cartridge) to which it was applied earlier. Typically, the elution solution is selected so that separation of the polypeptide of interest from unwanted impurities can be accomplished. Often, the concentration of a particular ingredient, such as a particular salt (e.g. NaCl) in the elution is varied during the elution procedure (gradient). The gradient can be continuous or stepwise (interrupted by hold periods). In certain embodiments, low pH, such as a pH value below 4.5, is used in an elution solution.

The term "chromatography" refers to the process by which a solute of interest, typically a polypeptide, in a mixture is separated from other solutes in a mixture as a result of differences in rates at which the individual solutes of the mixture migrate through a stationary medium under the influence of a moving phase, or in bind and elute processes. The chromatography steps of the present invention can employ any type of chromatographic method. For example, such methods include without limitation:gas chromatography, liquid chromatography (e.g., high performance liquid chromatography); affinity chromatography (such as Protein-A or antibody-antigen affinity chromatography); supercritical fluid chromatography; ion exchange chromatography (such as anion or cation exchange chromatography); size-exclusion chromatography; reversed phase chromatography; two-dimensional chromatography; simulated moving bed chromatography, pyrolysis gas chromatography, fast protein (FPLC) chromatography; countercurrent chromatography; chiral chromatography; aqueous normal phase (ANP) chromatography; mixed mode chromatography; and, pseudo-affinity chromatography.

Any or all chromatographic steps of the invention can be carried out by any mechanical means. Chromatography can be carried out in a column. The column can be run with or without pressure and from top to bottom or bottom to top. The direction of the flow of fluid in the column can be reversed during the chromatography process. Chromatography can also be carried out using a batch process in which the solid support is separated from the liquid used to load, wash, and elute the sample by any suitable means, including gravity, centrifugation, or filtration. Chromatography can also be carried out by contacting the sample with a filter that absorbs or retains some molecules in the sample more strongly than others.

The term "affinity chromatography" refers to a protein separation technique in which a polypeptide of interest is reversibly and specifically bound to a biospecific ligand. Preferably, the biospecific ligand is covalently attached to a chromatographic solid phase material and is accessible to the polypeptide of interest in solution as the solution contacts the chromatographic solid phase material. The polypeptide of interest (e.g., antibody, enzyme, or receptor protein) retains its specific binding affinity for the biospecific ligand (antigen, substrate, cofactor, or hormone, for example) during the chromatographic steps, while other solutes and/or proteins in the mixture do not bind appreciably or specifically to the ligand. Binding of the polypeptide of interest to the immobilized ligand allows contaminating proteins or protein impurities to be passed through the chromatographic medium while the protein of interest remains specifically bound to the immobilized ligand on the solid phase material. The specifically bound polypeptide of interest is then removed in active form from the immobilized ligand with low pH, high pH, high salt, competing ligand, and the like, and passed through the chromatographic column with the elution buffer, free of the contaminating proteins or protein impurities that were earlier allowed to pass through the column. Any component can be used as a ligand for purifying its respective specific binding protein, e.g. antibody.

The terms "Protein A" and "ProA" are used interchangeably herein and encompasses Protein A recovered from a native source thereof, Protein A produced synthetically (e.g. by peptide synthesis or by recombinant techniques), and variants thereof which retain the ability to bind proteins which have a CH2/CH3 region, such as an Fc region. Protein A can be purchased commercially, for example, from Repligen, Pharmacia and Fermatech. Protein A is generally immobilized on a solid phase support material. The term "ProA" also refers to an affinity chromatography resin or column containing chromatographic solid support matrix to which is covalently attached Protein A.

In practice, Protein A chromatography involves using Protein A immobilized to a solid support. Protein G and Protein LG can also be used for affinity chromatography. The solid support is a non-aqueous matrix onto which Protein A adheres. Such supports include agarose, sepharose, glass, silica, polystyrene, collodion charcoal, sand, and any other suitable material. Such materials are well known in the art. Any suitable method can be used to affix the second protein to the solid support. Methods for affixing proteins to suitable solid supports are well known in the art. Such solid supports, with and without immobilized Protein A, are readily available from many commercial sources including such as Vector Laboratory (Burlingame, CA), Santa Cruz Biotechnology (Santa Cruz, CA), BioRad (Hercules, CA), Amersham Biosciences (part of GE Healthcare, Uppsala, Sweden) and Millipore (Billerica, MA). Protein A immobilized to a pore glass matrix is commercially available as PROSEP®-A (Millipore). The solid phase can also be an agarose-based matrix. Protein A immobilized on an agarose matrix is commercially available as MABSELECT™ (GE Healthcare, Uppsala, Sweden).

The term "mixed-mode chromatography" refers to a purification process using mixed mode adsorbents which provide multiple modes of interaction, such as hydrophobic, cation exchange, anion exchange, and hydrogen bonding interaction between the polypeptide of interest and the adsorbent ligands. A mixed-mode anion exchange resin is one that has both anion exchange groups and hydrophobic groups on the ligand. Commercially available mixed mode chromatography resins include, but are not limited to, CAPTO™ MMC, CAPTO™ MMC ImpRes, CAPTO™ Blue, BLUE SEPHAROSE™ 6 Fast Flow, CAPTO™ Adhere, and CAPTO™ Adhere ImpRes from GE Healthcare Life Sciences, or ESHMUNO® HCX from EMD Millipore, or NUVIA™ cPrime, CHT™ Ceramic Hydroxyapatite, and CFT™ Ceramic Fluoroapatite from Bio-Rad.

The terms "anion exchange resin," "anion exchange adsorbent," or "anion exchange matrix" are used herein to refer to a solid phase which is positively charged, e.g. having one or more positively charged ligands, such as quaternary amino groups, attached thereto. Commercially available anion exchange resins include DEAE SEPHAROSE™ Fast Flow, Q SEPHAROSE™ Fast Flow, Q SEPHAROSE™ High Performance, Q SEPHAROSE™ XL, CAPTO™ DEAE, CAPTO™ Q, and CAPTO™ Q ImpRes from GE Healthcare Life Sciences, or FRACTOGEL® EMD TMAE HiCap, FRACTOGEL® EMD DEAE, and ESHMUNO® Q from EMD Millipore, or UNOSPHERE™ Q and NUVIA™ Q from Bio-Rad.

The terms "cation exchange resin," "cation exchange adsorbent," or "cation exchange matrix" refer to a solid phase which is negatively charged, and which thus has free cations for exchange with cations in an aqueous solution passed over or through the solid phase. A negatively charged ligand attached to the solid phase to form the cation exchange resin can, e.g., be a carboxylate or sulfonate. Commercially available cation exchange resins include carboxy-methyl-cellulose, sulphopropyl (SP) immobilized on agarose (e.g. SP SEPHAROSE™ XL, SP-SEPHAROSE™ Fast Flow, SP SEPHAROSE™ High Performance, CM SEPHAROSE™ Fast Flow, CM SEPHAROSE™ High Performance, CAPTO™ S, and CAPTO™ SP ImpRes from GE Healthcare Life Sciences, or FRACTOGEL® EMD SE HiCap, FRACTOGEL® EMD SOS$^{3-}$, FRACTOGEL® EMD COO$^-$, ESHMUNO® S, and ESHMUNO® CPX from EMD Millipore, or UNOSPHERE™ S and NUVIA™ S from Bio-Rad).

As used herein, the terms "substantially reduce the elution of the polypeptide" or "substantial reduction of the polypeptide elution" are intended to mean that less than 30% of the target polypeptide is eluted from the chromatography matrix in a low pH and high salt wash solution. In one embodiment, less than 25%, less than 20%, less than 15%, less than 10%, or less than 5% of the target polypeptide is eluted from the chromatography matrix in a low pH high salt wash solution.

As used herein, the terms "percent recovery" and "percent purity," are intended to mean the recovery or purity achieved when a target compound (e.g., a protein) is conveyed through a purification step or procedure, compared to the quantity or purity of the target compound in the sample prior to the purification step or procedure. Achieving an increase in percent purity entails obtaining a product with reduced levels of contaminants (in proportion to the target compound) when a sample is compared before and after a purification step or procedure. Preferred percentages within the meaning of percent recovery and percent purity as defined above include, without limitation, at least about 50%, at least about 60%, at least about 70%, at least about 80%, at least about 90%, at least about 95%, at least about 98%, and at least about 99%.

Methods for the determination of yield or purity of a polypeptide are known to those of skill in the art. Yield or purity of a polypeptide can be determined by any suitable, art-recognized method of analysis (e.g., band intensity on a silver stained gel, polyacrylamide gel electrophoresis, ELISA, HPLC and the like). An exemplary method is size-exclusion chromatography (SEC) high-performance liquid chromatography (HPLC), described herein below. Purity can be determined using relative "area under the curve" (AUC) values, which can typically be obtained for peaks in a chromatogram, such as an HPLC chromatogram. Optionally, purities are determined by chromatographic or other means using a standard curve generated using a reference material of known purity. Purity can also be determined on a weight-by-weight basis.

As used herein, the term "inactivate" or other forms of this word (e.g., inactivation, inactivated, inactivates, etc.) when used in reference to viruses is intended to indicate not only complete virus inactivation (i.e., no detectable infectious virus) but also the detectable reducing or reduction of infectious virus titers (i.e., lowering or lowered levels of detectable infectious virus). Thus, the reducing or reduction of infectious virus titers is included within the meaning of "virus inactivation" (and other forms of this term) whether or not such reducing or reduction is explicitly stated herein. Quantification methods for viral inactivation are well known in the art. Methods such as plaque assays can be used. Plaque assays determine the number of plaque forming units (pfu) in a virus sample, assuming that each plaque formed is representative of one infective virus particle or TCID50 assays, where an endpoint dilution assay quantifies the amount of virus required to kill 50% of infected hosts or to produce a cytopathic effect in 50% of inoculated tissue culture cells.

The term "polymer" refers to a molecule formed by covalent linkage of two or more monomers, where the monomers are not amino acids. Non-limiting examples of polymers include polyethyl glycol, polypropyl glycol, and copolymers of ethylene and propylene glycol.

The term "detergent" refers to nonionic or zwitterionic surfactants such as polysorbates (e.g. polysorbates 20 or 80); poloxamers (e.g. poloxamer 188); octylphenol ethylene oxide condensate (also known as Octoxynol-9, t-octylphenoxypolyethoxyethanol, TRITON™, or TRITON™ X-100); 3-[(3-cholamidopropyl)dimethylammonio]-1-propane-sulfonate (CHAPS); 3-[(3-cholamidopropyl)dimethylammonio]-2-hydroxy-1-propanesulfonate (CHAPSO); sodium dodecyl sulfate (SDS), sodium laurel sulfate, sodium octyl glycoside; lauryl-, myristyl-, linoleyl- or stearyl-sulfobetaine; lauryl-, myristyl-, linoleyl- or stearyl-sarcosine; linoleyl-, myristyl-, or cetyl-betaine, lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and 1-ethyl-1-(2-hydroxyethyl)-2-isoheptadecylimidazolinium ethylsulfate (e.g., the MONAQUAT™ series, Mona Industries, Inc., Paterson, New Jersey). Non-limiting examples of commercial products comprising compounds similar to TRITON™ X-100 include CONCO™ NI, DOWFAX™ 9N, IGEPAL™ CO, MAKON™, NEUTRONYX® 600's, NONIPOL™ NO, POLYTERGENT® B, RENEX™ 600's, SOLAR™ NO, STEROX™, SERFONIC™ N, T-DET-N™, TERGITOL™ NP, and TRITON™ N.

The term "antibody" is used to mean an immunoglobulin molecule that recognizes and specifically binds to a target, such as a protein, polypeptide, peptide, carbohydrate, polynucleotide, lipid, or combinations of the foregoing etc., through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively.

The term "Fc-containing polypeptide" as used herein refers to a protein in which one or more polypeptides are linked to an Fc region or a variant or derivative thereof. The term "Fc" or "Fc region" refers to a C-terminal region of an IgG heavy chain, including any functional variants of IgG Fc that retains the ability of binding to Protein A. One example of an Fc-containing polypeptide is ENBREL® (etanercept) which is a fusion protein fusing a tumor necrosis factor (TNF) receptor to the constant end of the IgG1 antibody.

The term "CH2/CH3-containing polypeptide" as used herein refers to a protein in which one or more polypeptides are linked to the CH2/CH3 domains of an IgG heavy chain, or a functional variant or derivative thereof.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the invention with an immunoglobulin Fc domain. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

The term "linked" as used herein refers to a first amino acid sequence covalently or non-covalently joined to a second amino acid sequence. The term "covalently linked" or "covalent linkage" refers to a covalent bond, e.g., a disulfide bond, a peptide bond, or one or more amino acids, e.g., a linker, between the two moieties that are linked together. The first amino acid sequence can be directly joined or juxtaposed to the second amino acid sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively).

The term "heterologous moiety" refers to a polypeptide or other moiety which is derived from a distinct entity from that of the entity to which it is being compared. For instance, a heterologous polypeptide can be synthetic, or derived from a different species, different cell type of an individual, or the same or different type of cell of distinct individuals. In one embodiment, a heterologous moiety can be a polypeptide fused to another polypeptide to produce a fusion polypeptide or protein. In another embodiment, a heterologous moiety can be a non-polypeptide such as PEG conjugated to a polypeptide or protein.

The term "monomer-dimer hybrid" used herein refers to a chimeric protein comprising a first polypeptide chain and a second polypeptide chain, which are associated with each other by a covalent bond, wherein the first chain comprises a biologically active molecule, e.g., a clotting factor such as Factor IX, Factor VIII, or Factor VII, and an Fc region, and the second chain comprises, consists essentially of, or consists of an Fc region without the clotting factor. The monomer-dimer hybrid construct thus is a hybrid comprising a monomer aspect having only one biologically active molecule and a dimer aspect having two Fc regions.

As used herein, the term "half-life" refers to a biological half-life of a particular polypeptide in vivo. Half-life can be represented by the time required for half the quantity administered to a subject to be cleared from the circulation and/or other tissues in the animal.

The term "hybridoma" as used herein refers to a cell created by fusion of an immortalized cell derived from an immunologic source and an antibody-producing cell. The resulting hybridoma is an immortalized cell that produces antibodies. The individual cells used to create the hybridoma can be from any mammalian source, including, but not limited to, rat, hamster, pig, rabbit, sheep, pig, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., *Nature*, 537:3053 (1983)).

II. Production and Purification of Polypeptides of Interest

A. Polypeptides of Interest

The present invention can be used to inactivate virus that is present during production of any polypeptide that is expressed in a host cell. The polypeptide can be expressed from a gene that is endogenous to the host cell, or from a gene that is introduced into the host cell through genetic engineering. The polypeptide can be one that occurs in nature, or can alternatively have a sequence that was engineered or selected by the hand of man. An engineered polypeptide can be assembled from other polypeptide segments that individually occur in nature, or can include one or more segments that are not naturally occurring.

A polypeptide of interest often has a desirable biological or chemical activity. For example, the present invention can be employed to inactivate virus that is present during the production of a pharmaceutically or commercially relevant enzyme, receptor, antibody, hormone, regulatory factor, antigen, binding agent, etc.

The following is a detailed description of some of the polypeptides that can be expressed in a cell culture and purified in accordance with the virus inactivation method of the present invention.

Clotting Factors

In some embodiments, the protein of interest comprises a clotting factor. Clotting factor, as used herein, means any molecule, or analog thereof, which prevents or decreases the duration of a bleeding episode in a subject with a hemostatic disorder. For example, a clotting factor used in the invention can be a full-length clotting factor, a mature clotting factor, or a chimeric clotting factor. In other words, it means any molecule having clotting activity. Clotting activity, as used herein, means the ability to participate in a cascade of biochemical reactions that culminates in the formation of a fibrin clot and/or reduces the severity, duration or frequency of hemorrhage or bleeding episode. Examples of clotting factors can be found in U.S. Pat. No. 7,404,956, which is herein incorporated by reference.

The clotting factor can be a factor that participates in the extrinsic pathway. The clotting factor can be a factor that participates in the intrinsic pathway. Alternatively, the clotting factor can be a factor that participates in both the extrinsic and intrinsic pathway.

Non-limiting examples of clotting factors include factor I (fibrinogen), factor II (prothrombin), Tissue factor, factor V (proaccelerin, labile factor), factor VII (stable factor, proconvertin), factor VIII (Antihemophilic factor A), factor IX (Antihemophilic factor B or Christmas factor), factor X (Stuart-Prower factor), factor XI (plasma thromboplastin antecedent), factor XII (Hageman factor), factor XIII (fibrin-stabilizing factor), von Willebrand Factor (VWF), prekallikrein (Fletcher factor), high-molecular-weight kininogen (HMWK) (Fitzgerald factor), fibronectin, antithrombin III, heparin cofactor II, protein C, protein S, protein Z, plasminogen, alpha 2-antiplasmin, tissue plasminogen activator (tPA), urokinase, plasminogen activator inhibitor-1 (PAI1), and plasminogen activator inhibitor-2 (PAI2).

In one embodiment, the clotting factor can be a human clotting factor or a non-human clotting factor, e.g., derived from a non-human primate, a pig or any mammal. The clotting factor can be chimeric clotting factor, e.g., the clotting factor can comprise a portion of a human clotting factor and a portion of a porcine clotting factor or a portion of a first non-human clotting factor and a portion of a second non-human clotting factor.

In another embodiment, the clotting factor can be an activated clotting factor. Alternatively, the clotting factor can be an inactive form of a clotting factor, e.g., a zymogen. The inactive clotting factor can undergo activation subsequent to being linked to at least a portion of an immunoglobulin constant region. The inactive clotting factor can be activated subsequent to administration to a subject. Alternatively, the inactive clotting factor can be activated prior to administration.

Factor FIX

"Factor IX protein" or "FIX protein" as used herein, means functional Factor FIX protein in its normal role in coagulation, unless otherwise specified. Thus, the FIX polypeptide includes variant polypeptides that are functional and the polynucleotides that encode such functional variant polypeptides. In one embodiment, the FIX polypeptides are the human, bovine, porcine, canine, feline, and murine FIX polypeptides. The full length polypeptide and polynucleotide sequences of FIX are known, as are many functional variants, e.g., fragments, mutants and modified versions. FIX polypeptides include full-length FIX, full-length FIX minus Met at the N-terminus, full-length FIX minus the signal sequence, mature FIX (minus the signal sequence and propeptide), and mature FIX with an additional Met at the N-terminus. FIX can be made by recombinant means ("recombinant Factor IX" or "rFIX"), i.e., it is not naturally occurring or derived from plasma.

A great many functional FIX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses FIX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant FIX molecules that exhibit increased protein stability, increased in vivo and in vitro half-life, and increased resistance to proteases at page 4, line 1 to page 19, line 11. WO 2007/149406 A2 also discloses chimeric and other variant FIX molecules at page 19, line 12 to page 20, line 9. International publication number WO 08/118507 A2, which is herein incorporated by reference in its entirety, discloses FIX mutants that exhibit increased clotting activity at page 5, line 14 to page 6, line 5. International publication number WO 09/051717 A2, which is herein incorporated by reference in its entirety, discloses FIX mutants having an increased number of N-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant FIX molecules that have an increased number of glycosylation sites, which result in an increased half-life, at page 4, line 26 to page 12, line 6. International publication number WO 09/140015 A2, which is herein incorporated by reference in its entirety, discloses functional FIX mutants that an increased number of Cys residues, which can be used for polymer (e.g., PEG) conjugation, at page 11, paragraph [0043] to page 13, paragraph [0053]. The FIX polypeptides described in International Application No. PCT/US2011/043569 filed Jul. 11, 2011 and published as WO 2012/006624 on Jan. 12, 2012 are also incorporated herein by reference in its entirety.

In one embodiment, the polypeptide of interest is a long-acting or long-lasting FIX polypeptide that is a chimeric polypeptide comprising a FIX polypeptide and an FcRn binding partner. In certain embodiments, the polypeptide of interest is rFIX-Fc which is a fusion protein comprising a single molecule of human recombinant coagulation FIX (rFIX) covalently linked to the dimeric Fc region of immunoglobulin G1 (IgG1) with no intervening sequence. The term "FcRn binding partner" is defined herein.

Factor VIII

"Factor VIII protein" or "FVIII protein" as used herein, means functional Factor VIII protein in its normal role in coagulation, unless otherwise specified. Thus, the term FVIII includes variant proteins that are functional. In one embodiment, the FVIII protein is the human, porcine, canine, rat, or murine FVIII protein. A functional FVIII protein can be a fusion protein, such as, but not limited to, a fusion protein comprising a fully or partially B domain-deleted FVIII, at least a portion of an immunoglobulin constant region, e.g., an Fc domain, or both. Myriad functional FVIII variants have been constructed and can be used as recombinant FVIII proteins as described herein. See PCT Publication Nos. WO 2011/069164 A2, WO 2012/006623 A2, WO 2012/006635 A2, or WO 2012/006633 A2, all of which are incorporated herein by reference in their entirety. FVIII can be a single chain FVIII or a dual chain FVIII.

A great many functional FVIII variants are known. In addition, hundreds of nonfunctional mutations in FVIII have been identified in hemophilia patients. See, e.g., Cutler et al., Hum. Mutat. 19:274-8 (2002), incorporated herein by reference in its entirety. In addition, comparisons between FVIII from humans and other species have identified conserved residues that are likely to be required for function.

See, e.g., Cameron et al., Thromb. Haemost. 79:317-22 (1998) and U.S. Pat. No. 6,251,632, incorporated herein by reference in their entirety.

The human FVIII amino acid sequence was deduced from cDNA as shown in U.S. Pat. No. 4,965,199, which is incorporated herein by reference in its entirety. Native mature human FVIII derived from the cDNA sequence (i.e., without the secretory signal peptide but prior to other post-translational processing) can be found as SEQ ID NO:1 in WO 2013/123457 A1, which is incorporated herein by reference in its entirety. Partially or fully B domain-deleted FVIII is functional and has been used in commercial FVIII therapeutics. See, e.g., EP 506757 B2, which is incorporated herein by reference in its entirety.

In one embodiment, the polypeptide of interest is a long-acting or long-lasting FVIII polypeptide that is a chimeric polypeptide comprising a FVIII polypeptide and an FcRn binding partner. In certain embodiments, the polypeptide of interest is rFVIII-Fc which is a fusion protein comprising a single molecule of human recombinant coagulation FVIII (rFVIII) covalently linked to the dimeric Fc region of immunoglobulin G1 (IgG1) with no intervening sequence.

Factor VII

"Factor VII protein" or "FVII protein" as used herein, means functional Factor VII protein in its normal role in coagulation, unless otherwise specified. It can be a mature form of Factor VII or a variant thereof. Factor VII is a serine protease that is part of the coagulation cascade. FVII includes a Gla domain, two EGF domains (EGF-1 and EGF-2), and a serine protease domain (or peptidase S1 domain) that is highly conserved among all members of the peptidase S1 family of serine proteases, such as for example with chymotrypsin. FVII occurs as a single chain zymogen, an activated zymogen-like two-chain polypeptide (e.g., activatable FVII) and a fully activated two-chain form.

As used herein, a "zymogen-like" protein or polypeptide refers to a protein that has been activated by proteolytic cleavage, but still exhibits properties that are associated with a zymogen, such as, for example, low or no activity, or a conformation that resembles the conformation of the zymogen form of the protein. For example, when it is not bound to tissue factor, the two-chain activated form of FVII is a zymogen-like protein; it retains a conformation similar to the uncleaved FVII zymogen, and, thus, exhibits very low activity. Upon binding to tissue factor, the two-chain activated form of FVII undergoes conformational change and acquires its full activity as a coagulation factor.

Exemplary FVII variants include those with increased specific activity, e.g., mutations that increase the activity of FVII by increasing its enzymatic activity (Kcat or Km). Such variants have been described in the art and include, e.g., mutant forms of the molecule as described for example in Persson et al., Proc. Natl. Acad Sci. USA 98:13583 (2001); Petrovan and Ruf, J. Biol. Chem. 276:6616 (2001); Persson et al., J. Biol. Chem. 276:29195 (2001); Soejima et al., J. Biol. Chem. 276:17229 (2001); Soejima et al., J. Biol. Chem. 247:49027 (2002).

In one embodiment, the polypeptide of interest is a long-acting or long-lasting FVII polypeptide that is a chimeric polypeptide comprising a FVII polypeptide and an FcRn binding partner. In certain embodiments, the polypeptide of interest is rFVII-Fc which is a fusion protein comprising a single molecule of human recombinant coagulation FVII (rFIX) covalently linked to the dimeric Fc region of immunoglobulin G1 (IgG1) with no intervening sequence.

Chimeric Clotting Factors

In certain embodiments, the polypeptide of interest comprises a chimeric clotting factor. In certain embodiments, the chimeric clotting factor comprises a clotting factor and a CH2/CH3 domain. CH2 and CH3 are two constant domains located in the Fc region of an IgG heavy chain. The CH2 domain of a human IgG Fc region usually extends from amino acids 231 to amino acid 341 according to the numbering system as described in Kabat et al. 1991, Sequences of Proteins of Immunological Interest, U. S. Department of Public Health, Bethesda; MD, incorporated herein by reference in its entirety. The CH3 domain of a human IgG Fc region usually extends from amino acids 342 to 447 according to the numbering system of Kabat et al., 1991. A CH2/CH3 domain includes any functional derivative or variants of the CH2 and CH3 domains.

In certain embodiments, the chimeric clotting factor comprises a clotting factor and an Fc region. In one embodiment, the chimeric clotting factor is FIX-Fc, FVIII-Fc, or FVII-Fc. Various examples of FIX-Fc, FVIII-Fc, or FVII-Fc chimeric and hybrid polypeptides are described, for example, in U.S. Pub. Nos. 2013/0202595 A1, 2013/0108629 A1, and U.S. Pat. No. 8,329,182, which are incorporated herein by reference in their entirety.

In one embodiment, the polypeptide of interest is a long-acting or long-lasting clotting factor that is a chimeric polypeptide comprising a clotting factor and an FcRn binding partner. In certain embodiments, the polypeptide of interest is a fusion protein comprising a single molecule of human recombinant clotting factor covalently linked to the dimeric Fc region of immunoglobulin G1 (IgG1) with no intervening sequence.

Heterologous Moieties

In certain embodiments, the polypeptide of interest is a chimeric polypeptide comprising a biologically active molecule and at least one heterologous moiety. In one embodiment, the biologically active molecule is a clotting factor. In one embodiment, the heterologous moiety is capable of extending the half-life of the clotting factor.

In certain embodiments, the heterologous moiety is an IgG or a fragment thereof, an albumin or a fragment thereof, an albumin binding moiety, a PAS sequence, a homo-amino acid polymer (HAP) sequence, transferrin or a fragment thereof, and any combinations thereof, or a non-polypeptide moiety comprising polyethylene glycol (PEG), polysialic acid, hydroxyethyl starch (HES), a derivative thereof, and any combinations thereof.

In one embodiment, the heterologous moiety comprises a first Fc region. In another embodiment, the heterologous moiety comprises a second Fc region.

As used herein, the term "Fc region" is defined as the portion of a polypeptide which corresponds to the Fc region of native immunoglobulin, i.e., as formed by the dimeric association of the respective Fc domains of its two heavy chains. A native Fc region forms a homodimer with another Fc region.

In one embodiment, the "Fc region" refers to the portion of a single immunoglobulin heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc region comprises at least a hinge domain, a CH2 domain, and a CH3 domain.

The Fc region of an immunoglobulin constant region, depending on the immunoglobulin isotype can include the CH2, CH3, and CH4 domains, as well as the hinge region. Chimeric proteins comprising an Fc region of an immunoglobulin bestow several desirable properties on a chimeric protein including increased stability, increased serum half-life (see Capon et al., 1989, Nature 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entirety.

In another embodiment, the "Fc region" includes an amino acid sequence of an Fc domain or derived from an Fc domain. In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

The Fc regions of the invention may employ art-recognized Fc variants which are known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) can be made.

In certain embodiments, a chimeric polypeptide used in accordance with the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention may comprise or consist of an FcRn binding portion. FcRn binding portions may be derived from heavy chains of any isotype, including IgG1, IgG2, IgG3 and IgG4.

FcRn binding partner ("FcRn BP") comprises functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term FcRn BP includes any variants of IgG Fc that are functional. For example, the region of the Fc portion of IgG that binds to the FcRn receptor has been described based on X-ray crystallography (Burmeister et al. 1994, Nature 372:379, incorporated herein by reference in its entirety). The major contact area of the Fc with the FcRn is near the junction of the CH2 and CH3 domains. Fc-FcRn contacts are all within a single Ig heavy chain. FcRn BPs include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. The FcRn receptor has been isolated from several mammalian species including humans. The sequences of the human FcRn, rat FcRn, and mouse FcRn are known (See, e.g., Story et al. 1994, J. Exp. Med. 180: 2377, incorporated herein by reference in its entirety). An FcRn BP can comprise the CH2 and CH3 domains of an immunoglobulin with or without the hinge region of the immunoglobulin. Exemplary FcRn BP variants are provided in WO 2004/101740 and WO 2006/074199, incorporated herein by reference in its entirety.

In certain embodiments, the heterologous moiety is an albumin or a fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Further examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are herein incorporated by reference in their entirety.

In certain embodiments, the heterologous moiety is an albumin binding moiety, which comprises an albumin binding peptide, a bacterial albumin binding domain, an albumin-binding antibody fragment, or any combinations thereof. For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998)

J. Immunol. Methods 218, 73-83). Other examples of albumin binding peptides that can be used as conjugation partner are, for instance, those having a Cys-Xaa 1-Xaa 2-Xaa 3-Xaa 4-Cys consensus sequence, wherein Xaa 1 is Asp, Asn, Ser, Thr, or Trp; Xaa 2 is Asn, Gln, H is, Ile, Leu, or Lys; Xaa 3 is Ala, Asp, Phe, Trp, or Tyr; and Xaa 4 is Asp, Gly, Leu, Phe, Ser, or Thr as described in US patent application 2003/0069395 or Dennis et al. (Dennis et al. (2002) J. Biol. Chem. 277, 35035-35043).

In other embodiments, the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. Yet, the skilled person is aware that an amino acid polymer also may form random coil conformation when residues other than alanine, serine, and proline are added as a minor constituent in the PAS sequence.

Non-limiting examples of the PAS sequences forming random coil conformation comprise an amino acid sequence selected from the group consisting of ASPAAPA-PASPAAPAPSAPA (SEQ ID NO:17), AAPASPAPAAP-SAPAPAAPS (SEQ ID NO:18), APSSPSP-SAPSSPSPASPSS (SEQ ID NO:19), APSSPSPSAPSSPSPASPS (SEQ ID NO:20), SSP-SAPSPSSPASPSPSSPA (SEQ ID NO:21), AASPAAPSAP-PAAASPAAPSAPPA (SEQ ID NO:22) and ASAAAPAAASAAASAPSAAA (SEQ ID NO:23) or any combinations thereof. Additional examples of PAS sequences are known from, e.g., US Pat. Publ. No. 2010/0292130 A1 and PCT Appl. Publ. No. WO 2008/155134 A1, which are herein incorporated by reference in their entirety.

In yet other embodiments, the heterologous moiety is a glycine-rich homo-amino-acid polymer (HAP). The HAP sequence can comprise a repetitive sequence of glycine, which has at least 50 amino acids in length. In one embodiment, the HAP sequence is capable of extending half-life of a moiety fused to or linked to the HAP sequence. Non-limiting examples of the HAP sequence includes, but are not limited to $(Gly)_n$, $(Gly_4Ser)_n$ or $S(Gly_4Ser)_n$, wherein n is 1 to 20, 20 to 40, or 40 to 200. See, e.g., Schlapschy M et al., Protein Eng. Design Selection, 20: 273-284 (2007).

In certain embodiments, the heterologous moiety is transferrin or a fragment thereof. Any transferrin may be used to make the chimeric proteins used in accordance with the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and 595936 (ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin portion of the chimeric protein includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, C2 domain or any combinations thereof.

In other embodiments, the heterologous moiety is a soluble polymer known in the art, including, but not limited to, polyethylene glycol, ethylene glycol/propylene glycol copolymers, carboxymethylcellulose, dextran, or polyvinyl alcohol.

The polymer can be of any molecular weight, and can be branched or unbranched. For polyethylene glycol, in one embodiment, the molecular weight is between about 1 kDa and about 100 kDa for ease in handling and manufacturing. Other sizes may be used, depending on the desired profile (e.g., the duration of sustained release desired, the effects, if any on biological activity, the ease in handling, the degree or lack of antigenicity and other known effects of the polyethylene glycol to a protein or analog). For example, the polyethylene glycol may have an average molecular weight of about 200 to about 100,000 kDa.

In some embodiments, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), each of which is incorporated herein by reference in its entirety.

In certain embodiments, the heterologous moiety is a hydroxyethyl starch (HES) or a derivative thereof. HES is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., *Krankenhauspharmazie,* 8(8), 271-278 (1987); and Weidler et al., *Arzneim.-Forschung/Drug Res.,* 41, 494-498 (1991)).

HES is mainly characterized by the molecular weight distribution and the degree of substitution. The degree of substitution, denoted as DS, relates to the molar substitution, is known to the skilled people. See Sommermeyer et al., *Krankenhauspharmazie,* 8(8), 271-278 (1987), as cited above, in particular p. 273. In one embodiment, HES has a mean molecular weight (weight mean) of from 1 to 300 kD, from 2 to 200 kD, from 3 to 100 kD, or from 4 to 70 kD. HES can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. In certain embodiments, the heterologous moiety can be mixtures of hydroxyethyl starches having different mean molecular weights and/or different degrees of substitution and/or different ratios of C2:C6 substitution.

In still other embodiments, the non-polypeptide heterologous moiety is a polymer, e.g., polysialic acids (PSAs) or a derivative thereof. Polysialic acids (PSAs) are naturally occurring unbranched polymers of sialic acid produced by certain bacterial strains and in mammals in certain cells. Roth J., et al. (1993) in Polysialic Acid: From Microbes to Man, eds. Roth J., Rutishauser U., Troy F. A. (Birkhäuser Verlag, Basel, Switzerland), pp 335-348. They can be produced in various degrees of polymerization from n=about 80 or more sialic acid residues down to n=2 by limited acid hydrolysis or by digestion with neuraminidases, or by fractionation of the natural, bacterially derived forms of the polymer. Various methods of attaching or conjugating polysialic acids to a polypeptide have been described (for example, see U.S. Pat. No. 5,846,951; WO-A-0187922, and US 2007/0191597 A1, which are incorporated herein by reference in their entireties.

More detailed description and sequences of the heterologous moieties that can be used in this invention is disclosed, for example, in WO 2013/123457 A1 and WO 2013/106787 A1, which are incorporated herein by reference in their entirety.

In certain embodiments, the polypeptide of interest is a monomer-dimer hybrid comprising a clotting factor. In one embodiment, the monomer-dimer hybrid is a chimeric protein comprising a first polypeptide chain and a second polypeptide chain, which are associated with each other by a disulfide bond, wherein the first chain comprises a clotting factor, e.g., Factor VIII, and an Fc region and the second chain comprises, consists essentially of, or consists of an Fc region without the clotting factor. Various examples of monomer-dimer hybrids comprising one or more clotting factors are described in U.S. Pat. No. 8,329,182, which is incorporated herein by reference in its entirety.

Antibodies

In some embodiments, the polypeptide of interest comprises an antibody or an antibody fragment. Antibodies are proteins that have the ability to specifically bind a particular antigen. Any antibody that can be expressed in a host cell can be used in accordance with the present invention. In one embodiment, the polypeptide of interest is a monoclonal antibody.

Particular antibodies can be made, for example, by preparing and expressing synthetic genes that encode the recited amino acid sequences or by mutating human germline genes to provide a gene that encodes the recited amino acid sequences. Moreover, these antibodies can be produced, e.g., using one or more of the following methods.

Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; and WO 90/02809. The display of Fab's on phage is described, e.g., in U.S. Pat. Nos. 5,658,727; 5,667, 988; and 5,885,793.

In addition to the use of display libraries, other methods can be used to obtain an antibody. For example, a protein or a peptide thereof can be used as an antigen in a non-human animal, e.g., a rodent, e.g., a mouse, hamster, or rat.

Humanized antibodies can be generated by replacing sequences of the Fv variable region that are not directly involved in antigen binding with equivalent sequences from human Fv variable regions. General methods for generating humanized antibodies are provided by Morrison, S. L. (1985) Science 229:1202-1207, by Oi et al. (1986) BioTechniques 4:214, and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, can be obtained from a hybridoma producing an antibody against a predetermined target, as described above, from germline immunoglobulin genes, or from synthetic constructs. The recombinant DNA encoding the humanized antibody can then be cloned into an appropriate expression vector.

The antibodies can be in the form of full length antibodies, or in the form of fragments of antibodies, e.g., Fab, F(ab')2, Fd, dAb, and scFv fragments. Additional forms include a protein that includes a single variable domain, e.g., a camel or camelized domain. See, e.g., U.S. 2005-0079574 and Davies et al. (1996) Protein Eng. 9(6):531-7.

In certain embodiments, the antibody can be an antigen-binding fragment of a full length antibody, e.g., a Fab, F(ab')2, Fv or a single chain Fv fragment. Typically, the antibody is a full length antibody. The antibody can be a monoclonal antibody or a mono-specific antibody.

In another embodiment, the antibody can be a human, humanized, CDR-grafted, chimeric, mutated, affinity matured, deimmunized, synthetic or otherwise in vitro-generated antibody, and combinations thereof.

The heavy and light chains of the antibody can be substantially full-length. The protein can include at least one, or two, complete heavy chains, and at least one, or two, complete light chains, or can include an antigen-binding fragment (e.g., a Fab, F(ab')2, Fv or a single chain Fv fragment). In yet other embodiments, the antibody has a heavy chain constant region chosen from, e.g., IgG1, IgG2, IgG3, IgG4, IgM, IgA1, IgA2, IgD, and IgE; particularly, chosen from, e.g., IgG1, IgG2, IgG3, and IgG4, more particularly, IgG1 (e.g., human IgG1). Typically, the heavy chain constant region is human or a modified form of a human constant region. In another embodiment, the antibody has a light chain constant region chosen from, e.g., kappa or lambda, particularly, kappa (e.g., human kappa).

The methods of the invention can be used to prepare polypeptides comprising antibodies, human antibodies, humanized antibodies, chimeric antibodies, i.e. antibodies having human constant antibody immunoglobulin domains coupled to one or more murine variable antibody immunoglobulin domain, and/or non-human antibodies, or fragments thereof. Specific examples of antibodies suitable for use in the present invention include commercially available antibodies such as muromonab-CD3 (ORTHOCLONE OKT-3®, Ortho Biotech), abciximab (REOPRO®, Lilly), rituximab (RITUXAN®, Biogen IDEC), natalizumab (TYSABRI®, Biogen IDEC), daclizumab (ZENAPAX®, Roche Laboratories), basiliximab (SIMULECT®, Novartis), infliximab (REMICADE®, Centocor), palivizumab (SYNAGIS®, MedImmune), trastuzumab (HERCEPTIN®, Genentech), gemtuzuman ozogamicin (MYLOTARG™, Wyeth-Ayerst), alemtuzumab (CAMPATH®, Berlex), and any combinations thereof.

Examples of antibodies or antibody/cytotoxin or antibody/luminophore conjugates contemplated for use in the invention include those that recognize one or more of the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-4, IL-5, IL-8, IL-10, IL-2 receptor, IL-4 receptor, IL-6 receptor, IL-13 receptor, PDGF-β, VEGF, TGF, TGF-β2, TGF-β1, EGF receptor, VEGF receptor, C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or polypeptides expressed on breast, colon, squamous cell, prostate, pancreatic, lung, and/or kidney cancer cells and/or on melanoma, glioma, or neuroblastoma cells, TRAIL receptors 1, 2, 3 and 4, the necrotic core of a tumor, integrin alpha 4 beta 7, the integrin VLA-4, B2 integrins, TNF-α, the adhesion molecule VAP-1, epithelial cell adhesion molecule (Ep-CAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IFN-γ, Respiratory Syncitial Virus, human immunodeficiency virus (HIV), hepatitis B virus (HBV), *Streptococcus mutans*, and *Staphylococcus aureus*.

The methods of the invention can also be used for anti-idiotypic antibodies, or substantially similar polypeptides, including but not limited to anti-idiotypic antibodies against: an antibody targeted to the tumor antigen gp72; an antibody against the ganglioside GD3; or an antibody against the ganglioside GD2.

Receptors

In some embodiments, the polypeptide of interest comprises a receptor. Receptors are typically trans-membrane glycoproteins that function by recognizing an extra-cellular signaling ligand. Receptors typically have a protein kinase domain in addition to the ligand recognizing domain, which initiates a signaling pathway by phosphorylating target intracellular molecules upon binding the ligand, leading to developmental or metabolic changes within the cell. The receptor can be modified so as to remove the transmembrane and/or intracellular domain(s), in place of which there can optionally be attached an Ig-domain.

One large family of receptors is the receptor tyrosine kinases (RTKs). The RTK family includes receptors that are crucial for a variety of functions numerous cell types (see, e.g., Yarden and Ullrich, *Ann. Rev. Biochem.* 57:433-478, 1988; Ullrich and Schlessinger, *Cell* 61:243-254, 1990, incorporated herein by reference). Non-limiting examples of RTKs include members of the fibroblast growth factor (FGF) receptor family, members of the epidermal growth factor receptor (EGF) family, platelet derived growth factor (PDGF) receptor, tyrosine kinase with immunoglobulin and EGF homology domains-1 (TIE-1) and TIE-2 receptors (Sato et al., *Nature* 376(6535):70-74 (1995), incorporated herein by reference) and c-Met receptor, some of which have been suggested to promote angiogenesis, directly or indirectly (Mustonen and Alitalo, *J. Cell Biol.* 129:895-898, 1995). Other non-limiting examples of RTK's include fetal liver kinase 1 (FLK-1) (sometimes referred to as kinase insert domain-containing receptor (KDR) (Terman et al., *Oncogene* 6:1677-83, 1991) or vascular endothelial cell growth factor receptor 2 (VEGFR-2)), fms-like tyrosine kinase-1 (Flt-1) (DeVries et al. *Science* 255; 989-991, 1992; Shibuya et al., *Oncogene* 5:519-524, 1990), sometimes referred to as vascular endothelial cell growth factor receptor 1 (VEGFR-1), neuropilin-1, endoglin, endosialin, and Ax1.

G-Protein Coupled Receptors

In some embodiments, the polypeptide of interest comprises a G-protein coupled receptor (GPCR). GPCRs are proteins that have seven transmembrane domains. Upon binding of a ligand to a GPCR, a signal is transduced within the cell which results in a change in a biological or physiological property of the cell.

GPCRs, along with G-proteins and effectors (intracellular enzymes and channels which are modulated by G-proteins), are the components of a modular signaling system that connects the state of intracellular second messengers to extracellular inputs. These genes and gene-products are potential causative agents of disease.

The GPCR protein superfamily now contains over 250 types of paralogues, receptors that represent variants generated by gene duplications (or other processes), as opposed to orthologues, the same receptor from different species. The superfamily can be broken down into five families: Family I, receptors typified by rhodopsin and the beta2-adrenergic receptor and currently represented by over 200 unique members; Family II, the recently characterized parathyroid hormone/calcitonin/secretin receptor family; Family III, the metabotropic glutamate receptor family in mammals; Family IV, the cAMP receptor family, important in the chemotaxis and development of *D. discoideum*; and Family V, the fungal mating pheromone receptors such as STE2.

Growth Factors and Other Signaling Molecules

In some embodiments, the polypeptide of interests comprises a growth factor or a signaling molecule. Growth factors are typically glycoproteins that are secreted by cells and bind to and activate receptors on other cells, initiating a metabolic or developmental change in the receptor cell.

CH2/CH3-Containing Polypeptides

Any polypeptide containing a CH2/CH3 domain is suitable for use in accordance with the present invention. In one embodiment, the CH2/CH3-containing polypeptide is a soluble form of the TNF receptor fused to an Fc region (TNFR-Fc). A commercially available TNFR-Fc is known as etanercept (ENBREL®, Immunex Corporation), which is a dimeric fusion polypeptide consisting of the extracellular ligand-binding portion of the human 75 kilodalton (p75) tumor necrosis factor receptor (TNFR) linked to the Fc portion of human IgG1. The Fc component of etanercept contains the constant heavy 2 (CH2) domain, the constant heavy 3 (CH3) domain and hinge region, but not the constant heavy 1 (CH1) domain of human IgG1. It is to be understood that an Fc region can contain one or all of the domains described above. Etanercept is produced by recombinant DNA technology in a Chinese hamster ovary (CHO) mammalian cell expression system. It consists of 934 amino acids and has an apparent molecular weight of approximately 150 kilodaltons (Physicians Desk Reference, 2002, Medical Economics Company Inc.).

Other polypeptides that can be purified in accordance with the invention include recombinant fusion polypeptides comprising at least a portion of an Fc region of an antibody. A polypeptide fused to an Fc domain (e.g., a CH2/CH3 domain) and identical to or substantially similar to one of the following polypeptides is suitable for use in the present disclosed method: a flt3 ligand, a CD40 ligand, erythropoietin, thrombopoeitin, calcitonin, Fas ligand, ligand for receptor activator of NF-kappa B (RANKL), tumor necrosis factor (TNF)-related apoptosis-inducing ligand (TRAIL), thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor (TNF), leukemia inhibitory factor, oncostatin-M, various ligands for cell surface molecules ELK and Hek (such as the ligands for eph-related kinases or LERKS), and any combinations thereof.

Polypeptides suitable for purification according to the invention also include recombinant fusion polypeptides comprising CH2/CH3 domains of an antibody plus a receptor for any of the above-mentioned polypeptides or polypeptides substantially similar to such receptors. These receptors include: both forms of TNFR (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL (TRAIL receptors 1, 2, 3, and 4), and receptors that comprise death domains, such as Fas or Apoptosis-Inducing Receptor (AIR), as well as any combinations thereof.

Other polypeptides suitable for use in the present method include differentiation antigens (referred to as CD polypeptides) or their ligands or polypeptides substantially similar to either of these, which are fused to CH2/CH3 domains of an antibody. Such antigens are disclosed in Leukocyte Typing VI (Proceedings of the VIth International Workshop and Conference, Kishimoto, Kikutani et al., eds., Kobe, Japan, 1996). Similar CD polypeptides are disclosed in subsequent workshops and conferences in the above referenced proceedings series. Examples of such antigens include CD27, CD30, CD39, CD40, and ligands thereto (CD27 ligand, CD30 ligand, etc.). Several of the CD antigens are members of the TNF receptor family, which also includes 41BB ligand and OX40. The ligands are often members of the TNF family, as are 41BB ligand and OX40 ligand. Accordingly, members of the TNF and TNFR families can be purified according to the present invention.

Enzymatically active polypeptides or their ligands can also be purified according to the invention. Examples include recombinant fusion polypeptides comprising CH2/CH3 domains of an antibody fused to all or part of one of the following polypeptides or their ligands or a polypeptide substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, numerous other enzymes and their ligands, and any combinations thereof.

B. Production of Polypeptides of Interest in a Cell Culture Cells

A polypeptide of interest is first expressed and produced in a host cell culture. Host cells include, but are not limited to, prokaryotic cells, eukaryotic cells, plant cells, yeast cells, animal cells, insect cells, avian cells, mammalian cells, and human cells.

Non-limiting examples of prokaryotic cells that can be used in accordance with the present invention include bacterial cells, such as Gram-negative or Gram-positive bacteria, for example, *Escherichia coli*.

Non-limiting examples of mammalian cells that can be used in accordance with the present invention include human embryonic kidney line (293 or 293 cells subcloned for growth in suspension culture, Graham et al., *J. Gen Virol.*, 36:59 (1977)); BALB/c mouse myeloma line (NSW, ECACC No: 85110503); human retinoblasts (PER.C6 (Cru-Cell, Leiden, The Netherlands)); monkey kidney CV1 line transformed by SV40 (COS-7, ATCC CRL 1651); baby hamster kidney cells (BHK, ATCC CCL 10); Chinese hamster ovary cells (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCLS 1); TRI cells (Mather et al., *Annals N.Y. Acad. Sci.*, 383:44-68 (1982)); MRC 5 cells; FS4 cells; and a human hepatoma line (Hep G2).

Additionally, any number of commercially and non-commercially available hybridoma cell lines that express polypeptides or proteins can be utilized in accordance with the present invention.

The host cells can also be selected or engineered to modify its posttranslational modification pathways. For example, the cells can be selected or engineered to modify a protein glycosylation pathway.

Cell Culture Processes for Production of Polypeptide of Interest

Various methods of preparing mammalian cells for production of proteins or polypeptides by batch and fed-batch culture are well known in the art. A nucleic acid sufficient to achieve expression (typically a vector containing the gene encoding the polypeptide or protein of interest and any operably linked genetic control elements) can be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include but are not limited to immunohistochemistry, immunoprecipitation, flow cytometry, immunofluorescence microscopy, SDS-PAGE, Western blots, enzyme-linked immunosorbent assay (ELISA), high performance liquid chromatography (HPLC) techniques, biological activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

C. Purification of Polypeptide of Interest

Procedures for purification of proteins from cell culture initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell as well as from other impurities is usually attempted using a combination of different chromatography techniques. These techniques separate mixtures of proteins on the basis of their charge, degree of hydrophobicity, size, or specific binding affinity.

III. Inactivation of Virus During the Protein Purification Process

One critical concern during the protein purification process is the inactivation or removal of viral contaminations.

When a polypeptide of interest is recombinantly produced in a cell culture, the recombinant DNA encoding the polypeptide must be transfected into the protein-producing cells. Viruses can remain in the culture after transfection and contaminate the protein samples. Additionally, cells used for expressing proteins of interest can encode viral genomes in their DNA or otherwise contain endogenous viruses, which is another potential source of contamination to a therapeutic product derived from cells. A biologically-derived therapeutic, such as a polypeptide produced in a cell culture, must undergo at least two robust virus purification steps in order to meet the safety requirements of regulatory agencies such as the FDA to ensure no active viruses are administered to a patient.

Several methods are known in the art to inactivate viruses. For example, arginine can be used for virus inactivation, such as the method described in U.S. Publication No. 2012/0015424 A1, which is incorporated herein by reference in its entirety. Each method however has its own disadvantages, and may not be suitable or optimal for some protein products.

When low pH is used to inactivate viruses, it has the potential to precipitate proteins, cause aggregation of the product, and/or alter the conformation of certain proteins which can lead to product loss. In addition, during the protein purification process, the low pH virus inactivation step is typically performed after the protein of interest has been eluted from the chromatography column and held in a tank or vessel, especially if the target protein is known to elute from the matrix under low pH conditions, resulting in significant product loss. For example, a CH2/CH3-containing polypeptide such as a monoclonal antibody or FIX-Fc is eluted from the Protein A column at pH values below 4.5.

The present invention provides a novel method of on-column virus inactivation, comprising washing a polypeptide-bound chromatography matrix with a low pH and high salt wash solution that effectively inactivates viruses and maximizes the recovery of the polypeptide. Carrying out the low pH inactivation step on a polypeptide bound to a chromatography matrix improves stability of the polypeptide because the bound polypeptide tends to remain its natural conformation and is unable to aggregate with each other. In addition, the presence of high salt in the wash solution significantly reduces the elution of the polypeptide under low pH conditions.

The present invention provides a method of inactivating virus that is present during production of a polypeptide of interest, comprising: (a) binding the polypeptide to a chromatography matrix, and (b) performing a virus inactivation step by washing the polypeptide-bound chromatography matrix with a wash solution at a pH of lower than about 4.0. The wash solution used in accordance with the present invention comprises a sufficient concentration of salt to substantially reduce the elution of the polypeptide during the virus inactivation step. The substantial reduction of the polypeptide elution is likely due to enhanced hydrophobic interactions between the polypeptide and the matrix.

The methods of the present invention are useful for inactivating a wide range of enveloped viruses. Viruses that can be inactivated by embodiments of the present invention include, without limitation, enveloped viruses classified such as, for example, mammalian or avian Leukemia viruses, Herpes viruses, Pox viruses, Hepadnaviruses, Flaviviruses, Togaviruses, Coronaviruses, Hepatitis viruses, Retroviruses, Orthomyxoviruses, Paramyxoviruses, Rhadoviruses, Bunyaviruses, Filoviruses, Reoviruses, Encephalitis, Sindbis, Vesicular Stomatitis Virus, Human Immunodeficiency Virus (HIV), Rhinotracheitis, Epstein Barr virus, Cytomegalo Virus, Influenza Virus, Sendai Virus, Vaccinia Virus, or any combinations thereof.

In certain embodiments, the polypeptide of interest is selected from the group consisting of: an antibody, a CH2/CH3-containing polypeptide, a clotting factor, a receptor, and any combinations thereof.

In some embodiments, the polypeptide of interest is an antibody or an antibody fragment. In one embodiment, the antibody is a monoclonal antibody. In another embodiment, the antibody is a chimeric antibody, a human antibody, or a humanized antibody.

In some embodiments, the polypeptide of interest comprises a clotting factor. In certain embodiments, the polypeptide of interest is FIX-Fc, FVIII-Fc, or FVII-Fc. In certain embodiments, the polypeptide is a monomer-dimer hybrid. In certain embodiments, the polypeptide further comprises a heterologous moiety.

Many chromatography techniques known in the art can be used in the present invention. In some embodiments, the chromatography matrix is an affinity chromatography matrix. In one embodiment, the affinity chromatography matrix is a Protein A column. In yet another embodiment, the Protein A column is selected from the group consisting of MABSELECT™, MABSELECT™ SuRe, MABSELECT™ SuRe LX, ESHMUNO® A, AMSPHERE™ JWT203, TOYOPEARL® AF-rProtein A-650F, PROSEP®-vA Ultra, PROSEP® Ultra Plus, PROSEP®-vA High Capacity, and any combinations thereof. Non-limiting examples of chromatography matrix that can be used to immobilize the Protein A ligand include dextran based matrix, agarose based matrix, polystyrene based matrix, hydrophilic polyvinyl ethyl based matrix, rigid polymethacrylate based matrix, porous polymer based matrix, controlled pore glass based matrix, and any combinations thereof.

In some embodiments, the chromatography matrix is a mixed-mode chromatography matrix. In one embodiment, the chromatography matrix is a mixed-mode anion exchange chromatography matrix. In one embodiment, the mixed-mode chromatography matrix is selected from the group consisting of CAPTO™ Adhere, CAPTO™ MMC, ESHMUNO® HCX, CAPTO™ MMC ImpRes, CAPTO™ Blue, NUVIA™ cPrime, BLUE SEPHAROSE® Fast Flow, CAPTO™ Adhere ImpRes, CHT™ Ceramic Hydroxyapatite, CFT™ Ceramic Fluoroapatite, and any combinations thereof. Non-limiting examples of mixed mode chromatography matrix include dextran based matrix, agarose based matrix, polystyrene based matrix, polyvinyl ethyl hydrophilic polymer based matrix, macroporous highly cross-linked polymer based matrix, hydroxyapatite $((Ca_5(PO_4)_3OH)_2)$ based matrix, fluoroapatite $((Ca_5(PO_4)_3F)_2)$ based matrix, and any combinations thereof.

In some embodiments, the polypeptide of interest is first harvested after recombinantly produced in cell culture. In certain embodiments, the polypeptide is loaded to the chromatography matrix at a pH from about 6.0 to about 8.0. In some embodiments, the pH of the loading buffer is about 6.0 to about 7.0 or about 7.0 to about 8.0. In one embodiment, the pH of the loading buffer is about 6.0, about 6.5, about 7.0, about 7.5, or about 8.0.

One or more wash steps can be carried out before the polypeptide is eluted from the chromatography matrix. Same or different wash solutions can be used in these wash steps.

In certain embodiments, the pH of the wash solution is about 2.5 to about 3.0, about 3.0 to about 3.5, or about 3.5 to about 4.0. In certain embodiments, the pH of the wash solution is about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0. In one embodiment, the pH of the wash solution is 3.0. In another embodiment, the pH of the wash solution is 3.5.

Non-limiting examples of salts that can be added into the solution or to any buffer used in accordance with the present invention include sodium salts, potassium salts, calcium salts, magnesium salts, barium salts, zinc salts, aluminum salts, ammonium salts, chloride salts, fluoride salts, bromide salts, iodide salts, carbonate salts, nitrate salts, phosphate salts, sulfate salts, acetate salts, and combination thereof. In one embodiment, the salt is sodium chloride (NaCl). In another embodiment, the salt is ammonium sulfate.

In certain embodiments, the concentration of the salt in the wash solution is greater than about 0.5 M. In some embodiments, the concentration of the salt in the wash solution is about 0.5 M to about 1.0 M, about 1.0 M to about 1.5 M, about 1.5 M to about 2.0 M, about 2.0 M to about 2.5 M, about 2.5 M to about 3.0 M, about 3.0 M to about 3.5 M, or about 3.5 M to about 4 M. In some embodiments, the concentration of the salt in the wash solution is about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, about 2.0 M, about 2.1 M, about 2.2 M, about 2.3 M, about 2.4 M, about 2.5 M, about 2.6 M, about 2.7 M, about 2.8 M, about 2.9 M, about 3.0 M, about 3.1 M, about 3.2 M, about 3.3. M, about 3.4 M, about 3.5 M, about 3.6 M, about 3.7 M, about 3.8 M, about 3.9 M, or about 4.0 M. In a specific embodiment, the salt concentration is about 2 M. In another specific embodiment, the salt concentration is about 3 M.

The wash solution can further comprise one or more other components such as a polymer, an organic solvent, a detergent, arginine, or an arginine derivative.

In certain embodiments, the polymer is a polyethylene glycol (PEG), a polypropylene glycol, or a mixture thereof. In one embodiment, the polymer is PEG. In a specific embodiment, the polymer is PEG 3350. In some embodiments, the concentration of the polymer is from about 0.1% to about 20%. In some embodiments, the concentration of the polymer is from about 0.1% to about 15%, from 0.1% to about 10%, from about 0.1% to about 5%, from about 0.1% to about 2%, from about 1% to about 20%, from about 1% to about 15%, from about 1% to about 10%, from about 1% to about 5%, from about 1% to about 2%, from about 5% to about 20%, from about 5% to about 15%, from about 5% to about 10%, from about 10% to about 20%, from about 10% to about 15%, or from about 15% to about 20%. In some embodiments, the concentration of the polymer is about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In certain embodiments, the organic solvent is ethanol, methanol, isopropanol, acetone, ethylene glycol, propylene glycol, hexaethylene glycol, or a mixture thereof. In some embodiments, the concentration of the organic solvent is from about 0.1% to about 20%. In some embodiments, the concentration of the organic solvent is from about 0.1% to about 15%, from 0.1% to about 10%, from about 0.1% to about 5%, from about 0.1% to about 2%, from about 1% to about 20%, from about 1% to about 15%, from about 1% to about 10%, from about 1% to about 5%, from about 1% to about 2%, from about 5% to about 20%, from about 5% to about 15%, from about 5% to about 10%, from about 10% to about 20%, from about 10% to about 15%, or from about 15% to about 20%. In some embodiments, the concentration of the organic solvent is about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In certain embodiments, the detergent is selected from the group consisting of octylphenol ethylene oxide condensate (e.g., TRITON™ X-100); 3-[(3-cholamidopropyl)dimethyl-ammonio]-1-propanesulfonate (CHAPS); 3-[(3-cholamidopropyl)dimethylammonio]-2-hydroxy-1-propane-sulfonate (CHAPSO); lauryldimethyl amine oxide (LDAO); polysorbates (e.g., polysorbates 20 or 80); poloxamers (e.g., poloxamer 188); sodium dodecyl sulfate (SDS); sodium laurel sulfate; sodium octyl glycoside; lauryl-, myristyl-, linoleyl- or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; 1-ethyl-1-(2-hydroxyethyl)-2-isoheptadecylimidazolinium ethylsulfate (e.g., the MONAQUAT™ series); and any combinations thereof. Other examples of commercial products comprising compounds similar to TRITON™ X-100 include, but not limited to, CONCO™ NI, DOWFAX™ 9N, IGEPAL™ CO, MAKON™, NEUTRONYX® 600's, NONIPOL™ NO, POLYTERGENT® B, RENEX™ 600's, SOLAR™ NO, STEROX™, SERFONIC™ N, T-DET-N™, TERGITOL™ NP, and TRITON™ N.

In some embodiments, the concentration of the detergent is from about 0.01% to about 8%. In some embodiments, the concentration of the detergent is from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.5%, from about 0.01% to about 0.1%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.1% to about 0.5%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 8%, from about 1% to about 7%, from about 1% to about 6%, from about 1% to about 5%, from about 1% to about 4%, from about 1% to about 3%, or from about 1% to about 2%. In some embodiments, the concentration of the detergent is about 0.01%, about 0.05%, about 0.1%, about 0.5%, about 1%, about 2%, about 3%, about 4%, about 5%, about 6%, about 7%, or about 8%.

In certain embodiments, more than one on-column virus-inactivation step is carried out during the purification of the polypeptide. In one embodiment, identical wash solutions are used in multiple virus-inactivation steps. In another embodiment, different wash solutions are used in multiple virus-inactivation steps.

In some embodiments, at least one of the wash solutions comprises arginine, an arginine derivative, or a mixture thereof. In some embodiments, the concentration of arginine is from about 0.1 M to about 1 M. In some embodiment, the concentration of arginine is about 0.1 M to about 0.5 M or about 0.5 M to about 1 M. In some embodiments, the concentration of arginine is about 0.1 M, about 0.2 M, about 0.3 M, about 0.4 M, about 0.5 M, about 0.6 M, about 0.7 M, about 0.8 M, about 0.9 M, or about 1 M.

In some embodiments, at least one of the wash solutions comprises detergent. In one embodiment, the detergent is lauryldimethyl amine oxide (LDAO). In another embodiment, the detergent is octylphenol ethylene oxide condensate (e.g., TRITON™ X-100). In other embodiments, the detergent comprises a compound very similar to TRITON™ X-100 (e.g., CONCO™ NI, DOWFAX™ 9N, IGEPAL™ CO, MAKON™, NEUTRONYX® 600's, NONIPOL™ NO, POLYTERGENT® B, RENEX™ 600's, SOLAR™ NO, STEROX™, SERFONIC™ N, T-DET-N™, TERGITOL™ NP, and TRITON™ N).

In certain embodiments, elution of the polypeptide during the low pH wash step for virus inactivation is reduced to less than 30%. In certain embodiments, elution of the polypeptide during the low pH wash step is reduced to less than 25%, less than 20%, less than 15%, less than 10%, or less than 5%.

After the wash steps, the polypeptide of interest is eluted from the chromatography matrix with an elution solution. In certain embodiments, the pH of the elution solution is less than 4.5. In one embodiment, the pH of the elution solution is about 3.0. In another embodiment, the pH of the elution solution is about 3.4.

In certain embodiments, at least about 70% of the polypeptide is recovered in the elution solution. In some embodiments, at least about 75%, at least about 80%, at least about 85%, at least about 90%, or at least about 95% of the polypeptide is recovered in the elution solution.

Additional virus inactivation steps can be performed either prior to, or after, the on-column virus inactivation method disclosed herein.

The eluted polypeptide of interest can be subjected to additional purification steps either prior to, or after, the purification method disclosed herein. Standard methods include but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). Protease inhibitors such as phenyl methyl sulfonyl fluoride (PMSF), leupeptin, pepstatin or aprotinin can be added at any or all stages in order to reduce or eliminate degradation of the polypeptide or protein during the purification process. Protease inhibitors are particularly desired when cells must be lysed in order to isolate and purify the expressed polypeptide or protein. One of ordinary skill in the art will appreciate that the exact purification technique will vary depending on the character of the polypeptide or protein to be purified, the character of the cells from which the polypeptide or protein is expressed, and the composition of the medium in which the cells were grown.

The virus inactivation method of present invention can be used to help enable processes that utilize multiple affinity chromatography columns like simulated moving bed or tandem chromatography which generate multiple elution pools. Instead of combining the elution pools to carry out low pH viral inactivation which can result in a long holds at low pH values and a greater product loss, or going through the tedious and time-consuming process of carrying out low pH viral inactivation in the individual pools, the present invention carries out low pH viral inactivation during the individual tandem or simulated moving bed chromatography runs, thus obviating the need for viral inactivation of the elution pools.

The foregoing description is to be understood as being representative only and is not intended to be limiting. Alternative methods and materials for implementing the invention and also additional applications will be apparent to one of skill in the art, and are intended to be included within the accompanying claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), *DNA Cloning*, D. N. Glover ed., Volumes I and II (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Maryland (1989).

All of the references cited above, as well as all references cited herein, are incorporated herein by reference in their entirety.

The following examples are offered by way of illustration and not by way of limitation.

EXAMPLES

Example 1

On-Column Viral Inactivation Using a Wash Solution Containing 2 M Ammonium Sulfate at pH 3.5

The objective of the experiments shown in Examples 1 to 10 is to demonstrate the feasibility and applicability of an on-column low-pH viral inactivation step using ProA and a target polypeptide. The polypeptide was bound to the ProA under standard conditions before a high salt at neutral pH was applied to the column. A subsequent wash at high salt and low pH was then applied to inactivate virus while the polypeptide remained bound to the adsorbent. A series of washes were performed before the polypeptide was recovered using an elution solution.

The goal of the first experiment was to determine if on-column viral inactivation could be performed with minimal recovery loss using 2 M ammonium sulfate wash at pH 3.5.

In this experiment, a 0.66 cm diameter MABSELECT™ SuRe column (7.2 mL; 21 cm) was first equilibrated (EQ) with 4 column volumes (CVs) of 10 mM sodium phosphate (NaPhosphate), 140 mM NaCl, pH 7.4. 256 ml of filtered (at 0.22 μm) harvested cell culture fluid (HCCF) containing recombinantly produced FIX-Fc was then loaded onto the column (25.5 mg rFIXFc per mL of resin).

The loading was followed by seven wash steps as indicated in Table 1 below. The target polypeptide was subsequently eluted with 25 mM citrate, 150 mM NaCl, pH 3.4. The flow rate of the chromatography was consistent at 300 cm/hr or 1.7 ml/min except that a lower rate (100 cm/hr) was used during the low pH wash step (wash 4).

TABLE 1

Individual buffers used in Example 1.

| Step | Buffer Components | pH | Vol. |
|---|---|---|---|
| EQ | 10 mM NaPhosphate, 140 mM NaCl | 7.4 | 4 CVs |
| Load | Filtered HCCF | | 256 ml |
| Wash 1 | 10 mM NaPhosphate, 140 mM NaCl | 7.4 | 4.5 CVs |
| Wash 2 | 10 mM NaPhosphate, 900 mM NaCl | 7.4 | 4 CVs |
| Wash 3 | 100 mM Bis-Tris, 2M Ammonium Sulfate | 7.0 | 4 CVs |
| Wash 4 | 100 mM Bis-Tris, 2M Ammonium Sulfate | 3.5 | 5 CVs |
| Wash 5 | 100 mM Bis-Tris, 2M Ammonium Sulfate | 7.0 | 4 CVs |
| Wash 6 | 10 mM NaPhosphate, 900 mM NaCl | 7.4 | 4 CVs |
| Wash 7 | 10 mM NaPhosphate, 140 mM NaCl | 7.4 | 3 CVs |
| Elution | 25 mM Citrate, 150 mM NaCl | 3.4 | 3 CVs |
| Strip | 10 mM NaPhosphate, 900 mM NaCl | 7.4 | 5 CVs |
| Regeneration | 0.1N NaOH | | 3 CVs |
| HETP* | 10 mM NaPhosphate, 140 mM NaCl | 7.4 | 4 CVs |
| Storage | 500 mM Acetic Acid, 1% Benzyl Alcohol | 3.2 | 5 CVs |

*HETP stands for Height of an Equivalent Transfer Plate, which is a solution used to measure column integrity.

FIG. 1 is a chromatogram showing the protein concentration and the pH in each fraction during the chromatography steps. The polypeptide recovery was 84% in the eluate, which is surprising given the low pH of wash 4 (pH=3.5) because such low pH wash would usually lead to polypeptide dissociation from the column and cause substantial product loss. The viral removal as measured by PCR was 4.96 $\log_{10}$. The combined removal and inactivation provided by the column washes was higher at >6.39 $\log_{10}$, indicating the low pH can provide effective inactivation of viruses.

Samples were assayed for infectious virus by plaque assay and for viral nucleic acids by Q-PCR assay. The column loading was 25.5 mg rFIXFc per mL of resin. Tables 2 and 3 summarize the results of X-MLV viral clearance as measured by infectivity and qPCR, respectively.

The load was spiked with 8.79 $\log_{10}$ X-MLV (PFU) and >6.39 $\log_{10}$ retroviral inactivation was calculated. When measured by qPCR, the load was spiked with 8.77 $\log_{10}$ X-MLV (GC) and a reduction factor of 4.96 $\log_{10}$ was calculated. These results show a robust retroviral removal by the MABSELECT™ SuRe column at high loadings and additional low pH/high salt buffer. The infectivity results show total retroviral inactivation after the MABSELECT™ SuRe resin is exposed to one hour of low pH/high salt buffer.

TABLE 2

X-MLV Clearance Data by MABSELECT™ SuRe Step by Infectivity

| Sample Description | Viral Titer (PFU/mL) | Volume Adjust (mL) | Adjusted Viral Titer (PFU) | $\log_{10}$ Adjusted Titer (PFU) | $\log_{10}$ Reduction |
|---|---|---|---|---|---|
| Stock Virus Control | 4.67E+7 | 263.0 | 6.14E+8 | 8.79 | 0.00 |
| Load | 2.33E+6 | 263.0 | 6.14E+8 | 8.79 | 0.00 |
| Eluate Run 6 | <5.99E+0 | 41.8 | <2.50E+2 | <2.40 | >6.39 |

PFU = Plaque Forming Units

TABLE 3

X-MLV Clearance Data by MABSELECT™ SuRe Step by qPCR

| Sample Description | Viral Titer by qPCR (GC) | Volume Adjust (mL) | Adjusted Viral Titer (GC) | $\log_{10}$ Adjusted Titer (GC) | $\log_{10}$ Reduction |
|---|---|---|---|---|---|
| Stock Virus Control | 4.53E+7 | 263.0 | 5.96E+8 | 8.77 | 0.00 |
| Load | 2.26E+6 | 263.0 | 5.94E+8 | 8.77 | 0.00 |
| Eluate Run 6 | 1.53E+2 | 41.8 | 6.39E+3 | 3.81 | 4.96 |

GC = Genome Copies

Therefore, the above results demonstrate that a low pH and high salt wash solution can effectively inactivate viruses during a Protein A chromatography purification process without removing the majority of the target polypeptide from the column.

Example 2

On-Column Viral Inactivation Using a Wash Solution Containing 1 M Arginine HCl at pH 4.7

The goal of this experiment was to compare the effects of on-column viral inactivation using a wash solution containing 1 M arginine HCl at pH 4.7.

In this experiment, the Protein A column and the target polypeptide were the same as those in Example 1. A 7.0 mL (20.5 cm) MabSelect SuRe column was first equilibrated, and then 157 ml of HCCF containing Fc-fusion protein was loaded onto the column. Table 4 below summarizes the buffer solutions used in each step. The target polypeptide was bound to the Pro A under standard conditions. A subsequent modified wash 3 containing arginine was then applied to inactivate virus while the polypeptide remained bound to the adsorbent. The flow rate of the chromatography was consistent at 300 cm/hr or 1.7 ml/min except that a lower rate (100 cm/hr or 0.56 ml/min) was used during the arginine wash step (wash 3).

TABLE 4

Individual buffers used in Example 2.

| Step | Buffer Components | pH | Vol. |
|---|---|---|---|
| EQ | 10 mM NaPhosphate, 140 mM NaCl | 7.4 | 4 CVs |
| Load | Filtered HCCF | | 157 ml |
| Wash 1 | 10 mM NaPhosphate, 140 mM NaCl | 7.4 | 4.5 CVs |
| Wash 2 | 10 mM NaPhosphate, 900 mM NaCl | 7.4 | 4 CVs |
| Wash 3 | 1M Arginine HCl | 4.7 | 5 CVs |
| Wash 4 | 10 mM NaPhosphate, 140 mM NaCl | 7.4 | 3 CVs |
| Elution | 25 mM Citrate, 150 mM NaCl | 3.4 | 3 CVs |
| Strip | 10 mM NaPhosphate, 900 mM NaCl | 7.4 | 5 CVs |
| Regeneration | 0.1N NaOH | | 3 CVs |
| HETP | 10 mM NaPhosphate, 140 mM NaCl | 7.4 | 4 CVs |
| Storage | 500 mM Acetic Acid, 1% Benzyl Alcohol | 3.2 | 5 CVs |

FIG. 2 is a chromatogram showing the protein concentration and the pH in each fraction during the chromatography steps. The polypeptide recovery was 83% in the eluate, which is comparable to the recovery percentage using a pH 3.5 and 2 M ammonium sulfate wash solution as shown in Example 1. The viral removal as measured by PCR was >5.54 $\log_{10}$, and the combined removal and inactivation provided by the column washes was higher at >6.39 $\log_{10}$. Both numbers are very similar to those in Example 1.

These results indicate that wash solutions containing either 1 M arginine at pH 4.7 or pH 3.5 with 2 M ammonium sulfate can provide similar level of viral inactivation and protein recovery.

Example 3

On-Column Viral Inactivation Using a Wash Solution Containing 4×CMC Lauryldimethyl Amine Oxide (LDAO)

The goal of this experiment was to compare the effects of on-column viral inactivation using a wash solution containing 4× critical micelle concentration (CMC) lauryldimethyl amine oxide (LDAO).

In this experiment, the Protein A column and the target polypeptide were still the same as those in Example 1. A 7.0 mL (20.5) MABSELECT™ SuRe column was equilibrated and then loaded with 256 ml of HCCF containing Fc-fusion protein. Table 5 below summarizes the buffer solutions used in each step. The target polypeptide was bound to the Pro A under standard conditions. A subsequent modified wash 4 containing 4× CMC LDAO was then applied to inactivate virus while the polypeptide remained bound to the adsorbent. The flow rate of the chromatography was consistent at 300 cm/hr or 1.7 ml/min except that a lower rate (100 cm/hr or 0.56 ml/min) was used during the detergent wash step (wash 4).

TABLE 5

Individual buffers used in Example 3.

| Step | Buffer Components | pH | Vol. |
|---|---|---|---|
| EQ | 10 mM NaPhosphate, 140 mM NaCl | 7.4 | 4 CVs |
| Load | Filtered HCCF | | 256 ml |
| Wash 1 | 10 mM NaPhosphate, 140 mM NaCl | 7.4 | 4.5 CVs |
| Wash 2 | 10 mM NaPhosphate, 900 mM NaCl | 7.4 | 4 CVs |
| Wash 3 | 10 mM NaPhosphate, 140 mM NaCl | | 3 CVs |
| Wash 4 | 10 mM NaPhosphate, 140 mM NaCl, 4x CMC LDAO | 7.4 | 5 CVs |
| Wash 5 | 10 mM NaPhosphate, 140 mM NaCl | 7.4 | 3 CVs |
| Elution | 25 mM Citrate, 150 mM NaCl | 3.4 | 3 CVs |
| Strip | 10 mM NaPhosphate, 900 mM NaCl | 7.4 | 5 CVs |
| Regeneration | 0.1N NaOH | | 3 CVs |

TABLE 5-continued

Individual buffers used in Example 3.

| Step | Buffer Components | pH | Vol. |
|---|---|---|---|
| HETP | 10 mM NaPhosphate, 140 mM NaCl | 7.4 | 4 CVs |
| Storage | 500 mM Acetic Acid, 1% Benzyl Alcohol | 3.2 | 5 CVs |

FIG. 3 is a chromatogram showing the protein concentration and the pH in each fraction during the chromatography steps. The polypeptide recovery was 85% in the eluate, which is comparable to the recovery percentage using a pH 3.5 and 2 M ammonium sulfate wash solution. The viral removal as measured by PCR was 5.11 $\log_{10}$, and the combined removal and inactivation provided by the column washes was higher at >6.40 $\log_{10}$. Both numbers are similar to those in Example 1.

These results indicate that wash solutions containing either 4×CMC LDAO or pH 3.5 with 2 M ammonium sulfate can provide similar level of viral inactivation.

Example 4

On-Column Viral Inactivation Using a Wash Solution Containing 20% PEG and 2 M NaCl at pH 3.0

Various low pH wash solutions were used in Examples 4 to 10 to further explore the feasibility and applicability of an on-column viral inactivation step. Protein A chromatography and a monoclonal antibody were used in the following experiments. The monoclonal antibody was bound to the ProA under standard conditions before a high salt at neutral pH was applied to the column. A subsequent wash at high salt and low pH (about pH 3.0) was then applied to inactivate virus while the antibody remained bound to the adsorbent. A series of washes were performed before the antibody was recovered using an elution solution.

The goal of this experiment was to determine if on-column viral inactivation could be performed with minimal recovery loss using a pH 3.0, 2 M NaCl, 100 mM glycine wash with 20% PEG.

In this experiment, a 0.6 cm diameter MABSELECT™ SuRe column was first equilibrated (EQ) with 5 column volumes (CVs) of 75 mM sodium phosphate, 100 mM NaCl, pH 7.3. 50 ml of filtered (at 0.22 μm) HCCF containing the polypeptide of interest was then loaded onto the column to ≤35 g/$L_{resin}$. The column was chased with 3 CVs of equilibration buffer.

The loading was followed by 5 CVs wash with 100 mM Bis-Tris, 2 M NaCl, pH 7.0 (wash 1), followed by 5 CVs of low pH wash with 100 mM Glycine, 20% PEG 3350, 2M NaCl, pH 3.0 (wash 2). The column was then washed with 5 CVs of 100 mM Bis-Tris, 2 M NaCl, pH 7.0 (wash 3), followed by 5 CVs wash with 100 mM Bis-Tris, pH 7.0 (wash 4). The target polypeptide was subsequently eluted with 100 mM glycine, pH 3.0 (elution).

FIG. 4 is a chromatogram showing the protein concentration and the pH in each fraction during the chromatography steps. Table 6 below summarizes the condition used in each step. The flow rate of the chromatography was consistent at 250 cm/hr or 1.42 ml/min except that a lower rate (50 cm/hr) was used during the regeneration step. Table 7 summarizes the percentage recovery calculated for each chromatography step.

TABLE 6

Individual buffers used in Example 4.

| Step | Buffer Components | pH | Vol. | Fraction |
|---|---|---|---|---|
| EQ | 75 mM NaPhosphate, 100 mM NaCl | 7.3 | 5 CVs | |
| Load | Filtered HCCF | | 50 ml | F2 |
| Chase | 75 mM NaPhosphate, 100 mM NaCl | 7.3 | 3 CVs | F2 |
| Wash 1 | 100 mM Bis-Tris, 2M NaCl | 7.0 | 5 CVs | F3 |
| Wash 2 | 100 mM Glycine, 20% PEG 3350, 2M NaCl | 3.0 | 5 CVs | F4 |
| Wash 3 | 100 mM Bis-Tris, 2M NaCl | 7.0 | 5 CVs | F5 |
| Wash 4 | 100 mM Bis-Tris | 7.0 | 5 CVs | F6 |
| Elution | 100 mM Glycine | 3.0 | 3.5 CVs | F7 |
| Regeneration | 0.3N NaOH | | 5 CVs | F8 |
| Flush | 75 mM NaPhosphate, 100 mM NaCl | 7.3 | 2 CVs | Waste |
| Storage | 500 mM NaAcetate, 1% Benzyl Alcohol | 3.2 | 4 CVs | Waste |

TABLE 7

Percentage Recovery in Each Chromatography Step Using A Wash Solution Containing 20% PEG and 2M NaCl at pH 3.0

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.2704 | 8.96 | 5.5 |
| F4 Wash 2 | 33.15 | 0.9514 | 31.54 | 19.5 |
| F5 Wash 3 | 33.15 | 0.0125 | 0.41 | 0.3 |
| F6 Wash 4 + pre | 41.44 | 0.0081 | 0.00 | |
| F7 Elution | 23.205 | 5.1370 | 119.20 | 73.8 |
| F8 Regen | 33.15 | 0.0435 | 1.44 | 0.9 |
| Total Mass Recovered (mgs) | | | 161.6 | |
| Recoverable Titer Elution Mass/Load Volume | | | 3.23 | |
| Column Loading (mg/ml resin) | | | 24.5 | |

As shown in FIG. 4 and Table 7, only minor product loss (19.5% of the target polypeptide) was observed during the low pH wash (F4, wash 2) with 20% PEG and 2 M NaCl at pH 3.0. The majority of the product (73.8% of the target polypeptide) was recovered in the elution buffer (F7).

Example 5

On-Column Viral Inactivation Using a Wash Solution Containing 2% Ethanol and 2 M NaCl at pH 3.0

The goal of this experiment was to determine if on-column viral inactivation could be performed with minimal recovery loss using a pH 3.0, 2 M NaCl, 100 mM glycine wash with 2% ethanol.

In this experiment, the Protein A column and the target polypeptide were the same as those in Example 4. All the buffer solutions used in each step were also the same as those listed in Table 6, except that the low pH wash (wash 2) buffer solution was 100 mM glycine, 2% ethanol, 2 M NaCl, pH 3.0. All the flow rates were the same as in Example 4.

FIG. 5 is a chromatogram showing the protein concentration and the pH in each fraction during the chromatography steps. Table 8 summarizes the percentage recovery calculated for each chromatography step.

TABLE 8

Percentage Recovery in Each Chromatography Step Using A Wash Solution Containing 2% Ethanol and 2M NaCl at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.4013 | 13.30 | 7.6 |
| F4 Wash 2 | 33.15 | 0.9584 | 31.77 | 18.2 |
| F5 Wash 3 | 33.15 | 0.1419 | 4.71 | 2.7 |
| F6 Wash 4 + pre | 41.44 | 0.0111 | 0.00 | |
| F7 Elution | 23.205 | 5.3128 | 123.28 | 70.7 |
| F8 Regen | 33.15 | 0.0420 | 1.39 | 0.8 |
| Total Mass Recovered (mgs) | | | 174.5 | |
| Recoverable Titer Elution Mass/Load Volume | | | 3.49 | |
| Column Loading (mg/ml resin) | | | 26.4 | |

As shown in FIG. 5 and Table 8, only minor product loss (18.2% of the target polypeptide) was observed during the low pH wash (F4, wash 2) with 20% PEG and 2 M NaCl at pH 3.0. The majority of the product (70.7% of the target polypeptide) was recovered in the elution buffer (F7).

Example 6

On-Column Viral Inactivation Using a Wash Solution Containing 2% Ethanol and 2 M Ammonium Sulfate at pH 3.0

The goal of this experiment was to determine if on-column viral inactivation could be performed with minimal recovery loss using a pH 3.0, 2 M ammonium sulfate, 100 mM glycine wash with 2% ethanol.

In this experiment, the Protein A column and the target polypeptide were the same as those in Example 4. All the buffer solutions used in each step were also the same as those listed in Table 6, except that the low pH wash (wash 2) buffer solution was 100 mM glycine, 2% ethanol, 2 M ammonium sulfate, pH 3.0, and 2 M ammonium sulfate replaced the 2 M NaCl in wash 1 and wash 3 solutions. All the flow rates were the same as in Example 4.

FIG. 6 is a chromatogram showing the protein concentration and the pH in each fraction during the chromatography steps. Table 9 summarizes the percentage recovery calculated for each chromatography step.

TABLE 9

Percentage Recovery in Each Chromatography Step Using A Wash Solution Containing 2% Ethanol and 2M Ammonium Sulfate at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.1630 | 5.40 | 3.1 |
| F4 Wash 2 | 33.15 | 0.0100 | 0.33 | 0.2 |
| F5 Wash 3 | 33.15 | 0.0016 | 0.05 | 0.0 |
| F6 Wash 4 + pre | 41.44 | 0.0339 | 0.00 | |
| F7 Elution | 23.205 | 6.9053 | 160.24 | 92.3 |
| F8 Regen | 33.15 | 0.2268 | 7.52 | 4.3 |
| Total Mass Recovered (mgs) | | | 173.5 | |
| Recoverable Titer Elution Mass/Load Volume | | | 3.47 | |
| Column Loading (mg/ml resin) | | | 26.3 | |

As shown in FIG. 6 and Table 9, only insignificant product loss (0.2% of the target polypeptide) was observed during the low pH wash (F4, wash 2) with 2% ethanol and 2 M ammonium sulfate at pH 3.0. The majority of the product (92.3% of the target polypeptide) was recovered in the elution buffer (F7).

Example 7

On-Column Viral Inactivation Using a Wash Solution Containing 2% Acetone and 2 M Ammonium Sulfate at pH 3.0

The goal of this experiment was to determine if on-column viral inactivation could be performed with minimal recovery loss using a pH 3.0, 2 M ammonium sulfate, 100 mM glycine wash with 2% acetone.

In this experiment, the Protein A column and the target polypeptide were the same as those in Example 4. All the buffer solutions used in each step were also the same as those listed in Table 6, except that the low pH wash (wash 2) buffer solution was 100 mM glycine, 2% acetone, 2 M ammonium sulfate, pH 3.0, and 2 M ammonium sulfate replaced the 2 M NaCl in wash 1 and wash 3 solutions. All the flow rates were the same as in Example 4.

FIG. 7 is a chromatogram showing the protein concentration and the pH in each fraction during the chromatography steps. Table 10 summarizes the percentage recovery calculated for each chromatography step.

TABLE 10

Percentage Recovery in Each Chromatography Step Using A Wash Solution Containing 2% Acetone and 2M Ammonium Sulfate at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.1495 | 4.96 | 2.8 |
| F4 Wash 2 | 33.15 | 0.0100 | 0.33 | 0.2 |
| F5 Wash 3 | 33.15 | 0.0016 | 0.05 | 0.0 |
| F6 Wash 4 + pre | 41.44 | 0.0339 | 0.00 | |
| F7 Elution | 23.205 | 7.3562 | 170.70 | 96.3 |
| F8 Regen | 33.15 | 0.0389 | 1.29 | 0.7 |
| Total Mass Recovered (mgs) | | | 177.3 | |
| Recoverable Titer Elution Mass/Load Volume | | | 3.55 | |
| Column Loading (mg/ml resin) | | | 26.9 | |

As shown in FIG. 7 and Table 10, only insignificant product loss (0.2% of the target polypeptide) was observed during the low pH wash (F4, wash 2) with 2% acetone and 2 M ammonium sulfate at pH 3.0. The majority of the product (more than 96.3% of the target polypeptide) was recovered in the elution buffer (F7).

Example 8

On-Column Viral Inactivation Using a Wash Solution Containing 2 M Ammonium Sulfate at pH 3.0

The goal of this experiment was to determine if on-column viral inactivation could be performed with minimal recovery loss using a pH 3.0, 2 M ammonium sulfate, 100 mM glycine wash with no other modifiers.

In this experiment, the Protein A column and the target polypeptide were still the same as those in Example 4. A 6.6 mL MABSELECT™ SuRe column (19.4 cm) was first equilibrated and then loaded onto 25.8 g/L resin using 50 mL of antibody in HCCF. A flow rate of 250 cm/hr was used except during the regeneration step (50 cm/hr). All the buffer solutions used in each step were also the same as those listed in Table 6, except that the low pH wash (wash 2) buffer solution was 100 mM glycine, 2 M ammonium sulfate, pH 3.0, and 2 M ammonium sulfate replaced the 2 M NaCl in wash 1 and wash 3 solutions. All the flow rates were the same as in Example 4. The pH 3.0, 2 M ammonium sulfate, 100 mM glycine wash was used to keep the antibody bound to the resin at low pH. The low pH, high ammonium sulfate wash was bracketed by a neutral, high ammonium sulfate wash buffer (pH 7.0, 2 M ammonium sulfate) to ensure that high levels of ammonium sulfate were present as the pH was lowered to 3.0 and also when it was subsequently raised to 7.0. Without this, significant product elution occurred before and after the wash step. Excess wash buffer was used at each step to ensure adequate buffer exchange. FIG. 8 is a chromatogram showing the protein concentration and the pH in each fraction during the chromatography steps. Table 11 summarizes the percentage recovery calculated for each chromatography step.

TABLE 11

Percentage Recovery in Each Chromatography Step Using A Wash Solution Containing 2M Ammonium Sulfate at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.1542 | 5.11 | 3.0 |
| F4 Wash 2 | 33.15 | 0.0954 | 3.16 | 1.9 |
| F5 Wash 3 | 33.15 | 0.0000 | 0.00 | 0.0 |
| F6 Wash 4 + pre | 41.44 | 0.0334 | 0.00 | |
| F7 Elution | 23.205 | 6.9315 | 160.85 | 94.4 |
| F8 Regen | 33.15 | 0.0362 | 1.20 | 0.7 |
| Total Mass Recovered (mgs) | | | 170.3 | |
| Recoverable Titer Elution Mass/Load Volume | | | 3.41 | |
| Column Loading (mg/ml resin) | | | 25.8 | |

As shown in FIG. 8 and Table 11, only very minor product loss (1.9% of the target polypeptide) was observed during the low pH wash (F4, wash 2) with 2 M ammonium sulfate at pH 3.0. The majority of the product (94.4% of the target polypeptide) was recovered in the elution buffer (F7). The percentage of the peak that was monomeric antibody, 96.0%, was not altered by the high ammonium sulfate wash.

The high salt, low pH wash buffer did not increase removal of host cell protein (HCP) on the protein A step. The levels of HCP in the eluate were typically the same or higher than those achieved using a simple neutral pH, sodium chloride wash. It is likely that the high levels of ammonium sulfate in the low pH wash enhanced interactions between HCP and antibodies or HCP and protein A resin. It is also possible that the ammonium sulfate decreased the solubility of the HCP, reducing the clearance.

An additional experiment at conditions similar to the previous one was performed but with sodium chloride substituted for ammonium sulfate. The yield loss was higher using a 2 M NaCl, pH 3.0 wash step (17.0%) compared to the 2 M ammonium sulfate pH 3.0 wash step (1.9%). Since ammonium sulfate is a stronger kosmotrope than sodium chloride, a lower concentration is required to prevent antibody elution. It is believed that using a higher concentration of sodium chloride (3 M) would prevent antibody elution and allow on-column viral inactivation.

Example 9

On-Column Viral Inactivation Using a Wash Solution Containing 2% TRITON™ X-100 and 2 M NaCl at pH 3.0

The goal of this experiment was to determine if on-column viral inactivation could be performed with minimal recovery loss using a pH 3.0, 2 M NaCl, 100 mM glycine wash with 2% TRITON™ X-100.

In this experiment, the Protein A column and the target polypeptide were still the same as those in Example 4. All the buffer solutions used in each step were also the same as those listed in Table 6, except that the low pH wash (wash 2) buffer solution was 100 mM glycine, 2% TRITON™ X-100, 2 M NaCl, pH 3.0. All the flow rates were the same as in Example 4.

FIG. 9 is a chromatogram showing the protein concentration and the pH in each fraction during the chromatography steps. Table 12 summarizes the percentage recovery calculated for each chromatography step.

TABLE 12

Percentage Recovery in Each Chromatography Step Using A Wash Solution Containing 2% TRITON ™ X-100 and 2M NaCl at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.4350 | 14.42 | 10.3 |
| F4 Wash 2 | 33.15 | 0.0954 | 3.16 | 2.3 |
| F5 Wash 3 | 33.15 | 0.0000 | 0.00 | 0.0 |
| F6 Wash 4 + pre | 41.44 | 0.0440 | 0.00 | |
| F7 Elution | 23.205 | 5.2009 | 120.69 | 86.2 |
| F8 Regen | 33.15 | 0.0515 | 1.71 | 1.2 |
| Total Mass Recovered (mgs) | | | 140.0 | |
| Recoverable Titer Elution Mass/Load Volume | | | 2.80 | |
| Column Loading (mg/ml resin) | | | 21.2 | |

As shown in FIG. 9 and Table 12, only very minor product loss (2.3% of the target polypeptide) was observed during the low pH wash (F4, wash 2) with 2% TRITON™ X-100 and 2 M NaCl at pH 3.0. The majority of the product (86.2% of the target polypeptide) was recovered in the elution buffer (F7).

Example 10

On-Column Viral Inactivation Using a Wash Solution Containing 2 M NaCl at pH 3.0

The goal of this experiment was to determine if on-column viral inactivation could be performed with minimal recovery loss using a pH 3.0, 2 M NaCl, 100 mM glycine wash with no other modifiers.

In this experiment, the Protein A column and the target polypeptide were still the same as those in Example 4. All the buffer solutions used in each step were also the same as those listed in Table 6, except that the low pH wash (wash 2) buffer solution was 100 mM glycine, 2 M NaCl, pH 3.0. All the flow rates were the same as in Example 4.

FIG. 10 is a chromatogram showing the protein concentration and the pH in each fraction during the chromatography steps. Table 13 summarizes the percentage recovery calculated for each chromatography step.

TABLE 13

Percentage Recovery in Each Chromatography Step Using A Wash Solution Containing 2M NaCl at pH 3.0.

| Step | Volume (ml) | Conc (mg/ml) | Mass (mgs) | % Recovery (calculated from total mass recovered) |
|---|---|---|---|---|
| Load | 50 | | | |
| F3 Wash 1 | 33.15 | 0.4540 | 15.05 | 8.2 |
| F4 Wash 2 | 33.15 | 0.9881 | 32.75 | 17.9 |
| F5 Wash 3 | 33.15 | 0.1212 | 4.02 | 2.2 |
| F6 Wash 4 + pre | 41.44 | 0.0099 | 0.00 | |
| F7 Elution | 23.205 | 5.6518 | 131.15 | 71.6 |
| F8 Regen | 33.15 | 0.0086 | 0.29 | 0.2 |
| Total Mass Recovered (mgs) | | | 183.3 | |
| Recoverable Titer Elution Mass/Load Volume | | | 3.67 | |
| Column Loading (mg/ml resin) | | | 27.8 | |

As shown in FIG. 10 and Table 13, only minor product loss (17.9% of the target polypeptide) was observed during the low pH wash (F4, wash 2) with 2 M NaCl at pH 3.0. The majority of the product (71.6% of the target polypeptide) was recovered in the elution buffer (F7).

Taken together, the results in Examples 1 to 10 demonstrate that on-column viral inactivation using a low pH and high salt wash solution could be effectively performed with minimal recovery loss.

Example 11

On-Column Viral Inactivation in a Mixed-Mode Anion Exchange Chromatography Column Using a Low pH Wash Solution Containing 2 M Ammonium Sulfate The objective of the following experiment is to demonstrate the potential feasibility and applicability of an on-column viral inactivation step using a low pH and high salt wash solution with other types of chromatography such as a mixed mode anion exchange chromatography.

In this experiment, 6 mL of 0.22 micron filtered product pool containing a monoclonal antibody from an anion exchange purification step at 10 mg/ml mab was loaded onto a 1.7 mL column containing CAPTO™ Adhere resin at pH 8.0. A high salt wash buffer at pH 8.0 was applied to the column (wash 1). A subsequent modified wash (wash 2-4) was then applied to maintain the high salt condition but drop the pH to where is suitable for viral inactivation, while the antibody remained bound to the absorbent.

Table 14 below shows the conditions used in each step. The flow rate of the chromatography was constant at 100 cm/hr.

TABLE 14

Individual buffers used in Example 11.

| Step | Buffer Components | pH | Vol. |
|---|---|---|---|
| EQ | 50 mM Tris | 8.0 | 15 CVs |
| Load | Filtered and concentrated HCCF | | 6 ml |
| Wash 1 | 50 mM Tris, 2M Ammonium Sulfate | 8.0 | 15 CVs |
| Wash 2 | 50 mM Acetate, 2M Ammonium Sulfate | 5.0 | 15 CVs |
| Wash 3 | 50 mM Citrate, 2M Ammonium Sulfate | 4.0 | 15 CVs |
| Wash 4 | 100 mM Citrate, 2M Ammonium Sulfate | 3.5 | 15 CVs |
| Elution | 100 mM Citrate | 3.4 | 15 CVs |
| Regeneration | 1N NaOH | | 15 CVs |
| Storage | 100 mL/L Benzyl Alcohol, 30.3 g/L Acidic Acid, 0.64 g/L NaOH, 965 mL RO/DI | | 10 CVs |

FIG. 11 is a chromatogram showing the protein concentration and the pH in each fraction during the chromatography steps.

The wash solutions used in this experiment resulted in minimal removal of target polypeptide (20.6%) at these low pHs (3.5 and 4.0). The overall recovery was 77.4% in this experiment.

Similar experiment was performed on a standard (not mixed-mode) anion exchange chromatography column using the same low pH and high salt wash solutions. In contrast, the overall recovery of the polypeptide was only 49.8% in this experiment, indicating that a significant amount of the polypeptide was eluted during the low pH wash. This experiment indicates that low pH viral inactivation may not be carried out while product is bound to a standard anion exchange resin by using high salt in the buffer.

Taken together, these results indicate that on-column viral inactivation using a low pH and high salt wash solution could be effectively performed with minimal recovery loss in certain chromatography methods, such as affinity chromatography and mix-mode anion-exchange chromatography.

Example 12

Inactivation of Viruses

Low pH can damage antibodies. An Fc-fusion protein was inactivated by the times and pH values required for viral inactivation. A novel on-column low pH viral inactivation method was developed. The mAb humanized IgG1 was produced in recombinant Chinese hamster ovary (CHO) cells grown in serum free medium. As described in this example, antibodies were retained on protein A and CAPTO ADHERE® at pH 3.0 using 2 M ammonium sulfate to increase hydrophobic interactions. On-column xMuLV inactivation was demonstrated on protein A with 2 M ammonium sulfate pH 3-3.5, 1 M Arginine, and the detergent LDAO. On-column inactivation helps minimize low pH exposure, eliminates added conductivity during pool acidification, and automates low pH inactivation steps. On-column inactivation provides benefit for semi-continuous multi-column chromatography which generates many low pH inactivation pools. As described in this example antibodies were retained on CAPTO MMC® at pH 8.0 using 2 M ammonium sulfate to increase hydrophobic interactions.

The Fc-fusion protein was produced in HEK293 cells grown in serum free medium. Xenotropic murine leukemia virus (X-MLV) was measured with PCR and infectivity based assays. Table 15 shows xMulV virus inactivation and removal provided by protein A wash buffers with an Fc-fusion protein.

The protein A ligand binds the CH2 and CH3 domains of an antibody Fc through hydrophobic, ionic and hydrogen bond interactions. In one part of this example, a 6.6 mL MABSELECT™ SuRe column (19.4 cm) was loaded with 50 mL of HCCF with 2.2 mg/ml antibody. The column was washed with 100 mM BisTris buffer with 2000 mM ammonium sulfate at pH 6.6. A low pH wash buffer with ammonium sulfate was then applied (100 mM sodium citrate, 2000 mM ammonium sulfate at pH 3.0). The ammonium sulfate concentration was then reduced to zero over a 9 CV gradient. The flow rate for all steps was 250 cm/hr.

As shown in FIG. 12, the antibody began to desorb at about 1700 mM and was fully eluted at about 200 mM ammonium sulfate. FIG. 12 shows that at least 1700 mM ammonium sulfate is required to keep the antibody bound to protein A at pH 3.0. Since at least 1700 mM ammonium sulfate was required to keep the antibody bound to the resin at low pH, the solubility of the antibody was measured as a function of pH, antibody and ammonium sulfate concentration. The antibody was found to be soluble in 1000 mM ammonium sulfate but not 1500 mM ammonium sulfate. The precipitation was observed with 1500 mM ammonium sulfate at pH values between 3.5 and 8.0 and with antibody concentrations between 10 and 30 mg/mL.

In one part of this example, a 6.6 mL MABSELECT™ SuRe column (19.4 cm) was first equilibrated and then loaded to 25.8 g/L resin using 50 mL of antibody in HCCF. A flow rate of 250 cm/hr was used except during the regeneration step (50 cm/hr).

A pH 3.0, 2 M ammonium sulfate, 100 mM glycine wash was used to keep the antibody bound to the resin at low pH. The low pH, high ammonium sulfate wash was bracketed by a neutral, high ammonium sulfate wash buffer (pH 7.0, 2 M ammonium sulfate) to ensure that high levels of ammonium sulfate were present as the pH was lowered to 3.0 and also when it was subsequently raised to 7.0. Without this, significant product elution occurred before and after the wash step. Excess wash buffer was used at each step to ensure adequate buffer exchange. The step sequence and buffers used are identical to those used in Example 8. The protein concentration, conductivity, and pH in each step are shown in FIG. 8. FIG. 13 indicates that 2 M ammonium sulfate wash keeps antibody bound to protein A at pH 3.0.

In one part of this example, a 1.7 mL (5.0 cm) CAPTO ADHERE® column was first equilibrated and then loaded with 6 mL of 11.4 g/L antibody in pH 8.0 50 mM Tris buffer. Subsequently a high salt pH 8.0 wash buffer and then a high salt pH 3.5 wash buffer were applied to the resin. Excess wash buffer was used at each step to ensure adequate buffer exchange. All steps were performed at 100 cm/hr. See Table 16.

TABLE 15 xMulV virus inactivation and removal provided by protein A wash buffers with an Fc-fusion protein.

| Protein A wash buffer | Virus Removal by PCR | Combined Removal andInactivation by Infectivity |
|---|---|---|
| Low pH (pH 3.5, 2M ammonium sulfate) | 4.96 | >6.39 |
| Arginine (1M arginine pH 4.8) | >5.54 | >6.39 |
| Detergent (LDAO 4X CMC) | 5.11 | >6.39 |

TABLE 16

Step sequence and buffers used to produce FIG. 14 of Example 12.

| Step | Buffer | pH | Volume (CV or ml) |
|---|---|---|---|
| Equilibration | 50 mM Tris | 8.0 | 15 |
| Load | 50 mM Tris | 8.0 | 6 mL |
| Wash 1 | 50 mM Tris, 2M Ammonium Sulfate | 8.0 | 15 |
| Wash 2 | 100 mM Citrate 2M Ammonium Sulfate | 3.5 | 15 |
| Wash 3 | 50 mM Tris, 2M Ammonium Sulfate | 8.0 | 15 |
| Wash 4 | 50 mM Tris | 8.0 | 15 |
| Elution | 100 mM Citrate | 3.4 | 15 |
| Regeneration | 1.0N NaOH | | 15 |

FIG. 14 shows that 2 M ammonium sulfate wash keeps antibody bound to CAPTO ADHERE® at pH 3.5. As shown in FIG. 14, minimal product loss was observed during the 2 M ammonium sulfate, pH 3.5 wash, which is surprising because at this pH both the product and the resin have a positive charge. It is likely that the product remains bound to the resin due to enhanced hydrophobic interactions in this high salt buffer. The majority of the product (79.0%) was recovered in the elution pool. The percentage of the peak that was monomeric antibody (98.4%) was not altered by the high ammonium sulfate wash.

In one part of this example, a 1.7 mL (5.1 cm) column with CAPTO MMC® mixed mode resin was loaded with 6 mL of 12.4 mg/mL antibody in a pH 4.5, 50 mM citrate buffer. Subsequently a high salt pH 4.5 wash and then a high salt pH 8.0 wash were applied. Excess wash buffer was used at each step to ensure adequate buffer exchange. The protein concentration, conductivity, and pH in each step are shown in FIG. 15. The buffers used in each step are shown in Table 17. All steps were performed at 100 cm/hr.

TABLE 17

Step sequence and buffers used to produce FIG. 15 of Example 12.

| Step | Buffer | pH | Volume (CV or ml) |
|---|---|---|---|
| Equilibration | 50 mM Citrate | 4.5 | 15 |
| Load | 50 mM Citrate | 4.5 | 6 mL |
| Wash 1 | 50 mM Citrate, 2M Ammonium Sulfate | 4.5 | 15 |
| Wash 2 | 50 mM Tris, 2M Ammonium Sulfate | 8.0 | 15 |
| Elution | 50 mM Tris | 8.0 | 15 |
| Regeneration | 0.1N NaOH | | 15 |

FIG. 15 shows that 2 M ammonium sulfate wash keeps antibody bound to CAPTO MMC® at pH 8.0. As shown in FIG. 15, minimal product loss was observed during the 2 M ammonium sulfate, pH 8.0 wash, which is surprising because at this pH both the product and the resin have a negative charge and antibody elution would be expected to occur. The percent recovery in the eluate pool was 94.1%. It is likely that the product remains bound to the resin due to enhanced hydrophobic interactions in this high salt buffer.

A similar experiment was performed using TMAE HiCap resin. TMAE HiCap resin is an anion exchange resin that lacks the hydrophobic interaction properties of the CAPTO ADHERE™ resin. Significant product loss occurred during the low pH washes and the overall recovery was 49.8%. The product that eluted during the low pH wash precipitated in the column and in the instrumentation. The TMAE HiCap resin experiment indicates that kosmotropic salts were not capable of preserving adsorption of the mAb to the anion exchange resin at low pH.

The on-column low pH viral inactivation method shows that antibodies were retained on protein A and CAPTO ADHERE® at pH 3.0 using 2 M ammonium sulfate to increase hydrophobic interactions. On-column xMuLV inactivation was demonstrated on protein A with 2 M ammonium sulfate pH 3-3.5, 1 M Arginine, and the detergent LDAO.

These data show that on-column inactivation helps minimize low pH exposure, eliminates added conductivity during pool acidification, automates low pH inactivation step, and helps enable semi-continuous multi-column chromatography.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All documents, articles, publications, patents, and patent applications mentioned in this specification are herein incorporated by reference to the same extent as if each individual publication or patent application was specifically and individually indicated to be incorporated by reference.

The present application claims priority to U.S. Provisional Application No. 61/882,488, filed Sep. 25, 2014 and U.S. Provisional Application No. 62/028,657, filed Jul. 24, 2014, which are incorporated herein by reference in their entireties.

TABLE OF SEQUENCES

TABLE 15

Polynucleotide Sequences of FVIII

A. B-Domain Deleted FVIII-Fc (i) B-Domain Deleted FVIII-Fc Chain DNA Sequence (FVIII signal peptide underlined, Fc region in bold) (SEQ ID NO: 1, which encodes SEQ ID NO: 2)

```
  1  atgcaaatag agctctccac ctgcttcttt ctgtgccttt tgcgattctg 51  ctttagtgcc accagaagat actacctggg tgcagtggaa ctgtcatggg 101  actatatgca aagtgatctc ggtgagctgc ctgtggacgc aagatttcct 151  cctagagtgc caaaatcttt tccattcaac acctcagtcg tctacaaaaa 201  gactctgttt gtagaattca cggatcacct tttcaacatc gctaagccaa 251  ggccaccctg gatgggtctg ctaggtccta ccatccaggc tgaggtttat 301  gatacagtgg tcattacact taagaacatg gcttcccatc ctgtcagtct 351  tcatgctgtt ggtgtatcct actggaaagc ttctgaggga gctgaatatg 401  atgatcagac cagtcaaagg gagaaagaag atgataaagt cttccctggt 451  ggaagccata catatgtctg gcaggtcctg aaagagaatg gtccaatggc
```

TABLE 15-continued

Polynucleotide Sequences of FVIII

```
 501  ctctgaccca ctgtgcctta cctactcata tctttctcat gtggacctgg
 551  taaaagactt gaattcaggc ctcattggag ccctactagt atgtagagaa
 601  gggagtctgg ccaaggaaaa gacacagacc ttgcacaaat ttatactact
 651  ttttgctgta tttgatgaag ggaaaagttg gcactcagaa acaaagaact
 701  ccttgatgca ggatagggat gctgcatctg ctcgggcctg gcctaaaatg
 751  cacacagtca atggttatgt aaacaggtct ctgccaggtc tgattggatg
 801  ccacaggaaa tcagtctatt ggcatgtgat tggaatgggc accactcctg
 851  aagtgcactc aatattcctc gaaggtcaca catttcttgt gaggaaccat
 901  cgccaggcgt ccttggaaat ctcgccaata actttcctta ctgctcaaac
 951  actcttgatg gaccttggac agtttctact gttttgtcat atctcttccc
1001  accaacatga tggcatgaa gcttatgtca aagtagacag ctgtccagag
1051  gaaccccaac tacgaatgaa aaataatgaa gaagcggaag actatgatga
1101  tgatcttact gattctgaaa tggatgtggt caggtttgat gatgacaact
1151  ctccttcctt tatccaaatt cgctcagttg ccaagaagca tcctaaaact
1201  tgggtacatt acattgctgc tgaagaggag gactgggact atgctccctt
1251  agtcctcgcc cccgatgaca gaagttataa aagtcaatat ttgaacaatg
1301  gccctcagcg gattggtagg aagtacaaaa aagtccgatt tatggcatac
1351  acagatgaaa cctttaagac tcgtgaagct attcagcatg aatcaggaat
1401  cttgggacct ttactttatg gggaagttgg agacacactg ttgattatat
1451  ttaagaatca agcaagcaga ccatataaca tctaccctca cggaatcact
1501  gatgtccgtc ctttgtattc aaggagatta ccaaaaggtg taaaacattt
1551  gaaggatttt ccaattctgc caggagaaat attcaaatat aaatggacag
1601  tgactgtaga agatgggcca actaaatcag atcctcggtg cctgacccgc
1651  tattactcta gtttcgttaa tatggagaga gatctagctt caggactcat
1701  tggccctctc ctcatctgct acaaagaatc tgtagatcaa agaggaaacc
1751  agataatgtc agacaagagg aatgtcatcc tgttttctgt atttgatgag
1801  aaccgaagct ggtacctcac agagaatata caacgctttc tccccaatcc
1851  agctggagtg cagcttgagg atccagagtt ccaagcctcc aacatcatgc
1901  acagcatcaa tggctatgtt tttgatagtt tgcagttgtc agtttgtttg
1951  catgaggtgg catactggta cattctaagc attggagcac agactgactt
2001  cctttctgtc ttcttctctg gatataccttc caaacacaaa atggtctatg
2051  aagacacact caccctattc ccattctcag gagaaactgt cttcatgtcg
2101  atggaaaacc caggtctatg gattctgggg tcccacaact cagactttcg
2151  gaacagaggc atgaccgcct tactgaaggt ttctagttgt gacaagaaca
2201  ctggtgatta ttacgaggac agttatgaag atatttcagc atacttgctg
2251  agtaaaaaca atgccattga accaagaagc ttctctcaaa acccaccagt
2301  cttgaaacgc catcaacggg aaataactcg tactactctt cagtcagatc
2351  aagaggaaat tgactatgat gataccatat cagttgaaat gaagaaggaa
2401  gattttgaca tttatgatga ggatgaaaat cagagccccc gcagctttca
```

TABLE 15-continued

Polynucleotide Sequences of FVIII

```
2451  aaagaaaaca cgacactatt ttattgctgc agtggagagg ctctgggatt
2501  atgggatgag tagctcccca catgttctaa gaaacagggc tcagagtggc
2551  agtgtccctc agttcaagaa agttgttttc caggaattta ctgatggctc
2601  ctttactcag cccttatacc gtggagaact aaatgaacat tgggactcc
2651  tggggccata tataagagca gaagttgaag ataatatcat ggtaactttc
2701  agaaatcagg cctctcgtcc ctattccttc tattctagcc ttatttctta
2751  tgaggaagat cagaggcaag gagcagaacc tagaaaaaac tttgtcaagc
2801  ctaatgaaac caaaacttac ttttggaaag tccaacatca tatggcaccc
2851  actaaagaty agtttgactg caaagcctgg gcttatttct ctgatgttga
2901  cctggaaaaa gatgtgcact caggcctgat tggaccccttt ctggtctgcc
2951  acactaacac actgaaccct gctcatggga gacaagtgac agtacaggaa
3001  tttgctctgt ttttcaccat ctttgatgag accaaaagct ggtacttcac
3051  tgaaaatatg gaaagaaact gcagggctcc ctgcaatatc cagatggaag
3101  atcccacttt taaagagaat tatcgcttcc atgcaatcaa tggctacata
3151  atggatacac tacctggctt agtaatggct caggatcaaa ggattcgatg
3201  gtatctgctc agcatgggca gcaatgaaaa catccattct attcatttca
3251  gtggacatgt gttcactgta cgaaaaaaag aggagtataa aatggcactg
3301  tacaatctct atccaggtgt ttttgagaca gtggaaatgt taccatccaa
3351  agctggaatt tggcgggtgg aatgccttat tggcgagcat ctacatgctg
3401  ggatgagcac acttttctg gtgtacagca ataagtgtca gactcccctg
3451  ggaatggctt ctggacacat tagagatttt cagattacag cttcaggaca
3501  atatggacag tgggcccaa agctggccag acttcattat tccggatcaa
3551  tcaatgcctg gagcaccaag gagccctttt cttggatcaa ggtggatctg
3601  ttggcaccaa tgattattca cggcatcaag acccagggtg cccgtcagaa
3651  gttctccagc ctctacatct ctcagtttat catcatgtat agtcttgatg
3701  ggaagaagtg gcagacttat cgaggaaatt ccactggaac cttaatggtc
3751  ttctttggca atgtggattc atctgggata aaacacaata tttttaaccc
3801  tccaattatt gctcgataca tccgtttgca cccaactcat tatagcattc
3851  gcagcactct tcgcatggag ttgatgggct gtgatttaaa tagttgcagc
3901  atgccattgg gaatggagag taaagcaata tcagatgcac agattactgc
3951  ttcatcctac tttaccaata tgtttgccac ctggtctcct tcaaaagctc
4001  gacttcacct ccaagggagg agtaatgcct ggagacctca ggtgaataat
4051  ccaaaagagt ggctgcaagt ggacttccag aagacaatga aagtcacagg
4101  agtaactact cagggagtaa aatctctgct taccagcatg tatgtgaagg
4151  agttcctcat ctccagcagt caagatggcc atcagtggac tctctttttt
4201  cagaatggca agtaaaggt ttttcaggga aatcaagact ccttcacacc
4251  tgtggtgaac tctctagacc caccgttact gactcgctac cttcgaattc
4301  accccagag ttgggtgcac cagattgccc tgaggatgga ggttctgggc
4351  tgcgaggcac aggacctcta cgacaaaact cacacatgcc caccgtgccc
```

TABLE 15-continued

Polynucleotide Sequences of FVIII

```
4401  agctccagaa ctcctgggcg gaccgtcagt cttcctcttc cccccaaaac
4451  ccaaggacac cctcatgatc tcccggaccc ctgaggtcac atgcgtggtg
4501  gtggacgtga gccacgaaga ccctgaggtc aagttcaact ggtacgtgga
4551  cggcgtggag gtgcataatg ccaagacaaa gccgcgggag gagcagtaca
4601  acagcacgta ccgtgtggtc agcgtcctca ccgtcctgca ccaggactgg
4651  ctgaatggca aggagtacaa gtgcaaggtc tccaacaaag ccctcccagc
4701  ccccatcgag aaaaccatct ccaaagccaa agggcagccc cgagaaccac
4751  aggtgtacac cctgccccca tcccgggatg agctgaccaa gaaccaggtc
4801  agcctgacct gcctggtcaa aggcttctat cccagcgaca tcgccgtgga
4851  gtgggagagc aatgggcagc cggagaacaa ctacaagacc acgcctcccg
4901  tgttggactc cgacggctcc ttcttcctct acagcaagct caccgtggac
4951  aagagcaggt ggcagcaggg gaacgtcttc tcatgctccg tgatgcatga
5001  ggctctgcac aaccactaca cgcagaagag cctctccctg tctccgggta
5051  aa
```

(ii) Fc DNA sequence (mouse Igκ signal peptide underlined) (SEQ ID NO: 3, which encodes SEQ ID NO: 4)

```
  1  atggagacag acacactcct gctatgggta ctgctgctct gggttccagg
 51  ttccactggt gacaaaactc acacatgccc accgtgccca gcacctgaac
101  tcctgggagg accgtcagtc ttcctcttcc ccccaaaacc caaggacacc
151  ctcatgatct cccggacccc tgaggtcaca tgcgtggtgg tggacgtgag
201  ccacgaagac cctgaggtca agttcaactg gtacgtggac ggcgtggagg
251  tgcataatgc caagacaaag ccgcgggagg agcagtacaa cagcacgtac
301  cgtgtggtca gcgtcctcac cgtcctgcac caggactggc tgaatggcaa
351  ggagtacaag tccaaggtct ccaacaaagc cctcccagcc cccatcgaga
401  aaaccatctc caaagccaaa gggcagcccc gagaaccaca ggtgtacacc
451  ctgcccccat cccgcgatga gctgaccaag aaccaggtca gcctgacctg
501  cctggtcaaa ggcttctatc ccagcgacat cgccgtggag tgggagagca
551  atgggcagcc ggagaacaac tacaagacca cgcctcccgt gttggactcc
601  gacggctcct tcttcctcta cagcaagctc accgtggaca gagcaggtg
651  gcagcagggg aacgtcttct catgctccgt gatgcatgag gctctgcaca
701  accactacac gcagaagagc ctctccctgt ctccgggtaa a
```

B. Full Length FVIII-Fc (i) Full Length FVIII-Fc DNA Sequence (FVIII signal peptide underlined, Fc region in bold) (SEQ ID NO: 5, which encodes SEQ ID NO: 6)

```
  1  atgcaaatag agctctccac ctgcttcttt ctgtgccttt tgcgattctg
 51  ctttagtgcc accagaagat actacctggg tgcagtggaa ctgtcatggg
101  actatatgca agtgatctc ggtgagctgc ctgtggacgc aagatttcct
151  cctagagtgc caaatctttt ccattcaac acctcagtcg tctacaaaaa
201  gactctgttt gtagaattca cggatcacct tttcaacatc gctaagccaa
251  ggccaccctg atgggtctg ctaggtccta ccatccaggc tgaggtttat
301  gatacagtgg tcattacact taagaacatg gcttcccatc ctgtcagtct
```

TABLE 15-continued

Polynucleotide Sequences of FVIII

```
 351   tcatgctgtt ggtgtatcct actggaaagc ttctgaggga gctgaatatg
 401   atgatcagac cagtcaaagg gagaaagaag atgataaagt cttccctggt
 451   ggaagccata catatgtctg gcaggtcctg aaagagaatg gtccaatggc
 501   ctctgaccca ctgtgcctta cctactcata tctttctcat gtggacctgg
 551   taaaagactt gaattcaggc ctcattggag ccctactagt atgtagagaa
 601   gggagtctgg ccaaggaaaa gacacagacc ttgcacaaat ttatactact
 651   ttttgctgta tttgatgaag ggaaaagttg gcactcagaa acaaagaact
 701   ccttgatgca ggatagggat gctgcatctg ctcgggcctg gcctaaaatg
 751   cacacagtca atggttatgt aaacaggtct ctgccaggtc tgattggatg
 801   ccacaggaaa tcagtctatt ggcatgtgat tggaatgggc accactcctg
 851   aagtgcactc aatattcctc gaaggtcaca catttcttgt gaggaaccat
 901   cgccaggcgt ccttggaaat ctcgccaata actttcctta ctgctcaaac
 951   actcttgatg gaccttggac agtttctact gttttgtcat atctcttccc
1001   accaacatga tggcatggaa gcttatgtca agtagacag ctgtccagag
1051   gaaccccaac tacgaatgaa aaataatgaa gaagcggaag actatgatga
1101   tgatcttact gattctgaaa tggatgtggt caggtttgat gatgacaact
1151   ctccttcctt tatccaaatt cgctcagttg ccaagaagca tcctaaaact
1201   tgggtacatt acattgctgc tgaagaggag gactgggact atgctccctt
1251   agtcctcgcc cccgatgaca gaagttataa aagtcaatat ttgaacaatg
1301   gccctcagcg gattggtagg aagtacaaaa aagtccgatt tatggcatac
1351   acagatgaaa cctttaagac tcgtgaagct attcagcatg aatcaggaat
1401   cttgggacct ttactttatg gggaagttgg agacacactg ttgattatat
1451   ttaagaatca agcaagcaga ccatataaca tctaccctca cggaatcact
1501   gatgtccgtc ctttgtattc aaggagatta ccaaaaggtg taaaacattt
1551   gaaggatttt ccaattctgc caggagaaat attcaaatat aaatggacag
1601   tgactgtaga agatgggcca actaaatcag atcctcggtg cctgacccgc
1651   tattactcta gtttcgttaa tatggagaga gatctagctt caggactcat
1701   tggccctctc ctcatctgct acaaagaatc tgtagatcaa agaggaaacc
1751   agataatgtc agacaagagg aatgtcatcc tgttttctgt atttgatgag
1801   aaccgaagct ggtacctcac agagaatata caacgctttc tccccaatcc
1851   agctggagtg cagcttgagg atccagagtt ccaagcctcc aacatcatgc
1901   acagcatcaa tggctatgtt tttgatagtt tgcagttgtc agtttgtttg
1951   catgaggtgg catactggta cattctaagc attggagcac agactgactt
2001   cctttctgtc ttcttctctg gatatacctt caaacacaaa atggtctatg
2051   aagacacact caccctattc ccattctcag gagaaactgt cttcatgtcg
2101   atggaaaacc caggtctatg gattctgggg tgccacaact cagactttcg
2151   gaacagaggc atgaccgcct tactgaaggt ttctagttgt gacaagaaca
2201   ctggtgatta ttacgaggac agttatgaag atatttcagc atacttgctg
2251   agtaaaaaca atgccattga accaagaagc ttctcccaga attcaagaca
```

TABLE 15-continued

Polynucleotide Sequences of FVIII

```
2301  ccctagcact aggcaaaagc aatttaatgc caccacaatt ccagaaaatg
2351  acatagagaa gactgaccct tcgtttgcac acagaacacc tatgcctaaa
2401  atacaaaatg tctcctctag tgatttgttg atgctcttgc gacagagtcc
2451  tactccacat gggctatcct tatctgatct ccaagaagcc aaatatgaga
2501  cttttttctga tgatccatca cctggagcaa tagacagtaa taacagcctg
2551  tctgaaatga cacacttcag gccacagctc catcacagtg gggacatggt
2601  atttacccct gagtcaggcc tccaattaag attaaatgag aaactgggga
2651  caactgcagc aacagagttg aagaaacttg atttcaaagt ttctagtaca
2701  tcaaataatc tgatttcaac aattccatca gacaatttgg cagcaggtac
2751  tgataataca agttccttag acccccaag tatgccagtt cattatgata
2801  gtcaattaga taccactcta tttggcaaaa agtcatctcc ccttactgag
2851  tctggtggac ctctgagctt gagtgaagaa aataatgatt caaagttgtt
2901  agaatcaggt ttaatgaata gccaagaaag ttcatgggga aaaaatgtat
2951  cgtcaacaga gagtggtagg ttatttaaag ggaaaagagc tcatggacct
3001  gctttgttga ctaaagataa tgccttattc aaagttagca tctctttgtt
3051  aaagacaaac aaaacttcca ataattcagc aactaataga aagactcaca
3101  ttgatggccc atcattatta attgagaata gtccatcagt ctggcaaaat
3151  atattagaaa gtgacactga gtttaaaaaa gtgacacctt tgattcatga
3201  cagaatgctt atggacaaaa atgctacagc tttgaggcta aatcatatgt
3251  caaataaaac tacttcatca aaaaacatgg aaatggtcca acagaaaaaa
3301  gagggcccca ttccaccaga tgcacaaaat ccagatatgt cgttctttaa
3351  gatgctattc ttgccagaat cagcaaggtg gatacaaagg actcatggaa
3401  agaactctct gaactctggg caaggcccca gtccaaagca attagtatcc
3451  ttaggaccag aaaaatctgt ggaaggtcag aatttcttgt ctgagaaaaa
3501  caaagtggta gtaggaaagg gtgaatttac aaaggacgta ggactcaaag
3551  agatggtttt tccaagcagc agaaacctat ttcttactaa cttggataat
3601  ttacatgaaa ataatacaca caatcaagaa aaaaaaattc aggaagaaat
3651  agaaaagaag gaaacattaa tccaagagaa tgtagtttg cctcagatac
3701  atacagtgac tcgcactaag aatttcatga agaacctttt cttactgagc
3751  actaggcaaa atgtagaagg ttcatatgac ggggcatatg ctccagtact
3801  tcaagatttt aggtcattaa atgattcaac aaatagaaca aagaaacaca
3851  cagctcattt ctcaaaaaaa ggggaggaag aaaacttgga aggcttggga
3901  aatcaaacca gcaaattgt agagaaatat gcatgcacca caaggatatc
3951  tcctaataca agccagcaga attttgtcac gcaacgtagt aagagagctt
4001  tgaaacaatt cagactccca ctagaagaaa cagaacttga aaaaggata
4051  attgtggatg acacctcaac ccagtggtcc aaaaacatga acatttgac
4101  cccgagcacc ctcacacaga tagactacaa tgagaaggag aaaggggcca
4151  ttactcagtc tccccttatca gattgcctta cgaggagtca tagcatccct
4201  caagcaaata gatctccatt acccattgca aaggtatcat catttccatc
```

TABLE 15-continued

Polynucleotide Sequences of FVIII

```
4251  tattagacct atatatctga ccagggtcct attccaagac aactcttctc
4301  atcttccagc agcatcttat agaaagaaag attctggggt ccaagaaagc
4351  agtcatttct tacaaggagc aaaaaaaat aacctttctt tagccattct
4401  aaccttggag atgactggtg atcaaagaga gcttggctcc ctggggacaa
4451  gtgccacaaa ttcagtcaca tacaagaaag ttgagaacac tgttctcccg
4501  aaaccagact tgcccaaaac atctggcaaa gttgaattgc ttccaaaagt
4551  tcacatttat cagaaggacc tattccctac ggaaactagc aatgggtctc
4601  ctggccatct ggatctcgtg aagggagcc ttcttcaggg aacagaggga
4651  gcgattaagt ggaatgaagc aaacagacct ggaaaagttc cctttctgag
4701  agtagcaaca gaaagctctg caaagactcc ctccaagcta ttggatcctc
4751  ttgcttggga taaccactat ggtactcaga taccaaaaga gagtggaaa
4801  tcccaagaga agtcaccaga aaaaacagct tttaagaaaa aggataccat
4851  tttgtccctg aacgcttgtg aaagcaatca tgcaatagca gcaataaatg
4901  agggacaaaa taagcccgaa atagaagtca cctgggcaaa gcaaggtagg
4951  actgaaaggc tgtgctctca aaacccacca gtcttgaaac gccatcaacg
5001  ggaaataact cgtactactc ttcagtcaga tcaagaggaa attgactatg
5051  atgataccat atcagttgaa atgaagaagg aagattttga catttatgat
5101  gaggatgaaa atcagagccc ccgcagcttt caaaagaaaa cacgacacta
5151  ttttattgct gcagtggaga ggctctggga ttatgggatg agtagctccc
5201  cacatgttct aagaaacagg gctcagagtg gcagtgtccc tcagttcaag
5251  aaagttgttt tccaggaatt tactgatggc tcctttactc agccccttata
5301  ccgtggagaa ctaaatgaac atttgggact cctggggcca tatataagag
5351  cagaagttga agataatatc atggtaactt tcagaaatca ggcctctcgt
5401  ccctattcct tctattctag ccttatttct tatgaggaag atcagaggca
5451  aggagcagaa cctagaaaaa actttgtcaa gcctaatgaa accaaaactt
5501  acttttggaa agtgcaacat catatggcac ccactaaaga tgagtttgac
5551  tgcaaagcct gggcttattt ctctgatgtt gacctggaaa agatgtgca
5601  ctcaggcctg attggacccc ttctggtctg ccacactaac acactgaacc
5651  ctgctcatgg gagacaagtg acagtacagg aatttgctct gttttcacc
5701  atctttgatg agaccaaaag ctggtacttc actgaaaata tggaaagaaa
5751  ctgcagggct ccctgcaata tccagatgga agatcccact tttaaagaga
5801  attatcgctt ccatgcaatc aatggctaca taatggatac actacctggc
5851  ttagtaatgg ctcaggatca aaggattcga tggtatctgc tcagcatggg
5901  cagcaatgaa acatccatt ctattcattt cagtggacat gtgttcactg
5951  tacgaaaaaa agaggagtat aaaatggcac tgtacaatct ctatccaggt
6001  gtttttgaga cagtggaaat gttaccatcc aaagctggaa tttggcgggt
6051  ggaatgcctt attggcgagc atctacatgc tgggatgagc acactttttc
6101  tggtgtacag caataagtgt cagactcccc tgggaatggc ttctggacac
6151  attagagatt ttcagattac agcttcagga caatatggac agtgggcccc
```

TABLE 15-continued

Polynucleotide Sequences of FVIII

```
6201  aaagctggcc agacttcatt attccggatc aatcaatgcc tggagcacca
6251  aggagccctt ttcttggatc aaggtggatc tcttggcacc aatgattatt
6301  cacggcatca agacccaggg tgcccgtcag aagttctcca gcctctacat
6351  ctctcagttt atcatcatgt atagtcttga tcggaagaag tcgcagactt
6401  atcgaggaaa ttccactgga accttaatgg tcttctttgg caatgtggat
6451  tcatctggga taaaacacaa tattttttaac cctccaatta ttgctcgata
6501  catccgtttg cacccaactc attatagcat tcgcagcact cttcgcatgg
6551  agttgatggg ctgtgattta aatagttgca gcatgccatt gggaatggag
6601  agtaaagcaa tatcagatgc acagattact gcttcatcct actttaccaa
6651  tatgtttgcc acctggtctc cttcaaaagc tcgacttcac ctccaaggga
6701  ggagtaatgc ctggagacct caggtgaata atccaaaaga gtggctgcaa
6751  gtggacttcc agaagacaat gaaagtcaca ggagtaacta ctcagggagt
6801  aaaatctctg cttaccagca tgtatgtgaa ggagttcctc atctccagca
6851  gtcaagatgg ccatcagtgg actctctttt ttcagaatgg caaagtaaag
6901  gttttcagg gaaatcaaga ctccttcaca cctgtggtga actctctaga
6951  cccaccgtta ctgactcgct accttcgaat tcaccccag agttgggtgc
7001  accagattgc cctgaggatg gaggttctgg gctgcgaggc acaggacctc
7051  tac gacaaaa ctcacacatg cccaccgtgc ccagctccag aactcctggg
7101  cggaccgtca gtcttcctct tccccccaaa acccaaggac accctcatga
7151  tctcccggac ccctgaggtc acatgcgtgg tggtggacgt gagccacgaa
7201  gaccctgagg tcaagttcaa ctggtacgtg gacggcgtgg aggtgcataa
7251  tgccaagaca aagccgcggg aggagcagta caacagcacg taccgtgtgg
7301  tcagcgtcct caccgtcctg caccaggact ggctgaatgg caaggagtac
7351  aagtgcaagg tctccaacaa agccctccca gcccccatcg agaaaaccat
7401  ctccaaagcc aaagggcagc cccgagaacc acaggtgtac accctgcccc
7451  catcccggga tgagctgacc aagaaccagg tcagcctgac ctgcctggtc
7501  aaaggcttct atcccagcga catcgccgtg gagtgggaga gcaatgggca
7551  gccggagaac aactacaaga ccacgcctcc cgtgttggac tccgacggct
7601  ccttcttcct ctacagcaag ctcaccgtgg acaagagcag gtggcagcag
7651  gggaacgtct tctcatgctc cgtgatgcat gaggctctgc acaaccacta
7701  cacgcagaag agcctctccc tgtctccggg taaa
```

C. FVIII-Fc Heterodimer Hybrid (i) FVIII Heavy Chain (HC)-Fc DNA sequence (no linker between HC and Fc) (signal peptide underlined, Fc region in bold) (SEQ ID NO: 7, which encodes SEQ ID NO: 8)

```
  1  atgcaaatag agctctccac ctgcttcttt ctgtgccttt tgcgattctg
 51  ctttagtgcc accagaagat actacctggg tgcagtggaa ctgtcatggg
101  actatatgca aagtgatctc ggtgagctgc ctgtggacgc aagatttcct
151  cctagagtgc aaaatctttt ccattcaac acctcagtcg tgtacaaaaa
201  gactctgttt gtagaattca cggatcacct tttcaacatc gctaagccaa
251  ggccaccctg atgggtctg ctaggtccta ccatccaggc tgaggtttat
```

TABLE 15-continued

Polynucleotide Sequences of FVIII

```
 301  gatacagtgg tcattacact taagaacatg gcttcccatc ctgtcagtct
 351  tcatgctgtt ggtgtatcct actggaaagc ttctgaggga gctgaatatg
 401  atgatcagac cagtcaaagg gagaaagaag atgataaagt cttccctggt
 451  ggaagccata catatgtctg gcaggtcctg aaagagaatg gtccaatggc
 501  ctctgaccca ctgtgcctta cctactcata tcttcctcat gtggacctgg
 551  taaaagactt gaattcaggc ctcattggag ccctactagt atgtagagaa
 601  gggagtctgg ccaaggaaaa gacacagacc ttgcacaaat ttatactact
 651  ttttgctgta tttgatgaag ggaaaagttg gcactcagaa acaaagaact
 701  ccttgatgca ggatagggat gctgcatctg ctcgggcctg gcctaaaatg
 751  cacacagtca atggttatgt aaacaggtct ctgccaggtc tgattggatg
 801  ccacaggaaa tcagtctatt ggcatgtgat tggaatgggc accactcctg
 851  aagtgcactc aatattcctc gaaggtcaca catttcttgt gaggaaccat
 901  cgccaggcgt ccttggaaat ctcgccaata actttcctta ctgctcaaac
 951  actcttgatg daccttggac agtttctact gttttgtcat atctcttccc
1001  accaacatga tggcatggaa gcttatgtca aagtagacag ctgtccagag
1051  gaaccccaac tacgaatgaa aaataatgaa gaagcggaag actatgatga
1101  tgatcttact gattctgaaa tggatgtggt caggtttgat gatgacaact
1151  ctccttcctt tatccaaatt cgctcagttg ccaagaagca tcctaaaact
1201  tgggtacatt acattgctgc tgaagaggag gactgggact atgctccctt
1251  agtcctcgcc cccgatgaca gaagttataa aagtcaatat ttgaacaatg
1301  gccctcagcg gattggtagg aagtacaaaa aagtccgatt tatggcatac
1351  acagatgaaa cctttaagac tcgtgaagct attcagcatg aatcaggaat
1401  cttgggacct ttactttatg gggaagttgg agacacactg ttgattatat
1451  ttaagaatca agcaagcaga ccatataaca tctaccctca cggaatcact
1501  gatgtccgtc ctttgtattc aaggagatta ccaaaaggtg taaaacattt
1551  gaaggatttt ccaattctgc caggagaaat attcaaatat aaatggacag
1601  tgactgtaga agatgggcca actaaatcag atcctcggtg cctgacccgc
1651  tattactcta gtttcgttaa tatggagaga gatctagctt caggactcat
1701  tggccctctc ctcatctgct acaaagaatc tgtagatcaa agaggaaacc
1751  agataatgtc agacaagagg aatgtcatcc tgttttctgt atttgatgag
1801  aaccgaagct ggtacctcac agagaatata caacgctttc tccccaatcc
1851  agctggagtg cagcttgagg atccagagtt ccaagcctcc aacatcatgc
1901  acagcatcaa tggctatgtt tttgatagtt tgcagttgtc agtttgtttg
1951  catgaggtgg catactggta cattctaagc attggagcac agactgactt
2001  cctttctgtc ttcttctctg gatatacctt caaacacaaa atggtctatg
2051  aagacacact caccctattc ccattctcag gagaaactgt cttcatgtcg
2101  atggaaaacc caggtctatg gattctgggg tgccacaact cagactttcg
2151  gaacagaggc atgaccgcct tactgaaggt ttctagttgt gacaagaaca
2201  ctggtgatta ttacgaggac agttatgaag atatttcagc atacttgctg
```

TABLE 15-continued

Polynucleotide Sequences of FVIII

```
2251 agtaaaaaca atgccattga accaagagac aaaactcaca catgcccacc 2301 gtgcccagct ccagaactcc tgggcggacc gtcagtcttc ctcttccccc 2351 caaaacccaa ggacaccctc atgatctccc ggacccctga ggtcacatgc 2401 gtggtggtgg acgtgagcca cgaagaccct gaggtcaagt tcaactggta 2451 cgtggacggc gtggaggtgc ataatgccaa gacaaagccg cgggaggagc 2501 agtacaacag cacgtaccgt gtggtcagcg tcctcaccgt cctgcaccag 2551 gactggctga atggcaagga gtacaagtgc aaggtctcca acaaagccct 2601 cccagccccc atcgagaaaa ccatctccaa agccaaaggg cagccccgag 2651 aaccacaggt gtacaccctg cccccatccc gggatgagct gaccaagaac 2701 caggtcagcc tgacctgcct ggtcaaaggc ttctatccca gcgacatcgc 2751 cgtggagtgg gagagcaatg ggcagccgga gaacaactac aagaccacgc 2801 ctcccgtgtt ggactccgac ggctccttct tcctctacag caagctcacc 2851 gtggacaaga gcaggtggca gcagggaac gtcttctcat gctccgtgat 2901 gcatgaggct ctgcacaacc actacacgca gaagagcctc tccctgtctc 2951 cgggtaaa
```

(ii) FVIII Heavy Chain (HC)-Fc DNA sequence (5 amino acid linker between HC and Fc) (signal peptide underlined, Fc region in bold, 5 amino acid linker is double-underlined) (SEQ ID NO: 9, which encodes SEQ ID NO: 10)

```
   1 atgcaaatag agctctccac ctgcttcttt ctgtgccttt tgcgattctg 51 ctttagtgcc accagaagat actacctggg tgcagtggaa ctgtcatggg 101 actatatgca agtgatctc ggtgagctgc ctgtggacgc aagatttcct 151 cctagagtgc caaaatcttt tccattcaac acctcagtcg tgtacaaaaa 201 gactctgttt gtagaattca cggatcacct tttcaacatc gctaagccaa 251 ggccaccctg gatgggtctg ctaggtccta ccatccaggc tgaggtttat 301 gatacagtgg tcattacact taagaacatg gcttcccatc ctgtcagtct 351 tcatgctgtt ggtgtatcct actggaaagc ttctgaggga gctgaatatg 401 atgatcagac cagtcaaagg gagaaagaag atgataaagt cttccctggt 451 ggaagccata catatgtctg gcaggtcctg aaagagaatg gtccaatggc 501 ctctgaccca ctgtgcctta cctactcata tctttctcat gtggacctgg 551 taaaagactt gaattcaggc ctcattggag ccctactagt atgtagagaa 601 gggagtctgg ccaaggaaaa gacacagacc ttgcacaaat ttatactact 651 ttttgctgta tttgatgaag ggaaaagttg gcactcagaa acaaagaact 701 ccttgatgca ggataggat gctgcatctg ctcgggcctg gcctaaaatg 751 cacacagtca atggttatgt aaacaggtct ctgccaggtc tgattggatg 801 ccacaggaaa tcagtctatt ggcatgtgat tggaatgggc accactcctg 851 aagtgcactc aatattcctc gaaggtcaca catttcttgt gaggaaccat 901 cgccaggcgt ccttggaaat ctcgccaata ctttccttta ctgctcaaac 951 actcttgatg gaccttggac agtttctact gttttgtcat atctcttccc 1001 accaacatga tggcatggaa gcttatgtca agtagacag ctgtccagag 1051 gaaccccaac tacgaatgaa aaataatgaa gaagcggaag actatgatga
```

TABLE 15-continued

Polynucleotide Sequences of FVIII

```
1101  tgatcttact gattctgaaa tggatgtggt caggtttgat gatgacaact
1151  ctccttcctt tatccaaatt cgctcagttg ccaagaagca tcctaaaact
1201  tgggtacatt acattgctgc tgaagaggag gactgggact atgctcsctt
1251  agtcctcgcc cccgatgaca gaagttataa aagtcaatat tgaacaatg
1301  gccctcagcg gattggtagg aagtacaaaa aagtccgatt tatggcatac
1351  acagatgaaa cctttaagac tcgtgaagct attcagcatg aatcaggaat
1401  cttgggacct ttactttatg gggaagttgg agacacactg ttgattatat
1451  ttaagaatca agcaagcaga ccatataaca tctaccctca cggaatcact
1501  gatgtccgtc ctttgtattc aaggagatta ccaaaaggtg taaaacattt
1551  gaaggatttt ccaattctgc caggagaaat attcaaatat aaatggacag
1601  tgactgtaga agatgggcca actaaatcag atcctcggtg cctgacccgc
1651  tattactcta gtttcgttaa tatggagaga gatctagctt caggactcat
1701  tggccctctc ctcatctgct acaaagaatc tgtagatcaa agaggaaacc
1751  agataatgtc agacaagagg aatgtcatcc tcttttctgt atttgatgag
1801  aaccgaagct ggtacctcac agagaatata caacgctttc tccccaatcc
1851  agctggagtg cagcttgagg atccagagtt ccaagcctcc aacatcatgc
1901  acagcatcaa tggctatgtt tttgatagtt tgcagttgtc agtttgtttg
1951  catgaggtgg catactggta cattctaagc attggagcac agactgactt
2001  cctttctgtc ttcttctctg gatataccct caaacacaaa atggtctatg
2051  aagacacact caccctattc ccattctcag gagaaactgt cttcatgtcg
2101  atggaaaacc caggtctatg gattctgggg tcccacaact cagactttcg
2151  gaacagaggc atgaccgcct tactgaaggt ttctagttgt gacaagaaca
2201  ctggtgatta ttacgaggac agttatgaag atatttcagc atacttgctg
2251  agtaaaaaca atgccattga accaagaagc ttctcccaga atgacaaaac
2301  tcacacatgc ccaccgtgcc cagctccaga actcctgggc ggaccgtcag
2351  tcttcctctt ccccccaaaa cccaaggaca ccctcatgat ctcccggacc
2401  cctgaggtca catgcgtggt ggtggacgtg agccacgaag accctgaggt
2451  caagttcaac tggtacgtgg acggcgtgga ggtgcataat gccaagacaa
2501  agccgcggga ggagcagtac aacagcacgt accgtgtggt cagcgtcctc
2551  accgtcctgc accaggactg gctgaatggc aaggagtaca gtgcaaggt
2601  ctccaacaaa gccctcccag cccccatcga gaaaaccatc tccaaagcca
2651  aagggcagcc ccgagaacca caggtgtaca ccctgccccc atcccgggat
2701  gagctgacca agaaccaggt cagcctgacc tgcctggtca aaggcttcta
2751  tcccagcgac atcgccgtgg agtgggagag caatgggcag ccggagaaca
2801  actacaagac cacgcctccc gtgttggact ccgacggctc cttcttcctc
2851  tacagcaagc tcaccgtgga caagagcagg tggcagcagg ggaacgtctt
2901  ctcatgctcc gtgatgcatg aggctctgca caaccactac acgcagaaga
2951  gcctctccct gtctccgggt aaa
```

TABLE 15-continued

Polynucleotide Sequences of FVIII (iii) FVIII Light Chain (LC)-Fc DNA sequence (signal peptide underlined, Fc region in bold) (SEQ ID NO: 11, which encodes SEQ ID NO: 12)

```
   1  atggagacag acacactcct gctatgggta ctgctgctct gggttccagg
  51  ttccactggt gaaataactc gtactactct tcagtcagat caagaggaaa
 101  ttgactatga tgataccata tcagttgaaa tgaagaagga agattttgac
 151  atttatgatg aggatgaaaa tcagagcccc cgcagctttc aaaagaaaac
 201  acgacactat tttattgctg cagtggagag gctctgggat tatgggatga
 251  gtagctcccc acatgttcta agaaacaggg ctcagagtgg cagtgtccct
 301  cagttcaaga agttgttttt ccaggaattt actgatggct cctttactca
 351  gcccttatac cgtggagaac taaatgaaca tttgggactc ctggggccat
 401  atataagagc agaagttgaa gataatatca tcgtaacttt cagaaatcag
 451  gcctctcgtc cctattcctt ctattctagc cttatttctt atgaggaaga
 501  tcagaggcaa ggagcagaac tagaaaaaaa ctttgtcaag cctaatgaaa
 551  ccaaaactta cttttggaaa gtgcaacatc atatggcacc cactaaagat
 601  gagtttgact gcaaagcctg gcttatttc tctgatgttg acctggaaaa
 651  agatgtgcac tcaggcctga ttggacccct tctggtctgc cacactaaca
 701  cactgaaccc tgctcatggg agacaagtga cagtacagga atttgctctg
 751  ttttttcacca tctttgatga gaccaaaagc tggtacttca ctgaaaatat
 801  ggaaagaaac tgcagggctc cctgcaatat ccagatggaa gatcccactt
 851  ttaaagagaa ttatcgcttc catgcaatca atggctacat aatggataca
 901  ctacctggct tagtaatggc tcaggatcaa aggattcgat ggtatctgct
 951  cagcatgggc agcaatgaaa acatccattc tattcatttc agtggacatg
1001  tgttcactgt acgaaaaaaa gaggagtata aaatggcact gtacaatctc
1051  tatccaggtg tttttgagac agtggaaatg ttaccatcca agctggaat
1101  ttggcgggtg gaatgcctta ttggcgagca tctacatgct gggatgagca
1151  cacttttctt ggtgtacagc aataagtgtc agactcccct gggaatggct
1201  tctggacaca ttagagattt tcagattaca gcttcaggac aatatggaca
1251  gtgggcccca agctggcca gacttcatta ttccggatca atcaatgcct
1301  ggagcaccaa ggagcccttt tcttggatca aggtggatct gttggcacca
1351  atgattattc acggcatcaa gacccagggt gcccgtcaga agttctccag
1401  cctctacatc tctcagttta tcatcatgta tagtcttgat gggaagaagt
1451  ggcagactta tcgaggaaat tccactggaa ccttaatggt cttctttggc
1501  aatgtggatt catctgggat aaaacacaat atttttaacc ctccaattat
1551  tgctcgatac atccgtttgc acccaactca ttatagcatt cgcagcactc
1601  ttcgcatgga gttgatgggc tgtgatttaa atagttgcag catgccattg
1651  ggaatggaga gtaaagcaat atcagatgca cagattactg cttcatccta
1701  ctttaccaat atgtttgcca cctggtctcc ttcaaaagct cgacttcacc
1751  tccaagggag gagtaatgcc tggagacctc aggtaataa tccaaaagag
1801  tcgctgcaag tggacttcca gaagacaatg aaagtcacag gagtaactac
1851  tcagggagta aaatctctgc ttaccagcat gtatgtgaag gagttcctca
```

TABLE 15-continued

Polynucleotide Sequences of FVIII

```
1901  tctccagcag tcaagatggc catcagtgga ctctcttttt tcagaatggc 1951  aaagtaaagg tttttcaggg aaatcaagac tccttcacac ctgtggtgaa 2001  ctctctagac ccaccgttac tgactcgcta ccttcgaatt cacccccaga 2051  gttgggtgca ccagattgcc ctgaggatgg aggttctggg ctgcgaggca 2101  caggacctct ac gacaaaac tcacacatgc ccaccgtgcc cagctccaga 2151  actcctgggc ggaccgtcag tcttcctctt ccccccaaaa cccaaggaca 2201  ccctcatgat ctcccggacc cctgaggtca catgcgtggt ggtggacgtg 2251  agccacgaag accctgaggt caagttcaac tggtacgtgg acggcgtgga 2301  ggtgcataat gccaagacaa agccgcggga ggagcagtac aacagcacgt 2351  accgtgtggt cagcgtcctc accgtcctgc accaggactg gctgaatggc 2401  aaggagtaca agtgcaaggt ctccaacaaa gccctcccag cccccatcga 2451  gaaaaccatc tccaaagcca agggcagcc cgagaaccca caggtgtaca 2501  ccctgccccc atcccgggat gagctgacca agaaccaggt cagcctgacc 2551  tgcctggtca aaggcttcta tcccagcgac atcgccgtgg agtgggagag 2601  caatgggcag ccggagaaca actacaagac cacgcctccc gtgttggact 2651  ccgacggctc cttcttcctc tacagcaagc tcaccgtgga caagagcagg 2701  tggcagcagg ggaacgtctt ctcatgctcc gtgatgcatg aggctctgca 2751  caaccactac acgcagaaga gcctctccct gtctccgggt aaa
```

TABLE 16

Polypeptide Sequences of FVIII

A. B-Domain Deleted FVIII-Fc Monomer Hybrid (BDD FVIIIFc monomer dimer): created by coexpressing BDD FVIIIFc and Fc chains.

Construct = HC-LC-Fc fusion. An Fc expression cassette is cotransfectedwith BDDFVIII-Fc to generate the BDD FVIIIFc monomer. -. For the BDD FVIIIFc chain, the Fc sequence is shown in bold; HC sequence is shown in double underline; remaining B domain sequence is shown in italics. Signal peptides are underlined.

i) B domain deleted FVIII-Fc chain (19 amino acid signal sequence underlined) (SEQ ID NO: 2)

```
   1 MQIELSTCFF LCLLRFCFSA TRRYYLGAVE LSWDYMQSDL GELPVDARFP
  51 PRVPKSFPFN TSVVYKKTLF VEFTDHLFNI AKPRPPWMGL LGPTIQAEVY
 101 DTVVITLKNM ASHPVSLHAV GVSYWKASEG AEYDDQTSQR EKEDDKVFPG
 151 GSHTYVWQVL KENGPMASDP LCLTYSYLSH VDLVKDLNSG LIGALLVCRE
 201 GSLAKEKTQT LHKFILLFAV FDEGKSWHSE TKNSLMQDRD AASARAWPKM
 251 HTVNGYVNRS LPGLIGCHRK SVYWHVIGMG TTPEVHSIFL EGHTFLVRNH
 301 RQASLEISPI TFLTAQTLLM DLGQFLLFCH ISSHQHDGME AYVKVDSCPE
 351 EPQLRMKNNE EAEDYDDDLT DSEMDVVRFD DDNSPSFIQI RSVAKKHPKT
 401 WVHYIAAEEE DWDYAPLVLA PDDRSYKSQY LNNGPQRIGR KYKKVRFMAY
 451 TDETFKTREA IQHESGILGP LLYGEVGDTL LIIFKNQASR PYNIYPHGIT
 501 DVRPLYSRRL PKGVKHLKDF PILPGEIFKY KWTVTVEDGP TKSDPRCLTR
 551 YYSSFVNMER DLASGLIGPL LICYKESVDQ RGNQIMSDKR NVILFSVFDE
 601 NRSWYLTENI QRFLPNPAGV QLEDPEFQAS NIMHSINGYV FDSLQLSVCL
 651 HEVAYWYILS IGAQTDFLSV FFSGYTFKHK MVYEDTLTLF PFSGETVFMS
 701 MENPGLWILG CHNSDFRNRG MTALLKVSSC DKNTGDYYED SYEDISAYLL
 751 SKNNAIEPRS FSQNPPVLKR HQREITRTTL QSDQEEIDYD DTISVEMKKE
 801 DFDIYDEDEN QSPRSFQKKT RHYFIAAVER LWDYGMSSSP HVLRNRAQSG
 851 SVPQFKKVVF QEFTDGSFTQ PLYRGELNEH LGLLGPYIRA EVEDNIMVTF
 901 RNQASRPYSF YSSLISYEED QRQGAEPRKN FVKPNETKTY FWKVQHHMAP
 951 TKDEFDCKAW AYFSDVDLEK DVHSGLIGPL LVCHTNTLNP AHGRQVTVQE
1001 FALFFTIFDE TKSWYFTENM ERNCRAPCNI QMEDPTFKEN YRFHAINGYI
1051 MDTLPGLVMA QDQRIRWYLL SMGSNENIHS IHFSGHVFTV RKKEEYKMAL
1101 YNLYPGVFET VEMLPSKAGI WRVECLIGEH LHAGMSTLFL VYSNKCQTPL
1151 GMASGHIRDF QITASGQYGQ WAPKLARLHY SGSINAWSTK EPFSWIKVDL
1201 LAPMIIHGIK TQGARQKFSS LYISQFIIMY SLDGKKWQTY RGNSTGTLMV
```

TABLE 16-continued

Polypeptide Sequences of FVIII

```
1251 FFGNVDSSGI KHNIFNPPII ARYIRLHPTH YSIRSTLRME LMGCDLNSCS
1301 MPLGMESKAI SDAQITASSY FTNMFATWSP SKARLHLQGR SNAWRPQVNN
1351 PKEWLQVDFQ KTMKVTGVTT QGVKSLLTSM YVKEFLISSS QDGHQWTLFF
1401 QNGKVKVFQG NQDSFTPVVN SLDPPLLTRY LRIHPQSWVH QIALRMEVLG
1451 CEAQDLY**DKT HTCPPCPAPE LLGGPSVFLF PPKPKDTLMI SRTPEVTCVV
1501 VDVSHEDPEV KFNWYVDGVE VHNAKTKPRE EQYNSTYRVV SVLTVLHQDW
1551 LNGKEYKCKV SNKALPAPIE KTISKAKGQP REPQVYTLPP SRDELTKNQV
1601 SLTCLVKGFY PSDIAVEWES NGQPENNYKT TPPVLDSDGS FFLYSKLTVD
1651 KSRWQQGNVF SCSVMHEALH NHYTQKSLSL SPGK**
``` ii) Fc chain (20 amino acid heterologous signal peptide from mouse Igκ chain underlined) (SEQ ID NO: 4)

```
  1 METDTLLLWV LLLWVPGSTG DKTHTCPPCP APELLGGPSV FLFPPKPKDT
 51 LMISRTPEVT CVVVDVSHED PEVKFNWYVD GVEVHNAKTK PREEQYNSTY
101 RVVSVLTVLH QDWLNGKEYK CKVSNKALPA PIEKTISKAK GQPREPQVYT
151 LPPSRDELTK NQVSLTCLVK GFYPSDIAVE WESNGQPENN YKTTPPVLDS
201 DGSFFLYSKL TVDKSRWQQG NVFSCSVMHE ALHNHYTQKS LSLSPGK
```

B. Full length FVIIIFc monomer hybrid (Full length FVIIIFc monomer dimer): created by coexpressing FVIIIFc and Fc chains.

Construct = HC-B-LC-Fc fusion. An Fc expression cassette is cotransfected with full length FVIII-Fc to generate the full length FVIIIFc monomer. For the FVIIIFc chain, the Fc sequence is shown in bold; HC sequence is shown in double underline; B domain sequence is shown in italics. Signal peptides are underlined.

i) Full length FVIIIFc chain (FVIII signal peptide underlined (SEQ ID NO: 6)

```
   1 MQIELSTCFF LCLLRFCFSA TRRYYLGAVE LSWDYMQSDL GELPVDARFP
  51 PRVPKSFPFN TSVVYKKTLF VEFTDHLFNI AKPRPPWMGL LGPTIQAEVY
 101 DTVVITLKNM ASHPVSLHAV GVSYWKASEG AEYDDQTSQR EKEDDKVFPG
 151 GSHTYVWQVL KENGPMASDP LCLTYSYLSH VDLVKDLNSG LIGALLVCRE
 201 GSLAKEKTQT LHKFILLFAV FDEGKSWHSE TKNSLMQDRD AASARAWPKM
 251 HTVNGYVNRS LPGLIGCHRK SVYWHVIGMG TTPEVHSIFL EGHTFLVRNH
 301 RQASLEISPI TFLTAQTLLM DLGQFLLFCH ISSHQHDGME AYVKVDSCPE
 351 EPQLRMKNNE EAEDYDDDLT DSEMDVVRFD DDNSPSFIQI RSVAKKHPKT
 401 WVHYIAAEEE DWDYAPLVLA PDDRSYKSQY LNNGPQRIGR KYKKVRFMAY
 451 TDETFKTREA IQHESGILGP LLYGEVGDTL LIIFKNQASR PYNIYPHGIT
 501 DVRPLYSRRL PKGVKHLKDF PILPGEIFKY KWTVTVEDGP TKSDPRCLTR
 551 YYSSFVNMER DLASGLIGPL LICYKESVDQ RGNQIMSDKR NVILFSVFDE
 601 NRSWYLTENI QRFLPNPAGV QLEDPEFQAS NIMHSINGYV FDSLQLSVCL
 651 HEVAYWYILS IGAQTDFLSV FFSGYTFKHK MVYEDTLTLF PFSGETVEMS
 701 MENPGLWILG CHNSDFRNRG MTALLKVSSC DKNTGDYYED SYEDISAYLL
 751 SKNNAIEPRS FSQNSRHPST RQKQFNATTI PENDIEKTDP WFAHRTPMPK
 801 IQNVSSSDLL MLLRQSPTPH GLSLSDLQEA KYETFSDDPS PGAIDSNNSL
 851 SEMTHFRPQL HHSGDMVFTP ESGLQLRLNE KLGTTAATEL KKLDFKVSST
 901 SNNLISTIPS DNLAAGTDNT SSLGPPSMPV HYDSQLDTTL FGKKSSPLTE
 951 SGGPLSLSEE NNDSKLLESG LMNSQESSWG KNVSSTESGR LFKGKRAHGP
1001 ALLTKDNALF KVSISLLKTN KTSNNSATNR KTHIDGPSLL IENSPSVWQN
1051 ILESDTEFKK VTPLIHDRML MDKNATALRL NHMSNKTTSS KNMEMVQQKK
1101 EGPIPPDAQN PDMSFFKMLF LPESARWIQR THGKNSLNSG QGSPKQLVS
1151 LGPEKSVEGQ NFLSEKNKVV VGKGEFTKDV GLKEMVFPSS RNLFLTNLDN
1201 LHENNTHNQE KKIQEEIEKK ETLIQENVVL PQIHTVTGTK NFMKNLFLLS
1251 TRQNVEGSYD GAYAPVLQDF RSLNDSTNRT KKHTAHFSKK GEEENLEGLG
1301 NQTKQIVEKY ACTTRISPNT SQQNFVTQRS KRALKQFRLP LEETELEKRI
1351 IVDDTSTQWS KNMKHLTPST LTQIDYNEKE KGAITQSPLS DCLTRSHSIP
1401 QANRSPLPIA KVSSFPSIRP IYLTRVLFQD NSSHLPAASY RKKDSGVQES
1451 SHFLQGAKKN NLSLAILTLE MTGDQREVGS LGTSATNSVT YKKVENTVLP
1501 KPDLPKTSGK VELLPKVHIY QKDLFPTETS NGSPGHLDLV EGSLLQGTEG
1551 AIKWNEANRP GKVPFLRVAT ESSAKTPSKL LDPLAWDNHY GTQIPKEEWK
1601 SQEKSPEKTA FKKKDTILSL NACESNHAIA AINEGQNKPE IEVTWAKQGR
1651 TERLCSQNPP VLKRHQREIT RTTLQSDQEE IDYDDTISVE MKKEDFDIYD
1701 EDENQSPRSF QKKTRHYFIA AVERLWDYGM SSSPHVLRNR AQSGSVPQFK
1751 KVVFQEFTDG SFTQPLYRGE LNEHLGLLGP YIRAEVEDNI MVTFRNQASR
1801 PYSFYSSLIS YEEDQRGAE PRKNFVKPNE TKTYFWKVQH HMAPTKDEFD
1851 CKAWAYFSDV DLEKDVHSGL IGPLLVCHTN TLNPAHGRQV TVQEFALFFT
1901 IFDETKSWYF TENMERNCRA PCNIQMEDPT FKENYRFHAI NGYIMDTLPG
1951 LVMAQDQRIR WYLLSMGSNE NIHSIHFSGH VFTVRKKEEY KMALYNLYPG
2001 VFETVEMLPS KAGIWRVECL IGEHLHAGMS TLFLVYSNKC QTPLGMASGH
2051 IRDFQITASG QYGQWAPKLA RLHYSGSINA WSTKEPFSWI KVDLLAPMII
2101 HGIKTQGARQ KFSSLYISQF IIMYSLDGKK WQTYRGNSTG TLMVFFGNVD
2151 SSGIKHNIFN PPIIARYIRL HPTHYSIRST LRMELMGCDL NSCSMPLGME
2201 SKAISDAQIT ASSYFTNMFA TWSPSKARLH LQGRSNAWRP QVNNPKEWLQ
2251 VDFQKTMKVT GVTTQGVKSL LTSMYVKEFL ISSSQDGHQW TLFFQNGKVK
2301 VFQGNQDSFT PVVNSLDPPL LTRYLRIHPQ SWVHQIALRM EVLGCEAQDL
```

TABLE 16-continued

Polypeptide Sequences of FVIII

```
2351 YDKTHTCPPC PAPELLGGPS VFLFPPKPKD TLMISRTPEV TCVVVDVSHE
2401 DPEVKFNWYV DGVEVHNAKT KPREEQYNST YRVVSVLTVL HQDWLNGKEY
2451 KCKVSNKALP APIEKTISKA KGQPREPQVY TLPPSRDELT KNQVSLTCLV
2501 KGFYPSDIAV EWESNGQPEN NYKTTPPVLD SDGSFFLYSK LTVDKSRWQQ
2551 GNVFSCSVMH EALHNHYTQK SLSLSPGK
```

C. FVIII-Fc Heterodimer Hybrid

This is made by cotransfecting HC-Fc and LC-Fc constructs. Two HC-Fc constructs have been made. One has no linker between HC and Fc (HC-Fc) while the other has a 5 amino acid linker between HC and Fc (HC + 5-Fc). The FVIII signal peptide was used for the HC-Fc constructs, while the mouse Igκ signal sequence was used for the LC-Fc construct.

(i) HC-Fc (Fc sequence is shown in bold, signal peptide underlined) (SEQ ID NO: 8)
```
  1 MQIELSTCFF LCLLRFCFSA TRRYYLGAVE LSWDYMQSDL GELPVDARFP
 51 PRVPKSFPFN TSVVYKKTLF VEFTDHLFNI AKPRPPWMGL LGPTIQAEVY
101 DTVVITLKNM ASHPVSLHAV GVSYWKASEG AEYDDQTSQR EKEDDKVFPG
151 GSHTYVWQVL KENGPMASDP LCLTYSYLSH VDLVKDLNSG LIGALLVCRE
201 GSLAKEKTQT LHKFILLFAV FDEGKSWHSE TKNSLMQDRD AASARAWPKM
251 HTVNGYVNRS LPGLIGCHRK SVYWHVIGMG TTPEVHSIFL EGHTFLVRNH
301 RQASLEISPI TFLTAQTLLM DLGQFLLFCH ISSHQHDGME AYVKVDSCPE
351 EPQLRMKNNE EAEDYDDDLT DSEMDVVRFD DDNSPSFIQI RSVAKKHPKT
401 WVHYIAAEEE DWDYAPLVLA PDDRSYKSQY LNNGPQRIGR KYKKVRFMAY
451 TDETFKTREA IQHESGILGP LLYGEVGDTL LIIFKNQASR PYNIYPHGIT
501 DVRPLYSRRL PKGVKHLKDF PILPGEIFKY KWTVTVEDGP TKSDPRCLTR
551 YYSSFVNMER DLASGLIGPL LICYKESVDQ RGNQIMSDKR NVILFSVFDE
601 NRSWYLTENI QRFLPNPAGV QLEDPEFQAS NIMHSINGYV FDSLQLSVCL
651 HEVAYWYILS IGAQTDFLSV FFSGYTFKHK MVYEDTLTLF PFSGETVEMS
701 MENPGLWILG CHNSDFRNRG MTALLKVSSC DKNTGDYYED SYEDISAYLL
751 SKNNAIEPRD KTHTCPPCPA PELLGGPSVF LFPPKPKDTL MISRTPEVTC
801 VVVDVSHEDP EVKFNWYVDG VEVHNAKTKP REEQYNSTYR VVSVLTVLHQ
851 DWLNGKEYKC KVSNKALPAP IEKTISKAKG QPREPQVYTL PPSRDELTKN
901 QVSLTCLVKG FYPSDIAVEW ESNGQPENNY KTTPPVLDSD GSFFLYSKLT
951 VDKSRWQQGN VFSCSVMHEA LHNHYTQKSL SLSPGK
```

(ii) HC + 5-Fc (Fc sequence is shown in bold, 5 amino acid linker sequence (from the B domain of FVIII) is shown in italics, signal peptide underlined. )(SEQ ID NO: 10)
```
  1 MQIELSTCFF LCLLRFCFSA TRRYYLGAVE LSWDYMQSDL GELPVDARFP
 51 PRVPKSFPFN TSVVYKKTLF VEFTDHLFNI AKPRPPWMGL LGPTIQAEVY
101 DTVVITLKNM ASHPVSLHAV GVSYWKASEG AEYDDQTSQR EKEDDKVFPG
151 GSHTYVWQVL KENGPMASDP LCLTYSYLSH VDLVKDLNSG LIGALLVCRE
201 GSLAKEKTQT LHKFILLFAV FDEGKSWHSE TKNSLMQDRD AASARAWPKM
251 HTVNGYVNRS LPGLIGCHRK SVYWHVIGMG TTPEVHSIFL EGHTFLVRNH
301 RQASLEISPI TFLTAQTLLM DLGQFLLFCH ISSHQHDGME AYVKVDSCPE
351 EPQLRMKNNE EAEDYDDDLT DSEMDVVRFD DDNSPSFIQI RSVAKKHPKT
401 WVHYIAAEEE DWDYAPLVLA PDDRSYKSQY LNNGPQRIGR KYKKVRFMAY
451 TDETFKTREA IQHESGILGP LLYGEVGDTL LIIFKNQASR PYNIYPHGIT
501 DVRPLYSRRL PKGVKHLKDF PILPGEIFKY KWTVTVEDGP TKSDPRCLTR
551 YYSSFVNMER DLASGLIGPL LICYKESVDQ RGNQIMSDKR NVILFSVFDE
601 NRSWYLTENI QRFLPNPAGV QLEDPEFQAS NIMHSINGYV FDSLQLSVCL
651 HEVAYWYILS IGAQTDFLSV FFSGYTFKHK MVYEDTLTLF PFSGETVEMS
701 MENPGLWILG CHNSDFRNRG MTALLKVSSC DKNTGDYYED SYEDISAYLL
751 SKNNAIEPRS FSQNDKTHTC PPCPAPELLG GPSVFLFPPK PKDTLMISRT
801 PEVTCVVVDV SHEDPEVKFN WYVDGVEVHN AKTKPREEQY NSTYRVVSVL
851 TVLHQDWLNG KEYKCKVSNK ALPAPIEKTI SKAKGQPREP QVYTLPPSRD
901 ELTKNQVSLT CLVKGFYPSD IAVEWESNGQ PENNYKTTPP VLDSDGSFFL
951 YSKLTVDKSR WQQGNVFSCS VMHEALHNHY TQKSLSLSPG K
```

(iii) LC-Fc6His (Fc sequence is shown in bold, signal peptide underlined.) (SEQ ID NO: 12)
```
  1 METDTLLLWV LLLWVPGSTG EITRTTLQSD QEEIDYDDTI SVEMKKEDFD
 51 IYDEDENQSP RSFQKKTRHY FIAAVERLWD YGMSSSPHVL RNRAQSGSVP
101 QFKKVVFQEF TDGSFTQPLY RGELNEHLGL LGPYIRAEVE DNIMVTFRNQ
151 ASRPYSFYSS LISYEEDQRQ GAEPRKNFVK PNETKTYFWK VQHHMAPTKD
201 EFDCKAWAYF SDVDLEKDVH SGLIGPLLVC HTNTLNPAHG RQVTVQEFAL
251 FFTIFDETKS WYFTENMERN CRAPCNIQME DPTFKENYRF HAINGYIMDT
301 LPGLVMAQDQ RIRWYLLSMG SNENIHSIHF SGHVFTVRKK EEYKMALYNL
351 YPGVFETVEM LPSKAGIWRV ECLIGEHLHA GMSTLFLVYS NKCQTPLGMA
401 SGHIRDFQIT ASGQYGQWAP KLARLHYSGS INAWSTKEPF SWIKVDLLAP
451 MIIHGIKTQG ARQKFSSLYI SQFIIMYSLD GKKWQTYRGN STGTLMVFFG
501 NVDSSGIKHN IFNPPIIARY IRLHPTHYSI RSTLRMELMG CDLNSCSMPL
551 GMESKAISDA QITASSYFTN MFATWSPSKA RLHLQGRSNA WRPQVNNPKE
601 WLQVDFQKTM KVTGVTTQGV KSLLTSMYVK EFLISSSQDG HQWTLFFQNG
651 KVKVFQGNQD SFTPVVNSLD PPLLTRYLRI HPQSWVHQIA LRMEVLGCEA
```

TABLE 16-continued

Polypeptide Sequences of FVIII

```
701 QDLYDKTHTC PPCPAPELLG GPSVFLFPPK PKDTLMISRT PEVTCVVVDV
751 SHEDPEVKFN WYVDGVEVHN AKTKPREEQY NSTYRVVSVL TVLHQDWLNG
801 KEYKCKVSNK ALPAPIEKTI SKAKGQPREP QVYTLPPSRD ELTKNQVSLT
851 CLVKGFYPSD IAVEWESNGQ PENNYKTTPP VLDSDGSFFL YSKLTVDKSR
901 WQQGNVFSCS VMHEALHNHY TQKSLSLSPG K
```

TABLE 17

Polynucleotide Sequences of FIX

FIX-Fc Chain DNA Sequence (FIX signal peptide underlined, FIX sequence double underlined, Fc region in bold) (SEQ ID NO: 13, which encodes SEQ ID NO: 14)

pSYN-FIX-030 Nucleotide sequence (nt 1 to 7583):

FIX exon 1 (signal peptide, 1st amino acid propeptide): nt 690-777
FIX mini intron: nt 778-1076
FIX sequence: nt 1077-2371
Fc: nt 2372-3052

```
   1 gcgcgcgttg acattgatta ttgactagtt attaatagta atcaattacg
  51 gggtcattag ttcatagccc atatatggag ttccgcgtta cataacttac
 101 ggtaaatggc ccgcctggct gaccgcccaa cgacccccgc ccattgacgt
 151 caataatgac gtatgttccc atagtaacgc caatagggac tttccattga
 201 cgtcaatggg tggagtattt acggtaaact gcccacttgg cagtacatca
 251 agtgtatcat atgccaagta cgccccctat tgacgtcaat gacggtaaat
 301 ggcccgcctg gcattatgcc cagtacatga ccttatggga ctttcctact
 351 tcgcagtaca tctacgtatt agtcatcgct attaccatgg tgatgcggtt
 401 ttggcagtac atcaatgggc gtggatagcg gtttgactca cggggatttc
 451 caagtctcca ccccattgac gtcaatggga gtttgttttg gcaccaaaat
 501 caacgggact ttccaaaatg tcgtaacaac tccgccccat tgacgcaaat
 551 gggcggtagg cgtgtacggt gggaggtcta tataagcaga gctctctggc
 601 taactagaga acccactgct tactggctta tcgaaattaa tacgactcac
 651 tatagggaga cccaagcttc gcgacgtacg gccgccacca tgcagcgcgt
 701 gaacatgatc atggcagaat caccaggcct catcaccatc tgccttttag
 751 gatatctact cagtgctgaa tctacaggtt tctttccttt tttaaaatac
 801 attgagtatg cttgccttt agatatagaa atatctgatg ctgtcttctt
 851 cactaaattt tgattacatg atttgacagc aatattgaag agtctaacag
 901 ccagcacgca ggttggtaag tactgtggga acatcacaga ttttggctcc
 951 atgccctaaa gagaaattgg ctttcagatt atttggatta aaaacaaaga
1001 ctttcttaag agatgtaaaa ttttcatgat gttttctttt tgctaaaac
1051 taaagaatta ttcttttaca tttcagtttt tcttgatcat gaaaacgcca
1101 acaaaattct gaatcggcca aagaggtata attcaggtaa attggaagag
1151 tttgttcaag ggaatctaga gagagaatgt atggaagaaa agtgtagttt
1201 tgaagaagca cgagaagttt ttgaaaacac tgaaagaaca actgaatttt
1251 ggaagcagta tgttgatgga gatcagtgtg agtccaatcc atgtttaaat
1301 ggcggcagtt gcaaggatga cattaattcc tatgaatgtt ggtgtccctt
1351 tggatttgaa ggaaagaact gtgaattaga tgtaacatgt aacattaaga
1401 atggcagatg cgagcagttt tgtaaaaata gtgctgataa caaggtggtt
1451 tgctcctgta ctgagggata tcgacttgca gaaaaccaga agtcctgtga
1501 accagcagtg ccatttccat gtggaagagt tctgtgttca caaacttcta
1551 agctcacccg tactgagact gtttttcctg atgtggacta tgtaaattct
1601 actgaagctg aaaccatttt ggataacatc actcaaagca cccaatcatt
1651 taatgacttc actcgggttg ttggtggaga agatgccaaa ccaggtcaat
1701 tcccttggca ggttgttttg aatggtaaag ttgatgcatt ctgtggaggc
1751 tctatcgtta atgaaaaatg gattgtaact gctgcccact gtgttgaaac
1801 tggtgttaaa attacagttg tcgcaggtga acataatatt gaggagacag
1851 aacatacaga gcaaaagcga aatgtgattc gaattattcc tcaccacaac
1901 tacaatgcag ctattaataa gtacaaccat gacattgccc ttctggaact
1951 ggacgaaccc ttagtgctaa acagctacgt tacacctatt tgcattgctg
2001 acaaggaata cacgaacato ttcctcaaat ttggatctgg ctatgtaagt
2051 ggctggggaa gagtcttcca caaagggaga tcagctttag ttcttcagta
2101 ccttagagtt ccacttgttg accgagccac atgtcttcga tctacaaagt
2151 tcaccatcta taacaacato ttctgtgctg cttccatga aggaggtaga
2201 gattcatgtc aaggagatag tgggggaccc catgttactg aagtgaagg
2251 gaccagtttc ttaactggaa ttattagctg gggtgaagag tgtgcaatga
2301 aaggcaaata tggaatatat accaaggtat cccggtatgt caactggatt
2351 aaggaaaaaa caaagctcac tgacaaaact cacacatgcc caccgtgccc
2401 agctccggaa ctcctgggcg gaccgtcagt cttcctcttc cccccaaaac
2451 ccaaggacac cctcatgatc tcccggaccc ctgaggtcac atgcgtggtg
2501 gtggacgtga gccacgaaga ccctgaggtc aagttcaact ggtacgtgga
2551 cggcgtggag gtgcataatg ccaagacaaa gccgcgggag gagcagtaca
2601 acagcacgta ccgtgtggtc agcgtcctca ccgtcctgca ccaggactgg
2651 ctgaatggca aggagtacaa gtgcaaggtc tccaacaaag ccctcccagc
2701 ccccatcgag aaaaccatct ccaaagccaa agggcagccc cgagaaccac
```

TABLE 17-continued

Polynucleotide Sequences of FIX

```
2751 aggtgtacac cctgccccca tcccgggatg agctgaccaa gaaccaggtc
2801 agcctgacct gcctggtcaa aggcttctat cccagcgaca tcgccgtgga
2851 gtgggagagc aatgggcagc cggagaacaa ctacaagacc acgcctcccg
2901 tgttggactc cgacggctcc ttcttcctct acagcaagct caccgtggac
2951 aagagcaggt ggcagcaggg gaacgtcttc tcatgctccg tgatgcatga
3001 ggctctgcac aaccactaca cgcagaagag cctctccctg tctccgggta
3051 aatgagaatt cagacatgat aagatacatt gatgagtttg gacaaaccac
3101 aactagaatg cagtgaaaaa aatgctttat ttgtgaaatt tgtgatgcta
3151 ttgctttatt tgtaaccatt ataagctgca ataaacaagt tggggtgggc
3201 gaagaactcc agcatgagat ccccgcgctg gaggatcatc cagccggcgt
3251 cccggaaaac gattccgaag cccaacctttt catagaaggc ggcggtggaa
3301 tcgaaatctc gtagcacgtg tcagtcctgc tcctcggcca cgaagtgcac
3351 gcagttgccg gccgggtcgc gcagggcgaa ctccccgcccc cacggctgct
3401 cgccgatctc ggtcatggcc ggcccggagg cgtcccggaa gttcgtggac
3451 acgacctccg accactcggc gtacagctcg tccaggccgc gcacccacac
3501 ccaggccagg gtgttgtccg gcaccacctg gtcctggacc gcgctgatga
3551 acagggtcac gtcgtcccgg accacaccgg cgaagtcgtc ctccacgaag
3601 tcccgggaga cccgagccg gtcggtccag aactcgaccg ctccggcgac
3651 gtcgcgcgcg gtgagcaccg gaacggcact ggtcaacttg gccatggttt
3701 agttcctcac cttgtcgtat tatactatgc cgatatacta tgccgatgat
3751 taattgtcaa cacgtgctga tcagatccga aatggatat acaagctccc
3801 gggagctttt tgcaaaagcc taggcctcca aaaaagcctc ctcactactt
3851 ctggaatagc tcagaggcag aggcggcctc ggcctctgca taaataaaaa
3901 aaattagtca gccatgggc ggagaatggg cggaactggg cggagttagg
3951 ggcgggatgg gcggagttag gggcgggact atggttgctg actaattgag
4001 atgcatgctt tgcatacttc tgcctgctgg ggagcctggg gactttccac
4051 acctggttgc tgactaattg agatgcatgc tttgcatact tctgcctgct
4101 ggggagcctg gggactttcc acaccctcgt cgagctagct tcgtgaggct
4151 ccggtgcccg tcagtgggca gagcgcacat cgcccacagt ccccgagaag
4201 ttgggggag gggtcggcaa ttgaaccggt gcctagagaa ggtggcgcgg
4251 ggtaaactgg gaaagtgatg tcgtgtactg gctccgcctt tttcccgagg
4301 gtgggggaga accgtatata agtgcagtag tcgccgtgaa cgttcttttt
4351 cgcaacgggt ttgccgccag aacacaggta agtgccgtgt gtggttcccg
4401 cgggcctggc ctctttacgg gttatggccc ttgcgtgcct tgaattactt
4451 ccacctggct ccagtacgtg attcttgatc ccgagctgga gccaggggcg
4501 ggccttgcgc tttaggagcc ccttcgcctc gtgcttgagt tgaggcctgg
4551 cctgggcgct ggggccgccg cgtgcgaatc tggtggcacc ttcgcgcctg
4601 tctcgctgct ttcgataagt ctctagccat ttaaaatttt tgatgacctg
4651 ctgcgacgct ttttttctgg caagatagtc ttgtaaatgc gggccaggat
4701 ctgcacactg gtatttcggt ttttggggcc gcgggcggcg acggggccgg
4751 tgcgtcccag cgcacatgtt cggcgaggcg gggcctgcga gcgcggccac
4801 cgagaatcgg acggggtag tctcaagctg gccggcctgc tctggtgcct
4851 ggcctcgcgc cgccgtgtat cgccccgccc tgggcggcaa ggctggcccg
4901 gtcggcacca gttgcgtgag cggaaagatg gccgcttccc ggccctgctc
4951 caggggctc aaaatggagg acgcggcgct cgggagagcg ggcgggtgag
5001 tcacccacac aaaggaaagg ggcctttccg tcctcagccg tcgcttcatg
5051 tgactccacg gagtaccggg cgccgtccag gcacctcgat tagttctgga
5101 gcttttggag tacgtcgtct ttaggttggg gggaggggtt ttatgcgatg
5151 gagtttcccc acactgagtg ggtggagact gaagttaggc cagcttggca
5201 cttgatgtaa ttctccttgg aatttgccct ttttgagttt ggatcttggt
5251 tcattctcaa gcctcagaca gtggttcaaa gttttttct tccatttcag
5301 gtgtcgtgaa cacgtggtcg cggccgcgcc gccaccatgg agacagacac
5351 actcctgcta tgggtactgc tgctctgggt tccaggttcc actggtgaca
5401 aaactcacac atgccaccg tgcccagcac ctgaactcct gggaggaccg
5451 tcagtcttcc tcttcccccc aaaacccaag gacaccctca tgatctcccg
5501 gacccctgag gtcacatgcg tggtggtgga cgtgagccac gaagaccctg
5551 aggtcaagtt caactggtac gtggacggcg tggaggtgca taatgccaag
5601 acaaagccgc gggaggagca gtacaacagc acgtaccgtg tggtcagcgt
5651 cctcaccgtc ctgcaccagg actggctgaa tcgcaaggag tacaagtgca
5701 aggtctccaa caaagccctc ccagccccca tcgagaaaac catctccaaa
5751 gccaaagggc agccccgaga accacaggtg tacaccctgc ccccatcccg
5801 cgatgagctg accaagaacc aggtcagcct gacctgcctg gtcaaaggct
5851 tctatcccag cgacatcgcc gtggagtggg agagcaatgg gcagccggag
5901 aacaactaca agaccacgcc tcccgtgttg gactccgacg gctccttctt
5951 cctctacagc aagctcaccg tggacaagag caggtggcag caggggaacg
6001 tcttctcatg ctccgtgatg catgaggctc tgcacaacca ctacacgcag
6051 aagagcctct ccctgtctcc gggtaaatga ctcgagagat ctggccggct
6101 gggcccgttt cgaaggtaag cctatcccta accctctcct cggtctcgat
6151 tctacgcgta ccggtcatca tcaccatcac cattgagttt aaacccgctg
6201 atcagcctcg actgtgcctt ctagttgcca gccatctgtt gtttgcccct
6251 cccccgtgcc ttccttgacc ctggaaggtg ccactcccac tgtcctttcc
6301 taataaaatg aggaaattgc atcgcattgt ctgagtaggt gtcattctat
6351 tctgggggt gggtggggc aggacagcaa gggggaggat tgggaagaca
6401 atagcaggca tgctggggat gcggtgggct ctatggcttc tgaggcggaa
6451 agaaccagtg gcggtaatac ggttatccac agaatcaggg gataacgcag
6501 gaaagaacat gtgagcaaaa ggccagcaaa aggccaggaa ccgtaaaaag
6551 gccgcgttgc tggcgttttt ccataggctc cgcccccctg acgagcatca
6601 caaaaatcga cgctcaagtc agaggtggcg aaacccgaca ggactataaa
```

TABLE 17-continued

Polynucleotide Sequences of FIX

```
6651 gataccaggc gtttccccct agaagctccc tcgtgcgctc tcctgttccg
6701 accctgccgc ttaccggata cctgtccgcc tttctccctt cgggaagcgt
6751 ggcgctttct catagctcac gctgtaggta tctcagttcg gtgtaggtcg
6801 ttcgctccaa gctgggctgt gtgcacgaac ccccgttca gcccgaccgc
6851 tgcgccttat ccggtaacta tcgtcttgag tccaacccgg taagacacga
6901 cttatcgcca ctggcagcag ccactggtaa caggattagc agagcgaggt
6951 atgtaggcgg tgctacagag ttcttgaagt ggtggcctaa ctacggctac
7001 actagaagaa cagtatttgg tatctgcgct ctgctgaagc cagttacctt
7051 cggaaaaaga gttggtagct cttgatccgg caaacaaacc accgctggta
7101 gcggtggttt ttttgtttgc aagcagcaga ttacgcgcag aaaaaaagga
7151 tctcaagaag atcctttgat cttttctacg gggtctgacg ctcagtggaa
7201 cgaaaactca ccttaaggga ttttggtcat gacattaacc tataaaaata
7251 ggcgtatcac gaggcccttt cgtctcgcgc gtttcggtga tgacggtgaa
7301 aacctctgac acatgcagct cccggagacg gtcacagctt gtctgtaagc
7351 ggatgccggg agcagacaag cccgtcaggg cgcgtcagcg ggtgttgcgg
7401 ggtgtcgggg ctggcttaac tatgcggcat cagagcagat tgtactgaga
7451 gtgcaccata tatgcggtgt gaaataccgc acagatgcgt aaggagaaaa
7501 taccgcatca ggcgccattc gccattcagg ctgcgcaact gttgggaagg
7551 gcgatcggtg cgggcctctt cgctattacg cca
```

TABLE 18

Polypeptide Sequences of FIX

FIX-Fc Monomer Hybrid: created by coexpressing FIX-Fc and Fc chains.

A. FIX-Fc chain (46 amino acid signal sequence underlined) (SEQ ID NO: 14)

The c-terminal lysine is not present in either subunit; this processing
is often observed in recombinant proteins produced in mammalian cell culture,
as well as with plasma derived proteins.

FIX-Fc-SC Subunit (the Fc part of FIX-Fc is in bold):
```
  1 MQRVNMIMAE SPSLITICLL GYLLSAECTV FLDHENANKI LNRPKRYNSG
 51 KLEEFVQGNL ERECMEEKCS FEEAREVFEN TERTTEFWKQ YVDGDQCESN
101 PCLNGGSCKD DINSYECWCP FGFEGKNCEL DVTCNIKNGR CEQFCKNSAD
151 NKVVCSCTEG YRLAENQKSC EPAVPFPCGR VSVSQTSKLT RAETVFPDVD
201 YVNSTEAETI LDNITQSTQS FNDFTRVVGG EDAKPGQFPW QVVLNGKVDA
251 FCGGSIVNEK WIVTAAHCVE TGVKITVVAG EHNIEETEHT EQKRNVIRII
301 PHHNYNAAIN KYNHDIALLE LDEPLVLNSY VTPICIADKE YTNIFLKFGS
351 GYVSGWGRVF HKGRSALVLQ YLRVPLVDRA TCLRSTKFTI YNNMFCAGFH
401 EGGRDSCQGD SGGPHVTEVE GTSFLTGIIS WGEECAMKGK YGIYTKVSRY
451 VNWIKEKTKL TDKTHTCPPC PAPELLGGPS VFLFPPKPKD TLMISRTPEV
501 TCVVVDVSHE DPEVKFNWYV DGVEVHNAKT KPREEQYNST YRVVSVLTVL
551 HQDWLNGKEY KCKVSNKALP APIEKTISKA KGQPREPQVY TLPPSRDELT
601 KNQVSLTCLV KGFYPSDIAV EWESNGQPEN NYKTTPPVLD SDGSFFLYSK
651 LTVDKSRWQQ GNVFSCSVMH EALHNHYTQK SLSLSPGK
```

TABLE 19

Polynucleotide sequences of FVII

A. Full Length FVII-Fc

Full Length FVII-Fc DNA Sequence (FVII signal peptide underlined,
Fc region in bold) (SEQ ID NO: 15, which encodes SEQ ID NO: 16)

```
  1 atggtctccc aggccctcag gctcctctgc cttctgcttg ggcttcaggg 51 ctgcctggct gcaggcgggg tcgctaaggc ctcaggagga gaaacacggg 101 acatgccgtg gaagccgggg cctcacagag tcttcgtaac ccaggaggaa 151 gccacggcg tcctgcaccg gcgccggcgc gccaacgcgt tcctggagga 201 gctgcggccg ggctccctgg agagggagtg caaggaggag cagtgctcct 251 tcgaggaggc ccggagatc ttcaaggacg cggagaggac gaagctgttc 301 tggatttctt acagtgatgg ggaccagtgt gcctcaagtc catgccagaa
```

TABLE 19-continued

| Polynucleotide sequences of FVII |
|---|

```
 351 tgggggctcc tgcaaggacc agctccagtc ctatatctgc ttctgcctcc
 401 ctgccttcga gggccggaac tgtgagacgc acaaggatga ccagctgatc
 451 tgtgtgaacg agaacggcgg ctgtgagcag tactgcagtg accacacggg
 501 caccaagcgc tcctgtcggt gccacgaggg gtactctctg ctggcagacg
 551 gggtgtcctg cacacccaca gttgaatatc catgtggaaa aatacctatt
 601 ctagaaaaaa gaaatgccag caaacccca ggccgaattg tgggggcaa
 651 ggtgtgcccc aaggggagt gtccatggca ggtcctgttg ttggtgaatg
 701 gagctcagtt gtgtgggggg accctgatca acaccatctg ggtggtctcc
 751 gcggcccact gtttcgacaa aatcaagaac tggaggaacc tgatcgcggt
 801 gctgggcgag cacgacctca gcgagcacga cggggatgag cagagccggc
 851 gggtggcgca ggtcatcatc cccagcacgt acgtcccggg caccaccaac
 901 cacgacatcg cgctgctccg cctgcaccag cccgtggtcc tcactgacca
 951 tgtggtgccc ctctgcctgc ccgaacggac gttctctgag aggacgctgg
1001 ccttcgtgcg cttctcattg gtcagcggct ggggccagct gctggaccgt
1051 ggcgccacgg ccctggagct catggtcctc aacgtgcccc ggctgatgac
1101 ccaggactgc ctgcagcagt cacggaaggt gggagactcc ccaaatatca
1151 cggagtacat gttctgtgcc ggctactcgg atggcagcaa ggactcctgc
1201 aagggggaca gtggaggccc acatgccacc cactaccggg gcacgtggta
1251 cctgacgggc atcgtcagct ggggccaggg ctgcgcaacc gtgggccact
1301 ttggggtgta caccagggtc tcccagtaca tcgagtggct gcaaaagctc
1351 atgcgctcag agccacgccc aggagtcctc ctgcgagccc catttcccta
1401 ggacaaaact cacacatgcc caccgtgccc agctccagaa ctcctgggcg
1451 gaccgtcagt cttcctcttc cccccaaaac ccaaggacac cctcatgatc
1501 tcccggaccc ctgaggtcac atgcgtggtg gtggacgtga gccacgaaga
1551 ccctgaggtc aagttcaact ggtacgtgga cggcgtggag gtgcataatg
1061 ccaagacaaa gccgcgggag gagcagtaca acagcacgta ccgtgtggtc
1651 agcgtcctca ccgtcctgca ccaggactgg ctgaatggca aggagtacaa
1701 gtgcaaggtc tccaacaaag ccctcccagc ccccatcgag aaaaccatct
1751 ccaaagccaa agggcagccc cgagaaccac aggtgtacac cctgccccca
1801 tcccgggatg agctgaccaa gaaccaggtc agcctgacct gcctggtcaa
1851 aggcttctat cccagcgaca tcgccgtgga gtgggagagc aatgggcagc
1901 cggagaacaa ctacaagacc acgcctcccg tgttggactc cgacggctcc
1951 ttcttcctct acagcaagct caccgtggac aagagcaggt ggcagcaggg
2001 gaacgtcttc tcatgctccg tgatgcatga ggctctgcac aaccactaca
2051 cgcagaagag cctctccctg tctccgggta aa
```

TABLE 20

| Polypeptide Sequences of FVII |
| --- |
| FIVII-Fc Monomer Hybrid: created by coexpressing FVII-Fc and Fc chains.<br><br>A. FVII-Fc chain (signal sequence underlined, Fc region is in bold)<br>(SEQ ID NO: 16)<br><br>FVII-Fc-Sc Subunit:<br>  1 <u>MVSQALRLLC LLLGLQGCLA</u> AGGVAKASGG ETRDMPWKPG PHRVFVTQEE<br><br> 51 <u>AHGVLHRRRR</u> ANAFLEELRP GSLERECKEE QCSFEEAREI FKDAERTKLF<br><br>101 WISYSDGDQC ASSPCQNGGS CKDQLQSYIC FCLPAFEGRN CETHKDDQLI<br><br>151 CVNENGGCEQ YCSDHTGTKR SCRCHEGYSL LADGVSCTPT VEYPCGKIPI<br><br>201 LEKRNASKPQ GRIVGGKVCP KGECPWQVLL LVNGAQLCGG TLINTIWVVS<br><br>251 AAHCFDKIKN WRNLIAVLGE HDLSEHDGDE QSRRVAQVII PSTYVPGTTN<br><br>301 HDIALLRLHQ PVVLTDHVVP LCLPERTFSE RTLAFVRFSL VSGWGQLLDR<br><br>351 GATALELMVL NVPRLMTQDC LQQSRKVGDS PNITEYMFCA GYSDGSKDSC<br><br>401 KGDSGGPHAT HYRGTWYLTG IVSWGQGCAT VGHFGVYTRV SQYIEWLQKL<br><br>451 MRSEPRPGVL LRAPFPDKTH TCPPCPAPEL LGGPSVFLFP PKPKDTLMIS<br><br>501 RTPEVTCVVV DVSHEDPEVK FNWYVDGVEV HNAKTKPREE QYNSTYRVVS<br><br>551 VLTVLHQDWL NGKEYKCKVS NKALPAPIEK TISKAKGQPR EPQVYTLPPS<br><br>601 RDELTKNQVS LTCLVKGFYP SDIAVEWESN GQPENNYKTT PPVLDSDGSF<br><br>651 FLYSKLTVDK SRWQQGNVFS CSVMHEALHN HYTQKSLSLS PGK |

What is claimed is:

1. A method of inactivating virus present during production of a polypeptide of interest, comprising:
   (a) binding the polypeptide to a chromatography matrix,
   (b) performing a virus inactivation step by washing the polypeptide-bound chromatography matrix with a wash solution at a pH of lower than about 4.0,
   (c) eluting the polypeptide from the chromatography matrix with a low-salt elution solution, wherein the wash solution comprises a sufficient concentration of salt to substantially reduce elution of the polypeptide during the virus inactivation step.

2. The method of claim 1, wherein the chromatography matrix is an affinity chromatography matrix.

3. The method of claim 2, wherein the affinity chromatography matrix is a Protein A column.

4. The method of claim 3, wherein the Protein A ligand is immobilized on a matrix selected from the group consisting of dextran based matrix, agarose based matrix, polystyrene based matrix, hydrophilic polyvinyl ethyl based matrix, rigid polymethacrylate based matrix, porous polymer based matrix, controlled pore glass based matrix, and any combination thereof.

5. The method of claim 1, wherein the chromatography matrix is a mixed-mode anion-exchange chromatography matrix.

6. The method of claim 1, wherein the pH of the wash solution is about 2.5 to about 4.0, about 2.5 to about 3.0, about 3.0 to about 3.5, or about 3.5 to about 4.0.

7. The method of claim 1, wherein the concentration of the salt in the wash solution is greater than about 0.5 M.

8. The method of claim 1, wherein the salt in the wash solution is a sodium salt, a potassium salt, or an ammonium salt.

9. The method of claim 8, wherein the sodium salt is NaCl.

10. The method of claim 8, wherein the ammonium salt is ammonium sulfate.

11. The method of claim 1, wherein the wash solution further comprises one or more components selected from the group consisting of a polymer, an organic solvent, a detergent, arginine, an arginine derivative, and any combination thereof.

12. The method of claim 1, wherein the method comprises more than one virus-inactivation step, wherein the virus-inactivation steps use identical or different wash solutions.

13. The method of claim 1, wherein the polypeptide is recombinantly produced in a cell culture.

14. The method of claim 13, wherein the cell culture is a human cell culture.

15. The method of claim 14, wherein the human cell is a Human Embryonic Kidney (HEK) 293 cell.

16. The method of claim 1, wherein, prior to the binding and virus inactivation steps, the polypeptide is harvested after recombinant production in a cell culture.

17. The method of claim 1, wherein the polypeptide comprises CH2/CH3 domains of an immunoglobulin constant region.

18. The method of claim 17, wherein the polypeptide further comprises a heterologous moiety.

19. The method of claim 1, wherein the polypeptide comprises a clotting factor.

20. The method of claim 1, wherein the polypeptide comprises an antibody or an antibody fragment.

21. A method of inactivating virus present during production of a recombinantly produced polypeptide of interest, comprising:
   (a) binding the polypeptide to a chromatography matrix,
   (b) performing a virus inactivation step by washing the polypeptide-bound chromatography matrix with a wash solution, wherein the wash solution has a concentration of salt that is greater than about 0.5 M and a pH of less than about 4.0, and
   (c) eluting the polypeptide from the chromatography matrix with a low-salt elution solution.

* * * * *